(12) United States Patent
Fischer et al.

(10) Patent No.: US 8,629,084 B2
(45) Date of Patent: Jan. 14, 2014

(54) IODINE-PHENYL-SUBSTITUTED CYCLIC CETOENOLS

(75) Inventors: Reiner Fischer, Monheim (DE); Thomas Bretschneider, Lohmar (DE); Kerstin Ilg, Köln (DE); Stefan Lehr, Liederbach (DE); Dieter Feucht, Eschborn (DE); Olga Malsam, Rösrath (DE); Udo Reckmann, Köln (DE); Guido Bojack, Wiesbaden (DE); Christian Arnold, Langenfeld (DE); Thomas Auler, Leichlingen (DE); Martin Jeffrey Hills, Idstein (DE); Heinz Kehne, Hofheim (DE); Waltraud Hempel, Liederbach (DE); Erich Sanwald, Kiel (DE)

(73) Assignee: Bayer CropScience AG, Monheim (DE)

( * ) Notice: Subject to any disclaimer, the term of this patent is extended or adjusted under 35 U.S.C. 154(b) by 1169 days.

(21) Appl. No.: 11/663,029

(22) PCT Filed: Sep. 13, 2005

(86) PCT No.: PCT/EP2005/009807
§ 371 (c)(1),
(2), (4) Date: Jun. 10, 2009

(87) PCT Pub. No.: WO2006/029799
PCT Pub. Date: Mar. 23, 2006

(65) Prior Publication Data
US 2010/0009850 A1    Jan. 14, 2010

(30) Foreign Application Priority Data

Sep. 16, 2004 (DE) .......................... 10 2004 044 827

(51) Int. Cl.
*A01N 43/36*    (2006.01)
*C07D 491/107*  (2006.01)
*C07D 209/54*   (2006.01)
*C07D 207/273*  (2006.01)
*A01N 43/38*    (2006.01)

(52) U.S. Cl.
USPC ........... 504/283; 504/284; 514/409; 514/425; 548/410; 548/513; 548/544

(58) Field of Classification Search
USPC .................. 504/283, 248; 514/409, 425, 456; 548/410, 513, 544
See application file for complete search history.

(56) References Cited

U.S. PATENT DOCUMENTS

| | | |
|---|---|---|
| 3,542,809 A | 11/1970 | Nakanishi |
| 4,021,224 A | 5/1977 | Pallos et al. |
| 4,091,006 A | 5/1978 | Durden, Jr. et al. |
| 4,175,135 A | 11/1979 | Haines |
| 4,186,130 A | 1/1980 | Teach |
| 4,209,432 A | 6/1980 | Roth |
| 4,209,532 A | 6/1980 | Wheeler |
| 4,256,657 A | 3/1981 | Wheeler |
| 4,256,658 A | 3/1981 | Wheeler |
| 4,256,659 A | 3/1981 | Wheeler |
| 4,257,858 A | 3/1981 | Wheeler |
| 4,283,348 A | 8/1981 | Wheeler |
| 4,283,532 A | 8/1981 | Nohara |
| 4,303,669 A | 12/1981 | D'Silva |
| 4,338,122 A | 7/1982 | Wheeler |
| 4,351,666 A | 9/1982 | Koerwer |
| 4,409,153 A | 10/1983 | Hodakowski |
| 4,436,666 A | 3/1984 | Wheeler |
| 4,526,723 A | 7/1985 | Wheeler et al. |
| 4,551,547 A | 11/1985 | Wheeler |
| 4,613,617 A | 9/1986 | Sousa |
| 4,623,727 A | 11/1986 | Hübele |
| 4,632,698 A | 12/1986 | Wheeler |
| 4,639,266 A | 1/1987 | Heubach et al. |
| 4,659,372 A | 4/1987 | Wheeler |

(Continued)

FOREIGN PATENT DOCUMENTS

| | | |
|---|---|---|
| AU | 726090 B2 | 4/1998 |
| CA | 2 298 033 A1 | 3/1999 |

(Continued)

OTHER PUBLICATIONS

Baciocchi, E., et al., "Dimethyl Arylmalonates from Cerium(IV) Ammonium Nitrate Promoted Reactions of Dimethyl Malonate with Aromatic Compounds in Methanol," *Tetrahedron Lett.* 27:2763-2766, Pergamon Journals Ltd. (1986).

Balthazor, T.M., et al., "Synthesis and Structure of Benziodazoles," *J. Org. Chem.* 44:1447-1449, American Chemical Society (1979).

Bhattacharya, B., "Isoquinoline Derivatives: Part XVIII—Formation of I-Alkyl-(or alkaryl or aryl)-3-methyl-7-chloro-(or 5-chloro)-isoquinolines," *Indian J. Chem.* 6:341-345, Council of Scientific and Industrial Research (1968).

Breslow, R., et al., "Selective Halogenation of Steroids Using Attached Aryl Iodide Templates," *J. Am. Chem. Soc.* 99:905-915, American Chemical Society (1977).

Campbell, A.C., et al., "Synthesis of (*E*)- and (*Z*)-Pulvinones," *J. Chem. Soc. Perkin Trans.* 1:1567-1576, The Chemical Society (1985).

(Continued)

*Primary Examiner* — Noble Jarrell
*Assistant Examiner* — Valerie Rodriguez-Garcia
(74) *Attorney, Agent, or Firm* — Sterne, Kessler, Goldstein & Fox P.L.L.C.

(57) ABSTRACT

The invention relates to novel iodophenyl-substituted cyclic ketonols of the formula (I)

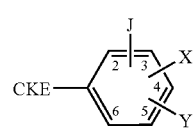

(I)

in which CKE, J, X and Y are as defined above, to a plurality of processes and intermediates for their preparation and to their use as pesticides and/or herbicides, and also to selective herbicidal compositions comprising firstly iodophenyl-substituted cyclic ketonols of the formula (I) and secondly at least one crop plant compatibility-improving compound.

11 Claims, No Drawings

(56) References Cited

U.S. PATENT DOCUMENTS

| | | | |
|---|---|---|---|
| 4,881,966 A | 11/1989 | Nyffeler et al. | |
| 4,891,057 A | 1/1990 | Sohn et al. | |
| 4,902,340 A | 2/1990 | Hubele | |
| 4,925,868 A | 5/1990 | Terao et al. | |
| 4,985,063 A | 1/1991 | Fischer et al. | |
| 5,045,560 A | 9/1991 | Fischer et al. | |
| 5,094,681 A | 3/1992 | Krämer et al. | |
| 5,116,836 A | 5/1992 | Fischer et al. | |
| 5,138,563 A | 8/1992 | Debitsch et al. | |
| 5,225,434 A | 7/1993 | Bertram et al. | |
| 5,258,527 A | 11/1993 | Krauskopf et al. | |
| 5,262,383 A | 11/1993 | Fischer et al. | |
| 5,314,863 A | 5/1994 | Löher et al. | |
| 5,332,720 A | 7/1994 | Krüger et al. | |
| 5,350,861 A * | 9/1994 | Fischer et al. | 548/544 |
| 5,380,852 A | 1/1995 | Schütze et al. | |
| 5,393,729 A | 2/1995 | Fischer et al. | |
| 5,401,700 A | 3/1995 | Sohn et al. | |
| 5,407,897 A | 4/1995 | Cary et al. | |
| 5,494,890 A | 2/1996 | Cederbaum et al. | |
| 5,504,057 A | 4/1996 | Fischer et al. | |
| 5,516,750 A | 5/1996 | Willms et al. | |
| 5,565,450 A | 10/1996 | Fischer et al. | |
| 5,567,671 A | 10/1996 | Fischer et al. | |
| 5,589,469 A | 12/1996 | Fischer et al. | |
| 5,610,122 A | 3/1997 | Fischer et al. | |
| 5,622,917 A * | 4/1997 | Fischer et al. | 504/283 |
| 5,677,449 A | 10/1997 | Fischer et al. | |
| 5,683,965 A | 11/1997 | Bachmann et al. | |
| 5,700,758 A | 12/1997 | Rösch et al. | |
| 5,739,079 A | 4/1998 | Holdgrün | |
| 5,808,135 A | 9/1998 | Fischer et al. | |
| 5,830,825 A | 11/1998 | Fischer et al. | |
| 5,830,826 A | 11/1998 | Fischer et al. | |
| 5,840,661 A | 11/1998 | Fischer et al. | |
| 5,945,444 A | 8/1999 | Fischer et al. | |
| 5,960,443 A | 9/1999 | Young et al. | |
| 5,977,029 A | 11/1999 | Fischer et al. | |
| 6,071,937 A | 6/2000 | Bretschneider et al. | |
| 6,114,374 A | 9/2000 | Lieb et al. | |
| 6,133,296 A | 10/2000 | Lieb et al. | |
| 6,140,358 A | 10/2000 | Lieb et al. | |
| 6,200,932 B1 | 3/2001 | Fischer et al. | |
| 6,235,680 B1 | 5/2001 | Ziemer et al. | |
| 6,251,827 B1 | 6/2001 | Ziemer et al. | |
| 6,251,833 B1 | 6/2001 | Erdelen et al. | |
| 6,316,486 B1 * | 11/2001 | Lieb et al. | 514/411 |
| 6,410,480 B1 | 6/2002 | Mühlebach et al. | |
| 6,472,419 B1 | 10/2002 | Fischer et al. | |
| 6,515,184 B1 | 2/2003 | Fischer et al. | |
| 6,555,499 B1 | 4/2003 | Glock et al. | |
| 6,589,976 B1 | 7/2003 | Fischer et al. | |
| 6,642,180 B1 | 11/2003 | Fischer et al. | |
| 6,861,391 B1 | 3/2005 | Fischer et al. | |
| 6,894,005 B1 | 5/2005 | Maetzke et al. | |
| 2002/0022575 A1 | 2/2002 | Fischer et al. | |
| 2002/0072617 A1 | 6/2002 | Hagemann et al. | |
| 2002/0188136 A1 | 12/2002 | Lieb et al. | |
| 2003/0045432 A1 | 3/2003 | Fischer et al. | |
| 2003/0073851 A1 | 4/2003 | Lieb et al. | |
| 2003/0096806 A1 | 5/2003 | Lieb et al. | |
| 2003/0171219 A1 | 9/2003 | Lieb et al. | |
| 2003/0171220 A1 | 9/2003 | Ziemer et al. | |
| 2003/0199572 A1 | 10/2003 | Lieb et al. | |
| 2003/0216260 A1 | 11/2003 | Ruther et al. | |
| 2003/0228984 A1 | 12/2003 | Hagemann et al. | |
| 2004/0266624 A1 | 12/2004 | Hofer | |
| 2005/0054535 A1 | 3/2005 | Fischer et al. | |
| 2005/0090399 A1 | 4/2005 | Friedmann et al. | |
| 2005/0164886 A1 | 7/2005 | Glock | |
| 2006/0160847 A1 | 7/2006 | Fischer et al. | |
| 2006/0166829 A1 | 7/2006 | Fischer et al. | |
| 2007/0015825 A1 | 1/2007 | Fischer et al. | |
| 2007/0066488 A1 | 3/2007 | Fischer et al. | |
| 2007/0093391 A1 | 4/2007 | Fischer et al. | |
| 2007/0129252 A1 | 6/2007 | Fischer et al. | |
| 2007/0225167 A1 | 9/2007 | Fischer et al. | |
| 2007/0225170 A1 | 9/2007 | Fischer et al. | |
| 2007/0244007 A1 * | 10/2007 | Fischer et al. | 504/104 |
| 2007/0254949 A1 | 11/2007 | Bretschneider et al. | |
| 2007/0265266 A1 | 11/2007 | Fischer et al. | |
| 2007/0270416 A1 | 11/2007 | Funke et al. | |
| 2007/0276023 A1 | 11/2007 | Fischer et al. | |
| 2007/0298968 A1 | 12/2007 | Bretschneider et al. | |
| 2007/0298969 A1 | 12/2007 | Fischer et al. | |

FOREIGN PATENT DOCUMENTS

| | | |
|---|---|---|
| CA | 2 382 432 A1 | 3/2001 |
| CA | 2 382 491 A1 | 3/2001 |
| CA | 2 492 096 A1 | 1/2004 |
| CA | 2 497 074 A1 | 3/2004 |
| CA | 2 513 510 A1 | 8/2004 |
| CA | 2 518 620 A1 | 9/2004 |
| CA | 2 535 512 A1 | 2/2005 |
| CA | 2 544 537 A1 | 5/2005 |
| CA | 2 544 548 A1 | 5/2005 |
| CA | 2 546 815 A1 | 6/2005 |
| CA | 2 546 817 A1 | 6/2005 |
| EP | 0 346 620 A1 | 12/1989 |
| EP | 0 442 077 B1 | 8/1991 |
| GB | 2 266 888 A | 11/1993 |
| JP | 2000-53670 A | 2/2000 |
| WO | WO 94/29268 A1 | 12/1994 |
| WO | WO 96/02539 A1 | 2/1996 |
| WO | WO 96/11574 A1 | 4/1996 |
| WO | WO 96/21652 A1 | 7/1996 |
| WO | WO 99/11605 A1 | 3/1999 |
| WO | WO 00/47585 A1 | 8/2000 |
| WO | WO 04/000152 A2 | 12/2003 |
| WO | WO 2004/048314 A1 | 6/2004 |
| WO | WO 2004/065366 A1 | 8/2004 |

OTHER PUBLICATIONS

CAPLUS Database, Accession No. 1975:453382, Deckart, H., et al., "Pharmacokinetics of new radioiodine-labeled aromatic acids," *Radiobiol. Radiother.* 15:27-38, Verlag Volk Und Gesundheit (1974).

Carson, J.R., et al., "2-Ethynylbenzenealkanamines. A New Class of Calcium Entry Blockers," *J. Med. Chem.* 31:630-636, American Chemical Society (1988).

Chambers, M.S., et al., "An Asymmetric Synthesis of Thiotetronic Acids using Chirality Transfer via an Allyl Xanthate-to-Dithiocarbonate Rearrangement. X-Ray Crystal Structure of (5R)-2,5-Dihydro-4-hydroxy-5-methyl-3-phenyl-5-prop-1'-enyl-2-oxothiophene," *J. Chem. Soc., Chem. Commun.*, pp. 1228-1230, The Chemical Society (1987).

Compagnon, P.L., and Miocque, M., "Addition des Réactifs Nucléophiles sur la Triple Liaison Nitrile," *Ann. Chim.* 5:11-22, Masson (1970).

Edward, J.T., and Jitrangsri, C., "Stereochemistry of the Bucherer-Bergs and Strecker Reactions of 4-*tert*-Butylcyclohexanone," *Can J. Chem.* 53:3339-3350, NRC Research Press (1975).

Edwards, R.L., et al., "Constituents of the Higher Fungi. Part IV. Involutin, a Diphenyl-cyclopenteneone from *Paxillus involutus* (Oeder ex Fries)," *J. Chem. Soc. (C)*, pp. 405-409, Chemical Society (1967).

Harrison, H.R., et al., "Use of molecular sieves in the methyl esterification of carboxylic acids," *Chem. Ind.*, p. 1568, Society of Chemical Industry (1968).

Ketcham, R., et al., "Synthesis of Heterocycles. 174 (1,2) Substituted Thiazines and Bisthiazinyls from Dithiooxamide and Trichlorophenyl Malonates," *J. Heterocycl. Chem.* 10:223-224, Journal of Heterocyclic Chemistry (1973).

Larock, R.C., and Yum, E.K., "Palladium-catalyzed Annulation of Vinylic Cyclopropanes and Cyclobutanes," *Tetrahedron* 52:2743-2758, Elsevier Science Ltd., (1996).

Micklefield, J., et al., "Alkylation and Acylation of 5-Phenylsulphonyl- and 5-Cyanobutyrolactones," *Tetrahedron* 48:7519-7526, Pergamon Press Ltd. (1992).

Munday, L., "Amino-acids of the Cyclohexane Series. Part I.," *J. Chem. Soc.*, pp. 4372-4379, American Chemical Society (1961).

(56) References Cited

OTHER PUBLICATIONS

Nakanishi, S., and Butler, K., "Synthesis of Chlorocarbonyl Ketenes," *Org. Prep. Procedures Int.* 7:155-158, Organic Preparations and Procedures, Inc. (1975).

Schmierer, R., and Mildenberger, H., "Cyclisierung von N-ACylalanin-und N-Acylglycinestern," *Liebigs Ann. Chem.*, pp. 1095-1098, VCH Verlagsgesellschaft mbH (1985).

Sonntag, N.O.V., "The Reactions of Aliphatic Acid Chlorides," *Chem. Rev.* 52:237-416, American Chemical Society (1953).

Sousa, A.A., et al., "Esters of 3-Hydroxy-2-Arylindones, a New Class of Acaricide," *J. Econ. Entomol.* 66:584-586, Entomological Society of America (1973).

Suzuki, S., et al., "Studies on Antiviral Agents. Biological Activity of Tenuazonic Acid Derivatives," *Chem. Pharm. Bull.* 15:1120-1122, Pharmaceutical Society of Japan (1967).

Tsuzuki, K., and Ōmura, S., "Syntheses and Biological Activities of Thiotetromycin Analogs," *J. Antibiotics* XXXVI:1589-1591, Japan Antibiotics Research Association (1983).

Wheeler, T.N., "Novel Photochemical Synthesis of 2-Aryl-1,3-cyclohexanediones," *J. Org. Chem.* 44:4906-4912, American Chemical Society (1979).

International Search Report for International Application No. PCT/EP2005/009807, European Patent Office, Netherlands, mailed on Feb. 1, 2006.

Dialog File 351, Accession No. 4963457, English language abstract for EP 0 346 620 A1, (1989).

Dialog File 351, Accession No. 5637204, English language abstract for EP 0 442 077 B1, (1995).

Patent Abstracts of Japan, English language abstract for JP 2000-53670 A, (2000).

Aidhen, I. S., and Ahuja, J. R., "A novel synthesis of benzocyclobutenones," *Tetrahedron Letters* 33(37):5431-5432, Pergamon Press Ltd., Great Britain (Sep. 1992).

Carson, J. R., et al., "2-Ethynylbenzenealkanamines. A new class of calcium entry blockers," *J. Med. Chem.* 31(3):630-636, American Chemical Society, United States (Mar. 1988).

Ishibashi, H., et al., "Stereoselective radical cascade approach to benzo[α]quinolizidines," *Tetrahedron Letters* 40(6):1149-1152, Elsevier Science Ltd., Great Britain (Feb. 1999).

Office Action mailed Sep. 28, 1998, in U.S. Appl. No. 08/945,664, Lieb et al., § 371(c) date Oct. 31, 1997 (issued as U.S. Patent No. 6,316,486).

Office Action mailed Apr. 23, 1999, in U.S. Appl. No. 08/945,664, Lieb et al., § 371(c) date Oct. 31, 1997 (issued as U.S. Patent No. 6,316,486).

Advisory Action mailed Jan. 13, 2000, in U.S. Appl. No. 08/945,664, Lieb et al., § 371(c) date Oct. 31, 1997 (issued as U.S. Patent No. 6,316,486).

Office Action mailed Apr. 12, 2000, in U.S. Appl. No. 08/945,664, Lieb et al., § 371(c) date Oct. 31, 1997 (issued as U.S. Patent No. 6,316,486).

Office Action mailed Aug. 25, 2000, in U.S. Appl. No. 08/945,664, Lieb et al., § 371(c) date Oct. 31, 1997 (issued as U.S. Patent No. 6,316,486).

Advisory Action mailed Jan. 11, 2001, in U.S. Appl. No. 08/945,664, Lieb et al., § 371(c) date Oct. 31, 1997 (issued as U.S. Patent No. 6,316,486).

Office Action mailed Aug. 15, 2011, in U.S. Appl. No. 12/083,691, Fischer et al., § 371(c) date May 4, 2009.

* cited by examiner

IODINE-PHENYL-SUBSTITUTED CYCLIC CETOENOLS

The present invention relates to novel iodophenyl-substituted cyclic ketoenols, to a plurality of processes for their preparation and for their use as pesticides and/or herbicides. The invention also provides selective herbicidal compositions comprising firstly iodophenyl-substituted cyclic ketoenols and secondly a crop plant compatibility-improving compound.

Pharmaceutical properties of 3-acylpyrrolidine-2,4-diones are described in the prior art (S. Suzuki et al. Chem. Pharm. Bull. 15 1120 (1967)). Furthermore, R. Schmierer and H. Mildenberger (Liebigs Ann. Chem. 1985, 1095) synthesized N-phenylpyrrolidine-2,4-diones. A biological activity of these compounds has not been described.

EP-A-0 262 399 and GB-A-2 266 888 disclose compounds of a similar structure (3-arylpyrrolidine-2,4-diones); however, a herbicidal, insecticidal or acaricidal action of these compounds is not known. Known to have a herbicidal, insecticidal or acaricidal action are unsubstituted, bicyclic 3-arylpyrrolidine-2,4-dione derivatives (EP-A-355 599, EP-A415 211 and JP-A-12-053 670), and also substituted monocyclic 3-arylpyrrolidine-2,4-dione derivatives (EP-A-377 893 and EP-A-442 077).

Also known are polycyclic 3-arylpyrrolidine-2,4-dione derivatives (EP-A-442 073), and also 1H-arylpyrrolidinedione derivatives (EP-A456 063, EP-A-521 334, EP-A-596 298, EP-A-613 884, EP-A-613 885, WO 95/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869 and WO 99/55673, WO 01/17972, WO 01/23354, WO 01/74770, WO 03/013249, WO 04/007448, WO 04/024688, WO 04/065366, WO 04/080962, WO 04/111042, WO 05/044791, WO 05/044796, WO 05/048710, WO 05/049596, DE-A-04 001 433.

It is known that certain substituted Δ³-dihydrofuran-2-one derivatives have herbicidal properties (cf. DE-A-4 014 420). The synthesis of the tetronic acid derivatives (such as, for example, 3-(2-methylphenyl)-4-hydroxy-5-(4-fluorophenyl)-Δ³-dihydrofuran-2-one) used as starting materials is also described in DE-A-4 014 420. Compounds of a similar structure with no stated insecticidal and/or acaricidal activity are known from the publication Campbell et al., J. Chem. Soc., Perkin Trans. 1, 1985, (8) 1567-76. Furthermore, 3-aryl-Δ³-dihydrofuranone derivatives having herbicidal, acaricidal and insecticidal properties are known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354 and WO 01/74770, WO 03/013 249, WO 04/024 688, WO 04/080 962, WO 04/111 042. Also known are 3-aryl-Δ³-dihydrothiphenone derivatives (WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/013249, WO 04/080 962, WO 04/111 042).

Certain phenylpyrone derivatives unsubstituted in the phenyl ring are already known (cf. A. M. Chirazi, T. Kappe and E. Ziegler, Arch. Pharm. 309, 558 (1976) and K.-H. Boltze and K. Heidenbluth, Chem. Ber. 91, 2849); however, a possible use of these compounds as pesticides is not stated. Phenylpyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972, WO 01/74770, WO 03/013249, WO 04/080 962, WO 04/111 042.

Certain 5-phenyl-1,3-thiazine derivatives which are unsubstituted in the phenyl ring are already known (cf. E. Ziegler and E. Steiner, Monatsh. 95, 147 (1964), R. Ketcham, T. Kappe and E. Ziegler, J. Heterocycl. Chem. 10, 223 (1973)); however, a possible use of these compounds as pesticides is not stated. 5-Phenyl-1,3-thiazine derivatives which are substituted in the phenyl ring and have herbicidal, acaricidal and insecticidal action are described in WO 94/14 785, WO 96/02 539, WO 96/35 664, WO 97/01 535, WO 97/02 243, WO 97/02 243, WO 97/36 868, WO 99/05638, WO 99/43649, WO 99/48869, WO 99/55673, WO 01/17972, WO 01/74770, WO 03/013249, WO 04/080 962, WO 04/111 042.

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673, WO 01/17972, WO 01/74770, WO 03/013249, WO 04/080 962, WO 04/111 042). Also known are compounds substituted in a similar manner; 3-hydroxy-5,5-dimethyl-2-phenylcyclopent-2-ene-1-one from the publication Micklefield et al., Tetrahedron, (1992), 7519-26 and the natural compound involutin (-)-cis-5-(3,4-dihydroxyphenyl)-3,4-dihydroxy-2-(4-hydroxyphenyl)cyclopent-2-enone from the publication Edwards et al., J. Chem. Soc. S, (1967), 405-9. An insecticidal or acaricidal action is not described. Also known is 2-(2,4,6-trimethylphenyl)-1,3-indanedione from the publication J. Economic Entomology, 66, (1973), 584 and the laid-open publication DE-A 2 361 084, with herbicidal and acaricidal actions being stated.

It is known that certain substituted 2-arylcyclohexanediones have herbicidal, insecticidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979)), WO 99/43649, WO 99/48869, WO 99/55673, WO 01/17972, WO 01/74770, WO 03/013249, WO 04/080 962, WO 04/111 042).

It is known that certain substituted 4-arylpyrazolidine-3,5-diones have acaricidal, insecticidal and herbicidal properties (cf., for example, WO 92/16 510, EP-A-508 126, WO 96/11 574, WO 96/21 652, WO 99/47525, WO 01/17 351, WO 01/17 352, WO 01/17 353, WO 01/17 972, WO 01/17 973, WO 03/028 466, WO 03/062 244, WO 04/080 962, WO 04/111 042, WO 05/005428, WO 05/016873).

However, the efficacy and activity spectrum of these compounds, in particular at low application rates and concentrations, are not always satisfactory. Furthermore, the compatibility of these compounds with crops is not always sufficient.

This invention now provides novel compounds of the formula

(I)

in which

J represents iodine, x represents hydrogen, alkyl, halogen, haloalkyl, alkoxy or haloalkoxy, Y represents hydrogen, alkyl, halogen or alkoxy, with the proviso that at least one of the radicals J, X or Y is located in the 2-position of the phenyl radical and is not hydrogen, CKE represents one of the groups

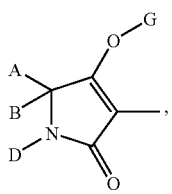
(1)

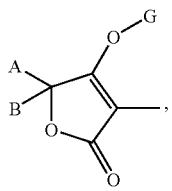
(2)

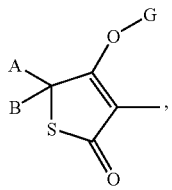
(3)

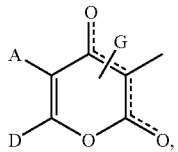
(4)

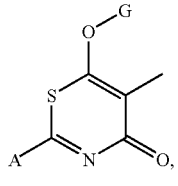
(5)

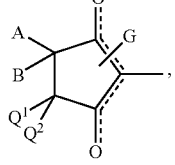
(6)

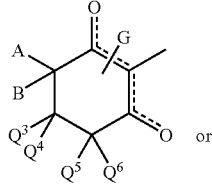
(7)

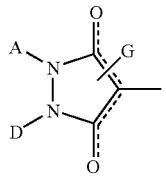
(8)

in which

A represents hydrogen, in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, arylalkyl, aryl, hetarylalkyl or hetaryl or A and D together with the atoms to which they are attached represent a saturated or unsaturated cycle which is unsubstituted or substituted in the A,D moiety and optionally contains at least one (in the case of CKE=8 one further) heteroatom, or A and $Q^1$ together represent alkanediyl or alkenediyl, optionally substituted by hydroxyl, in each case optionally substituted alkyl, alkoxy, alkylthio, cycloalkyl, benzyloxy or aryl or $Q^1$ represents hydrogen or alkyl, $Q^2$, $Q^4$, $Q^5$ and $Q^6$ independently of one another represent hydrogen or alkyl, $Q^3$ represents hydrogen, represents optionally substituted alkyl, alkoxyalkyl, alkylthioalkyl, optionally substituted cycloalkyl (in which optionally one methylene group is replaced by oxygen or sulfur) or optionally substituted phenyl, or $Q^3$ and $Q^4$ together with the carbon atom to which they are attached represent a saturated or unsaturated, unsubstituted or substituted cycle which optionally contains a heteroatom, G represents hydrogen (a) or represents one of the groups

(b)

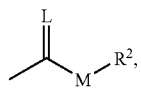
(c)

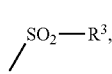
(d)

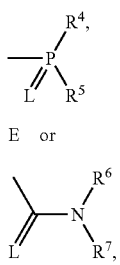

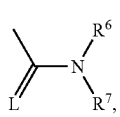

in which

E represents a metal ion equivalent or an ammonium ion,

L represents oxygen or sulfur,

M represents oxygen or sulfur, $R^1$ represents in each case optionally halogen-substituted alkyl, alkenyl, alkoxyalkyl, alylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulfur.

Depending also on the nature of the substituents, the compounds of the formula (I) can be present as geometrical and/or optical isomers or isomer mixtures of varying composition which, if appropriate, may be separated in a customary manner. The present invention provides both the pure isomers and the isomer mixtures, their preparation and use, and compositions comprising them. However, for the sake of simplicity, hereinbelow only compounds of the formula (I) are referred to, although what is meant are both the pure compounds and, if appropriate, also mixtures having varying proportions of isomeric compounds.

Including the meanings (1) to (8) of group CKE, the following principal structures (I-1) to (I-8) result:

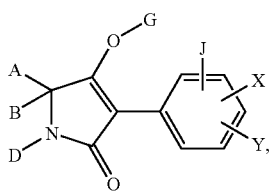

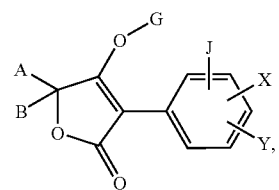

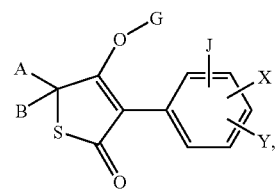

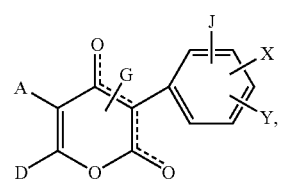

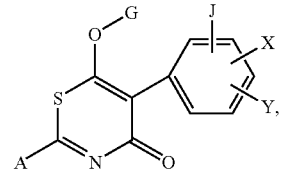

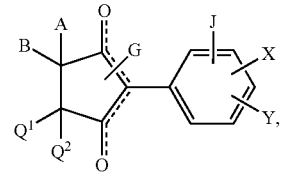

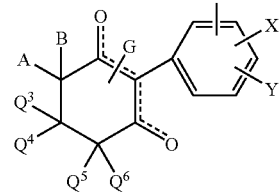

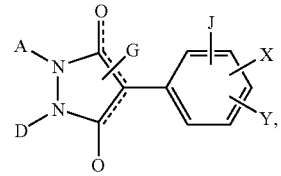

in which

A, B, D, G, J, $Q^1$, $Q^2$, $Q^3$, $Q^4$, $Q^5$, $Q^6$, X and Y are as defined above.

Including the different meanings (a), (b), (c), (d), (e), (f) and (g) of group G, the following principal structures (I-1-a) to (I-1-g) result if CKE represents group (1)

(I-1-a):
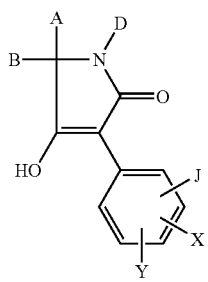
(I-1-b):
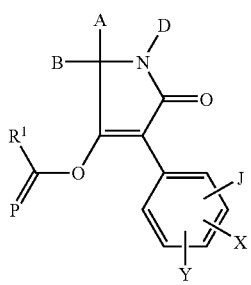
(I-1-c):
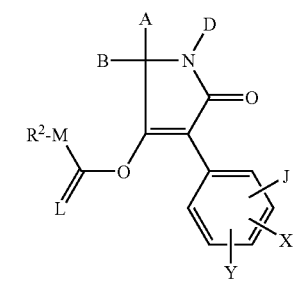
(I-1-d):
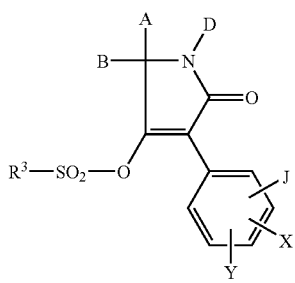
(I-1-e):
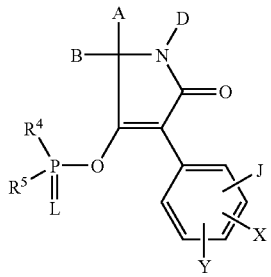
(I-1-f):
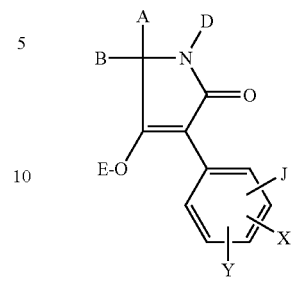
(I-1-g):
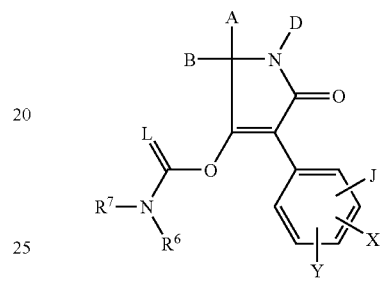
in which
A, B, D, E, J, L, M, X, Y, $R^1$, $R^2$, $R^3$, $R^4$, $R^5$, $R^6$ and $R^7$ are as defined above.
Including the different meanings (a), (b), (c), (d), (e), (f) and (g) of group G, the following principal structures (I-2-a) to (I-2-g) result if CKE represents group (2)
(I-2-a):
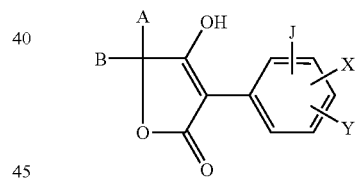
(I-2-b):
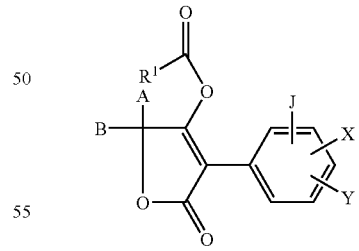
(I-2-c):
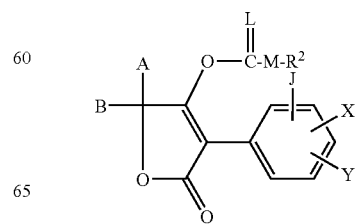

(I-2-d):

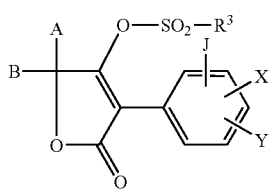

(I-2-e):

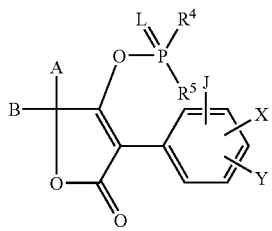

(I-2-f):

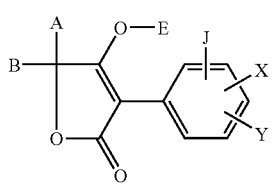

(I-2-g):

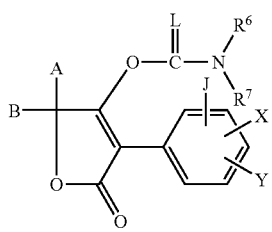

in which

A, B, E, J, L, M, X, Y, $R^1$, $R^2$, $R^3$, $R^4$, $R^5$, $R^6$ and $R^7$ are as defined above.

Including the different meanings (a), (b), (c), (d), (e), (f) and (g) of group G, the following principal structures (I-3-a) to (I-3-g) result if CKE represents group (3)

(I-3-a):

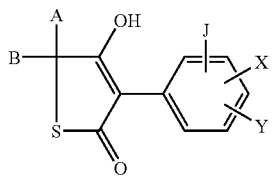

(I-3-b):

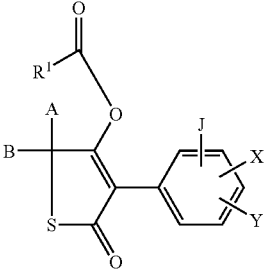

(I-3-c):

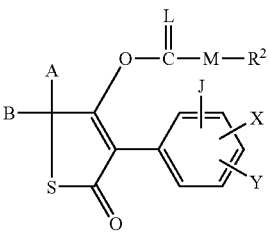

(I-3-d):

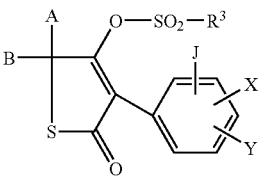

(I-3-e):

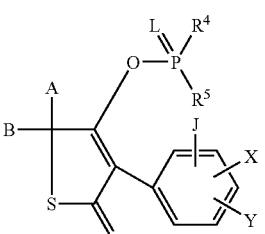

(I-3-f):

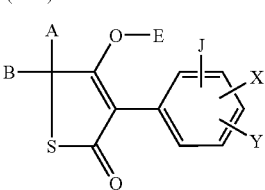

(I-3-g):

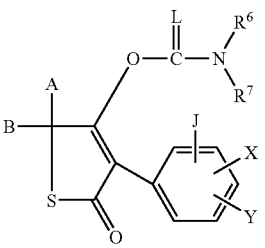

in which

A, B, E, J, L, M, X, Y, $R^1$, $R^2$, $R^3$, $R^4$, $R^5$, $R^6$ and $R^7$ are as defined above.

Depending on the position of the substituent G, the compounds of the formula (I4) can be present in the two isomeric forms of the formulae (I4-A) and (I-4-B)

(I-4-A)

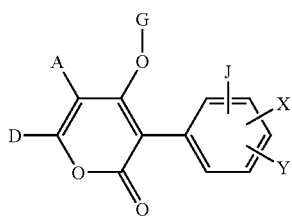

(I-4-B)

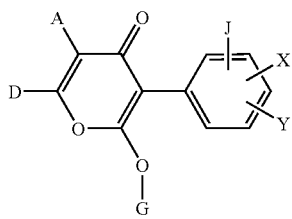

which is meant to be indicated by the dashed line in the formula (I-4).

The compounds of the formulae (I-4-A) and (I-4-B) can be present both as mixtures and in the form of their pure isomers. If appropriate, mixtures of the compounds of the formulae (I-4-A) and (I-4-B) can be separated in a manner known per se by physical methods, for example by chromatographic methods.

For reasons of clarity, hereinbelow in each case only one of the possible isomers is shown. This does not preclude that, if appropriate, the compounds may be present in the form of the isomer mixtures or the respective other isomeric forms.

Including the different meanings (a), (b), (c), (d), (e), (f) and (g) of group G, the following principal structures (I-4-a) to (I-4-g) result if CKE represents group (4)

(I-4-a):

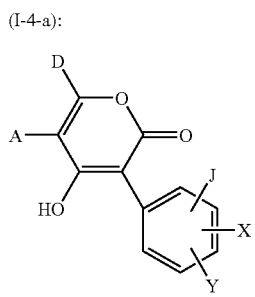

(I-4-b):

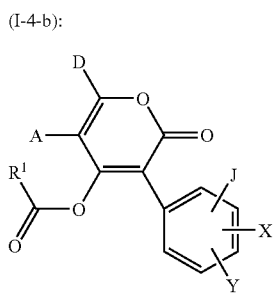

(I-4-c):

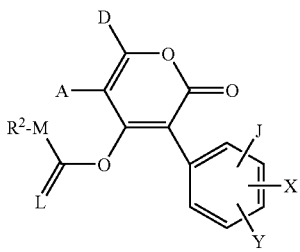

(I-4-d):

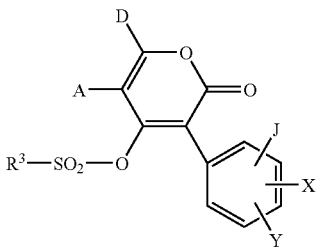

(I-4-e):

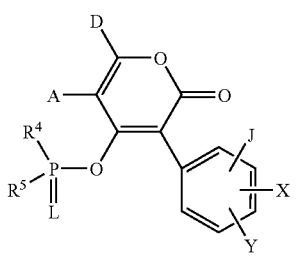

(I-4-f):

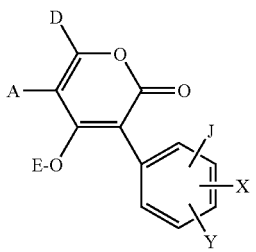

(I-4-g):

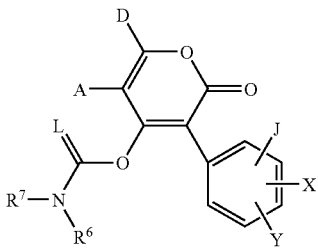

in which

A, D, E, J, L, M, X, Y, $R^1$, $R^2$, $R^3$, $R^4$, $R^5$, $R^6$ and $R^7$ are as defined above.

Including the different meanings (a), (b), (c), (d), (e), (f) and (g) of group G, the following principal structures (I-5-a) to (I-5-g) result if CKE represents group (5)

(I-5-a):
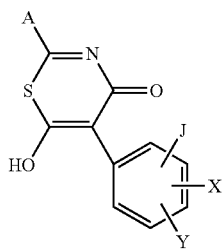

(I-5-b):
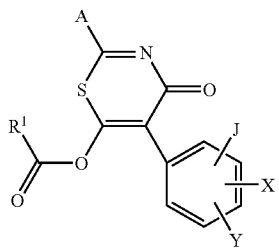

(I-5-c):
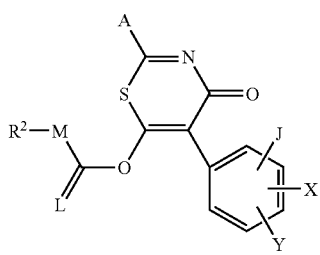

(I-5-d):
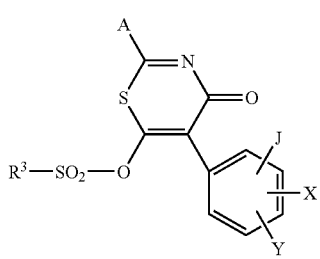

(I-5-e):
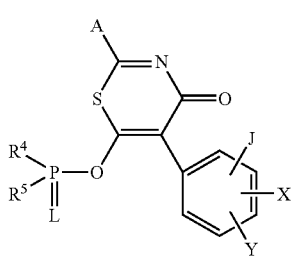

(I-5-f):
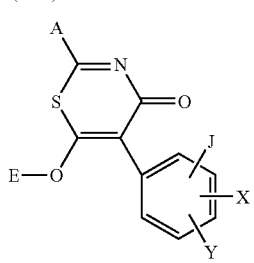

(I-5-g):
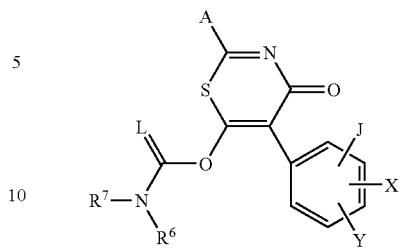

in which

A, E, J, L, M, X, Y, $R^1$, $R^2$, $R^3$, $R^4$, $R^5$, $R^6$ and $R^7$ are as defined above.

Depending on the position of the substituent G, the compounds of the formula (I-6) can be present in the two isomeric forms of the formulae (I-6-A) and (I-6-B)

(I-6-A)
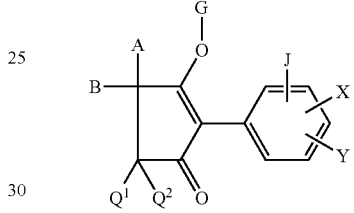

(I-6-B)
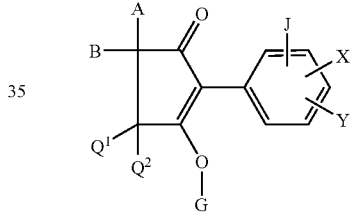

which is meant to be indicated by the dashed line in the formula (I).

The compounds of the formulae (I-6-A) and (I-6-B) can be present both as mixtures and in the form of their pure isomers. If appropriate, mixtures of the compounds of the formulae (I-6-A) and (I-6-B) can be separated by physical methods, for example by chromatographic methods.

For reasons of clarity, hereinbelow in each case only one of the possible isomers is shown. This does not preclude that, if appropriate, the compounds may be present in the form of the isomer mixtures or the respective other isomeric forms.

Including the different meanings (a), (b), (c), (d), (e), (f) and (g) of group G, the following principal structures (I-6-a) to (I-6-g) result:

(I-6-a):
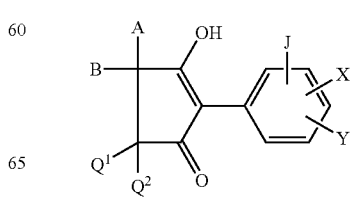

(I-6-b):

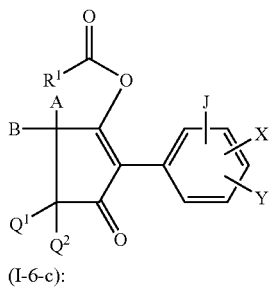

(I-6-c):

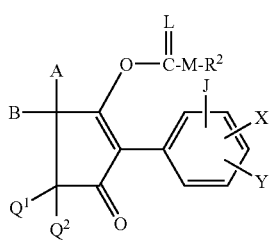

(I-6-d):

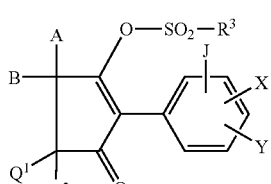

(I-6-e):

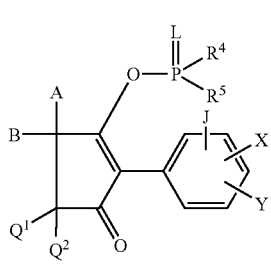

(I-6-f):

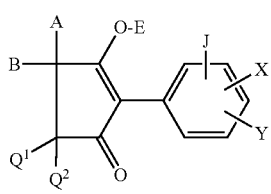

(I-6-g):

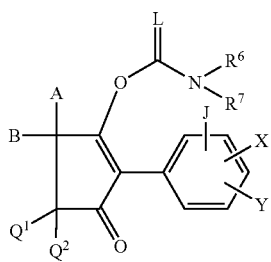

in which

A, B, J, $Q^1$, $Q^2$, E, L, M, X, Y, $R^1$, $R^2$, $R^3$, $R^4$, $R^5$, $R^6$ and $R^7$ are as defined above.

Depending on the position of the substituent G, the compounds of the formula (I-7) can be present in the two isomeric forms of the formulae (I-7-A) and (I-7-B), which is meant to be indicated by the dashed line in the formula (I-7):

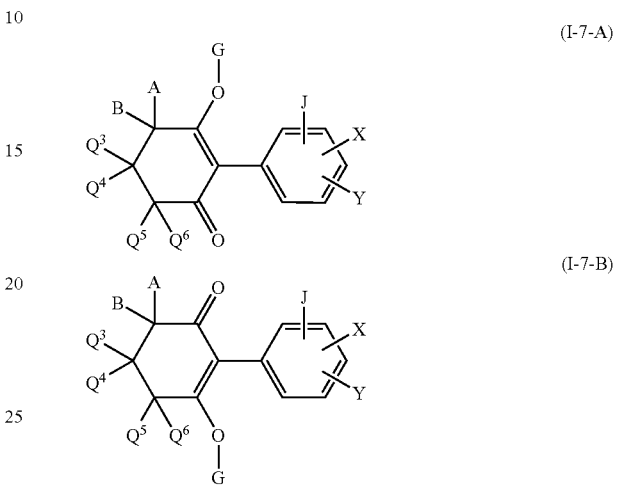

The compounds of the formulae (I-7-A) and (I-7-B) can be present both as mixtures and in the form of their pure isomers. If appropriate, mixtures of the compounds of the formulae (I-7-A) and (I-7-B) can be separated by physical methods, for example by chromatographic methods.

For reasons of clarity, hereinbelow in each case only one of the possible isomers is shown. This does not preclude that, if appropriate, the compound in question may be present in the form of the isomer mixtures or the respective other isomeric form.

Including the different meanings (a), (b), (c), (d), (e), (f) and (g) of group G, the following principal structures (I-7-a) to (I-7-g) result:

(I-7-a):

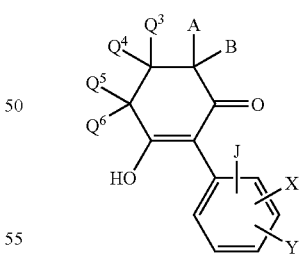

(I-7-b):

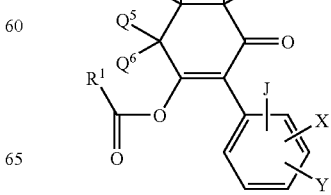

-continued (I-7-c):

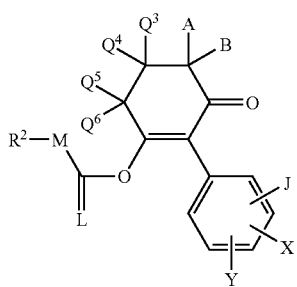

(I-7-d):

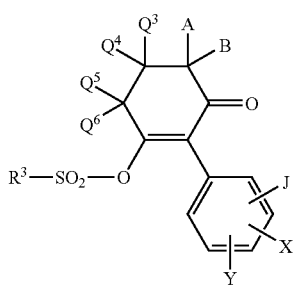

(I-7-e):

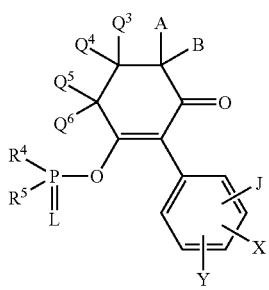

(I-7-f):

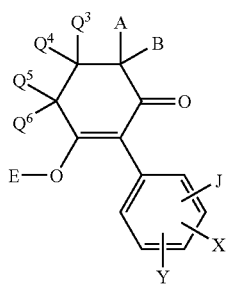

(I-7-g):

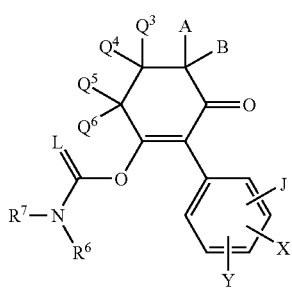

in which
A, B, J, E, L, M, $Q^3$, $Q^4$, $Q^5$, $Q^6$, X, Y, $R^1$, $R^2$, $R^3$, $R^4$, $R^5$, $R^6$ and $R^7$ are as defined above.

Depending on the position of the substituent G, the compounds of the formula (I-8) can be present in the two isomeric formulae (I-8-A) and (I-8-B)

(I-8-A)

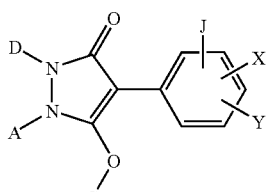

(I-8-B)

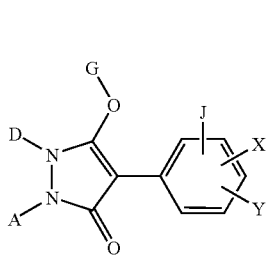

which is meant to be indicated by the dashed line in the formula (I-8).

The compounds of the formulae (I-8-A) and (I-8-B) can be present both as mixtures and in the form of their pure isomers. If appropriate, mixtures of the compounds of the formulae (I-8-A) and (I-8-B) can be separated in a manner known per se by physical methods, for example by chromatographic methods.

For reasons of clarity, hereinbelow in each case only one of the possible isomers is shown. This does not preclude that, if appropriate, the compounds may be present in the form of the isomer mixtures or the respective other isomeric forms.

Including the different meanings (a), (b), (c), (d), (e), (f) and (g) of group G, the following principal structures (I-8-a) to (I-8-g) result if Het represents the group (8)

(I-8-a):

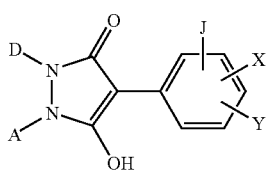

(I-8-b):

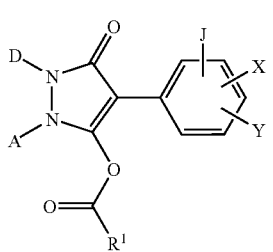

(I-8-c):

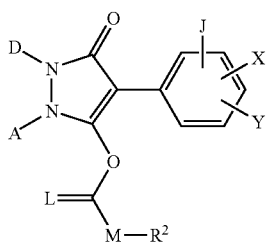

(I-8-d):

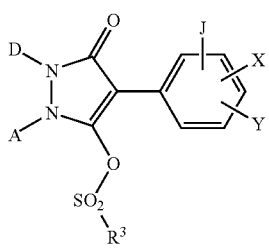

(I-8-e):

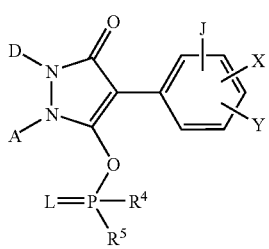

(I-8-f):

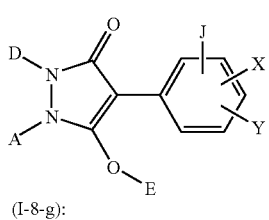

(I-8-g):

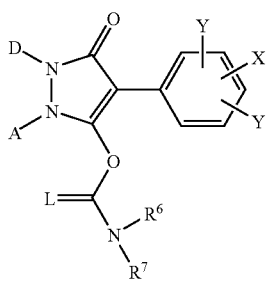

in which

A, D, E, J, L, M, X, Y, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) substituted 3-phenylpyrrolidine-2,4-diones or their enols of the formula (I-1-a)

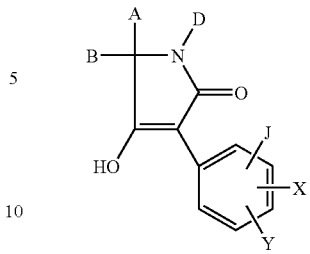
(I-1-a)

in which
A, B, D, J, X and Y are as defined above,
are obtained when
N-acylamino acid esters of the formula (II)

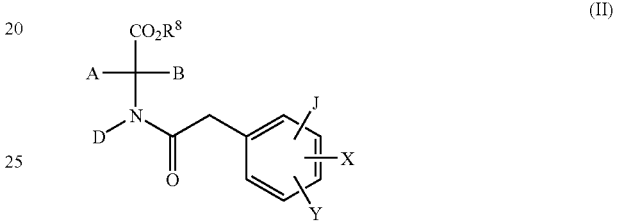
(II)

in which
A, B, D, J, X and Y are as defined above
and
$R^8$ represents alkyl (preferably $C_1$-$C_6$-alkyl)
are condensed intramolecularly in the presence of a diluent and in the presence of a base.

(B) Furthermore, it has been found that substituted 3-phenyl-4-hydroxy-$\Delta^3$-dihydrofuranone derivatives of the formula (I-2-a)

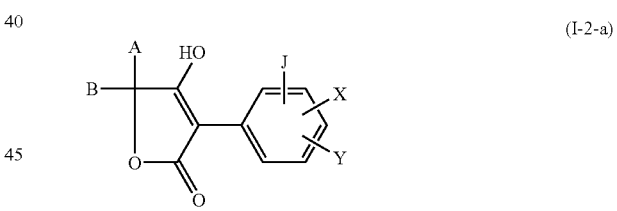
(I-2-a)

in which
A, B, J, X and Y are as defined above
are obtained when
carboxylic esters of the formula (III)

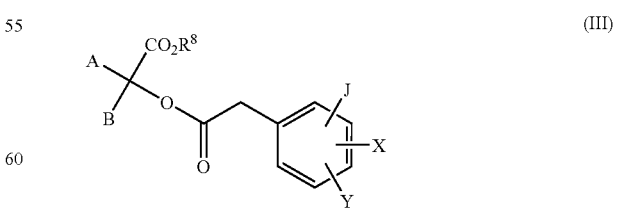
(III)

in which
A, B, J, X, Y and $R^8$ are as defined above
are condensed intramolecularly in the presence of a diluent and in the presence of a base.

(C) Furthermore, it has been found that substituted 3-phenyl-4-hydroxy-Δ³-dihydrothiophenone derivatives of the formula (I-3-a)

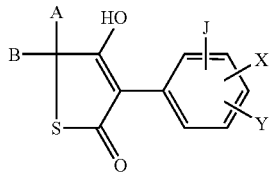
(I-3-a)

in which
A, B, J, X and Y are as defined above
are obtained when
β-ketocarboxylic esters of the formula (IV)

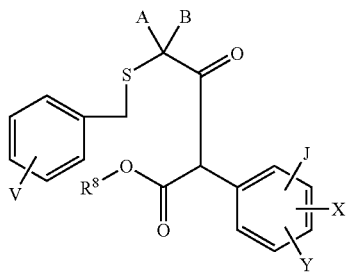
(IV)

in which
A, B, J, X, Y and $R^8$ are as defined above and
V represents hydrogen, halogen, alkyl (preferably $C_1$-$C_6$-alkyl) or alkoxy (preferably $C_1$-$C_8$-alkoxy)
are cyclized intramolecularly, if appropriate in the presence of a diluent and in the presence of an acid.

(D) Furthermore, it has been found that the novel substituted 3-phenylpyrone derivatives of the formula (I-4-a)

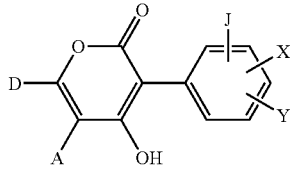
(I-4-a)

in which
A, D, J, X and Y are as defined above
are obtained when
carbonyl compounds of the formula (V)

(V)

in which
A and D are as defined above
or silylenol ethers thereof of the formula (Va)

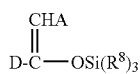
(Va)

in which
A, D and $R^8$ are as defined above
are reacted with ketene acid halides of the formula (VI)

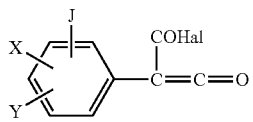
(VI)

in which
J, X and Y are as defined above and
Hal represents halogen (preferably chlorine or bromine),
if appropriate in the presence of a diluent and if appropriate in the presence of an acid acceptor.

Furthermore, it has been found
(E) that the novel substituted phenyl-1,3-thiazine derivatives of the formula (I-5-a)

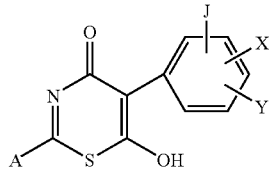
(I-5-a)

in which
A, J, X and Y are as defined above
are obtained when thioamides of the formula (VII)

(VII)

in which
A is as defined above
are reacted with ketene acid halides of the formula (VI)

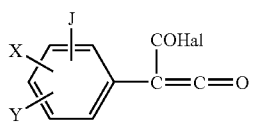
(VI)

in which
Hal, J, X and Y are as defined above,
if appropriate in the presence of a diluent and if appropriate in the presence of an acid acceptor.

Furthermore, it has been found
(F) that compounds of the formula (I-6-a)

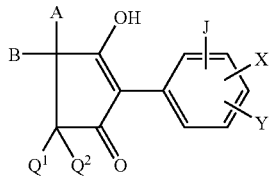
(I-6-a)

in which
A, B, $Q^1$, $Q^2$, J, X and Y are as defined above
are obtained when
ketocarboxylic esters of the formula (VIII)

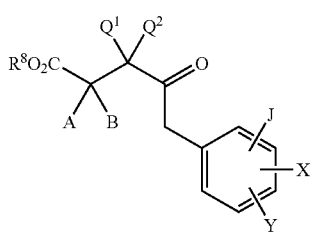
(VIII)

in which
A, B, $Q^1$, $Q^2$, J, X and Y are as defined above and
$R^8$ represents alkyl (in particular $C_1$-$C_8$-alkyl)
are cyclized intramolecularly, if appropriate in the presence of a diluent and in the presence of a base.
Moreover, it has been found
(G) that compounds of the formula (I-7-a)

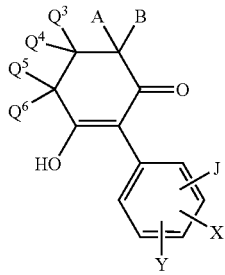
(I-7-a)

in which
A, B, J, $Q^3$, $Q^4$, $Q^5$, $Q^6$, X and Y are as defined above
are obtained when
6-aryl-5-ketohexanoic esters of the formula (IX)

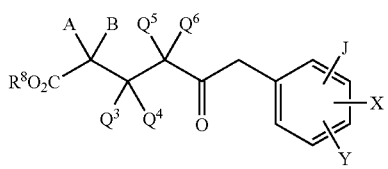
(IX)

in which
A, B, J, $Q^3$, $Q^4$, $Q^5$, $Q^6$, X and Y are as defined above and
$R^8$ represents alkyl (preferably $C_1$-$C_6$-alkyl)
are condensed intramolecularly in the presence of a diluent and in the presence of a base.
(H) Furthermore, it has been found that the compounds of the formula (I-8-a)

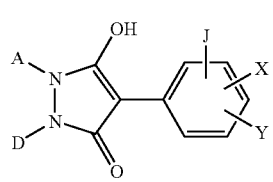
(I-8-a)

in which
A, D, J, X and Y are as defined above
are obtained when
compounds of the formula (X)

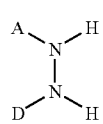
(X)

in which
A and D are as defined above
α) are reacted with compounds of the formula (VI)

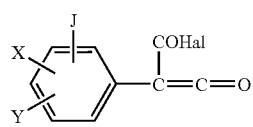
(VI)

in which
Hal, X, Y and J are as defined above,
if appropriate in the presence of a diluent and if appropriate in the presence of an acid acceptor, or
β) are reacted with compounds of the formula (XI)

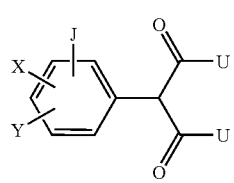
(XI)

in which
J, X and Y are as defined above
and U represents $NH_2$ or O—$R^8$, where $R^8$ is as defined above,
if appropriate in the presence of a diluent and if appropriate in the presence of a base, or γ) are reacted with compounds of the formula (XII)

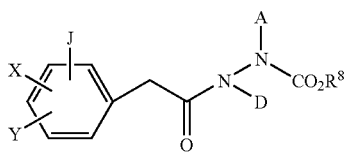
(XII)

in which
A, D, J, X, Y and $R^8$ are as defined above,
if appropriate in the presence of a diluent and if appropriate in the presence of a base.

Moreover, it has been found (I) that the compounds of the formulae (I-1-b) to (I-8-b) shown above in which A, B, D, J, $Q^1$, $Q^2$, $Q^3$, $Q^4$, $Q^5$, $Q^6$, $R^1$, X and Y are as defined above are obtained when compounds of the formulae (I-1-a) to (I-8-a) shown above in which A, B, D, J, $Q^1$, $Q^2$, $Q^3$, $Q^4$, $Q^5$, $Q^6$, X and Y are as defined above are in each case (α) reacted with acid halides of the formula (XIII)

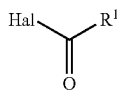
(XIII)

in which
$R^1$ is as defined above and
Hal represents halogen (in particular chlorine or bromine)
or
(β) with carboxylic anhydrides of the formula (XIV)

$$R^1\text{—CO—O—CO—}R^1 \quad (XIV)$$

in which
$R^1$ is as defined above,
if appropriate in the presence of a diluent and if appropriate in the presence of an acid binder;

(J) that the compounds of the formulae (I-1-c) to (I-8-c) shown above in which A, B, D, J, $Q^1$, $Q^2$, $Q^3$, $Q^4$, $Q^5$, $Q^6$, $R^2$, M, X and Y are as defined above and L represents oxygen are obtained when compounds of the formulae (I-1-a) to (I-8-a) shown above in which A, B, D, J, $Q^1$, $Q^2$, $Q^3$, $Q^4$, $Q^5$, $Q^6$, X and Y are as defined above are in each case
reacted with chloroformic esters or chloroformic thioesters of the formula (XV)

$$R^2\text{-M-CO—Cl} \quad (XV)$$

in which
$R^2$ and M are as defined above
if appropriate in the presence of a diluent and if appropriate in the presence of an acid binder;

(K) that compounds of the formulae (I-1-c) to (I-8-c) shown above in which A, B, D, J, $Q^1$, $Q^2$, $Q^3$, $Q^4$, $Q^5$, $Q^6$, $R^2$, M, X and Y are as defined above and L represents sulfur are obtained when compounds of the formulae (I-1-a) to (I-8-a) shown above in which A, B, D, J, $Q^1$, $Q^2$, $Q^3$, $Q^4$, $Q^5$, $Q^6$, X and Y are as defined above are in each case
reacted with chloromonothioformic esters or chlorodithioformic esters of the formula (XVI)

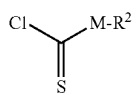
(XVI)

in which
M and $R^2$ are as defined above,
if appropriate in the presence of a diluent and if appropriate in the presence of an acid binder,
and (L) that compounds of the formulae (I-1-d) to (I-8-d) shown above in which A, B, D, J, $Q^1$, $Q^2$, $Q^3$, $Q^4$, $Q^5$, $Q^6$, $R^3$, X and Y are as defined above are obtained when compounds of the formulae (I-1-a) to (I-8-a) shown above in which A, B, D, J, $Q^1$, $Q^2$, $Q^3$, $Q^4$, $Q^5$, $Q^6$, X and Y are as defined above are in each case
reacted with sulfonyl chlorides of the formula (XVII)

$$R^3\text{—SO}_2\text{—Cl} \quad (XVII)$$

in which
$R^3$ is as defined above,
if appropriate in the presence of a diluent and if appropriate in the presence of an acid binder, (M) that compounds of the formulae (I-1-e) to (I-8-e) shown above in which A, B, D, J, L, $Q^1$, $Q^2$, $Q^3$, $Q^4$, $Q^5$, $Q^6$, $R^4$, $R^5$, X and Y are as defined above are obtained when compounds of the formulae (I-1-a) to (I-8-a) shown above in which A, B, D, J, $Q^1$, $Q^2$, $Q^3$, $Q^4$, $Q^5$, $Q^6$, X and Y are as defined above are in each case reacted with phosphorus compounds of the formula (XVIII)

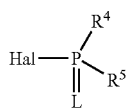
(XVIII)

in which
L, $R^4$ and $R^5$ are as defined above and
Hal represents halogen (in particular chlorine or bromine),
if appropriate in the presence of a diluent and if appropriate in the presence of an acid binder, (N) that compounds of the formulae (I-1-f) to (I-8-f) shown above in which A, B, D, E, J, $Q^1$, $Q^2$, $Q^3$, $Q^4$, $Q^5$, $Q^6$, X and Y are as defined above are obtained when compounds of the formulae (I-1-a) to (I-8-a) in which A, B, D, J, $Q^1$, $Q^2$, $Q^3$, $Q^4$, $Q^5$, $Q^6$, X and Y are as defined above are in each case
reacted with metal compounds or amines of the formulae (XIX) or (XX)

$$\text{Me(OR}^{10}\text{)}_t \quad (XIX)$$

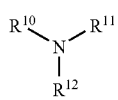
(XX)

in which
Me represents a mono- or divalent metal (preferably an alkali metal or alkaline earth metal, such as lithium, sodium, potassium, magnesium or calcium), or represents an ammonium ion

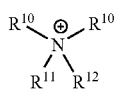

t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (O) that compounds of the formulae (I-1-g) to (I-8-g) shown above in which A, B, D, J, L, $Q^1$, $Q^2$, $Q^3$, $Q^4$, $Q^5$, $Q^6$, $R^6$, $R^7$, X and Y are as defined above are obtained when compounds of the formulae (I-1-a) to (I-8-a) shown above in which A, B, D, J, $Q^1$, $Q^2$, $Q^3$, $Q^4$, $Q^5$, $Q^6$, X and Y are as defined above are in each case (α) reacted with isocyanates or isothiocyanates of the formula (XXI)

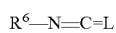

(XXI)

in which $R^6$ and L are as defined above, if appropriate in the presence of a diluent and if appropriate in the presence of a catalyst, or (β) reacted with carbamoyl chlorides or thiocarbamoyl chlorides of the formula (XXII)

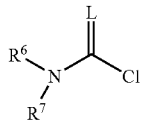

(XXII)

in which

L, $R^6$ and $R^7$ are as defined above, if appropriate in the presence of a diluent and if appropriate in the presence of an acid binder, (P) that compounds of the formulae (I-1-a) to (I-8-a) shown above in which A, B, D, J, $Q^1$, $Q^2$, $Q^3$, $Q^4$, $Q^5$, $Q^6$, X and Y are as defined above are obtained when compounds of the formulae (I-1-a') to (I-8-a') in which A, B, D, $Q^1$, $Q^2$, $Q^3$, $Q^4$, $Q^5$, $Q^6$, X and Y are as defined above and W' preferably represents bromine (I-1-a')

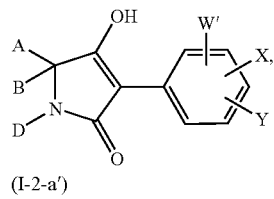

(I-2-a')

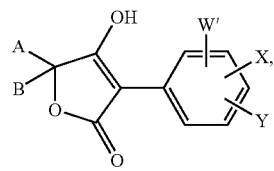

(I-3-a')

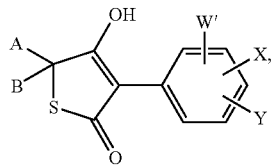

(I-4-a')

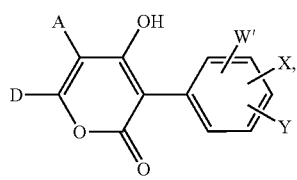

(I-5-a')

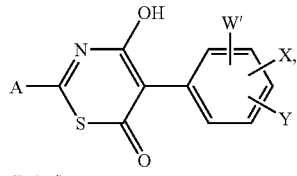

(I-6-a')

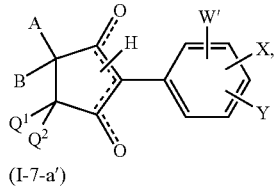

(I-7-a')

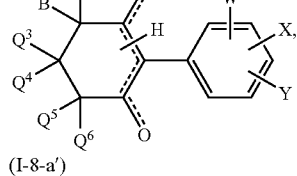

(I-8-a')

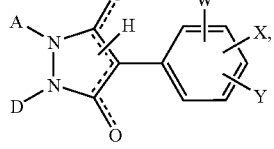

α) are reacted with metal iodides (for example sodium iodide or potassium iodide), if appropriate in the presence of a diluent, a Cu(I) salt (for example CuBr, CuI) and a base (for example N,N-dimethylethylenediamine), or β) subjected to a halogen/metal exchange with metal organyls (for example n, s-, -butyllithium) and the anion formed is quenched with iodinating agents (for example iodine, iodine monochloride).

Furthermore, it has been found that the novel compounds of the formula (I) have good activity as pesticides, preferably as insecticides, acaricides and/or herbicides.

Surprisingly, it has now also been found that certain substituted cyclic ketoenols, when employed together with the crop plant compatibility-improving compounds (safeners/antidotes) described later on, are extremely good at preventing damage to the crop plants and can be used with particular advantage as broad-spectrum combination products for the selective control of unwanted plants in crops of useful plants, such as, for example, in cereals, but also in corn, soya beans and rice.

The invention also provides selective herbicidal compositions comprising an effective amount of an active compound combination comprising, as components, (a') at least one substituted cyclic ketoenol of the formula (I) in which CKE, J, X and Y are as defined above and (b') at least one crop plant compatibility-improving compound from the following group of compounds:
4-dichloroacetyl-1-oxa-4-azaspiro[4.5]decane (AD-67, MON4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine(benoxacor), 1-methylhexyl 5-chloroquinoline-8-oxy-acetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile(cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N, N-di-2-propenylacetamide (dichlormid), 4,6-dichloro-2-phenylpyrimidine(fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate(flurazole), 4-chloro-N-(1,3-dioxolan-2-ylmethoxy)-α-trifluoroacetophenone oxime(fluxofenim), 3-dichloroacetyl-5-(2-furanyl)-2,2-dimethyloxazolidine(furilazole, MON-13900), ethyl 4,5-dihydro-5,5-diphenyl-3-isoxazolecarboxylate(isoxadifenethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichorophenyl)-4,5-dihydro-5-methyl-1H-pyrazole-3,5-dicarboxylate (mefenpyrdiethyl—cf. also related compounds in WO-A-91/07874), 2-dichloromethyl-2-methyl-1,3-dioxolane (MG-191), 2-propenyl-1-oxa-4-azaspiro[4.5] decane-4-carbodithioate (MG-838), 1,8-naphthalic anhydride, α-(1,3-dioxolan-2-ylmethoximino)phenylacetonitrile(oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulfonylbenzene, 1-[4-(N-2-methoxybenzoylsulfamoyl)-phenyl]-3-methylurea (also known as N-(2-methoxybenzoyl)-4-[(methylaminocarbonyl)-amino]benzenesulfonamide), 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, N-(2-methoxy-5-methylbenzoyl)-4-(cyclopropylaminocarbonyl)-benzenesulfonamide, and/or one of the following compounds, defined by general formulae, of the general formula (IIa)

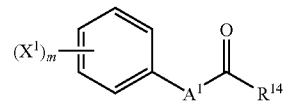

or of the general formula (IIb)

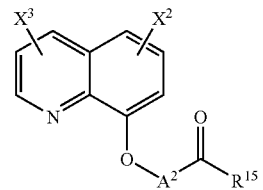

or of the formula (IIc)

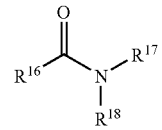

where
m represents a number 0, 1, 2, 3, 4 or 5,
$A^1$ represents one of the divalent heterocyclic groupings shown below

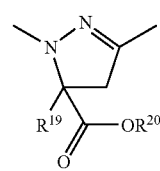 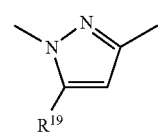 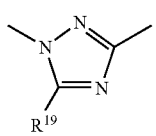

-continued

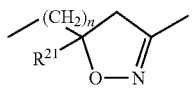

n represents a number 0, 1, 2, 3, 4 or 5, $A^2$ represents optionally $C_1$-$C_4$-alkyl- and/or $C_1$-$C_4$-alkoxy-carbonyl- and/or $C_1$-$C_4$-alkenyloxy-carbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)-amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino, $R^{16}$ represents in each case optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae, of the general formula (IId)

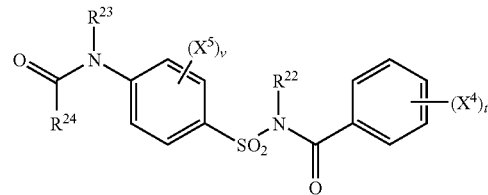

(IId)

or of the general formula (IIe)

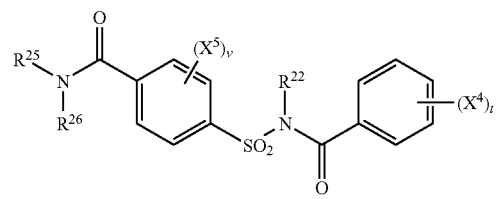

(IIe)

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae given above and below are illustrated below:

J preferably represents iodine,

X preferably represents hydrogen, halogen, $C_1$-$C_6$-alkyl, $C_1$-$C_4$-haloalkyl, $C_1$-$C_6$-alkoxy or $C_1$-$C_4$-haloalkoxy, Y preferably represents hydrogen, $C_1$-$C_6$-alkyl, halogen or $C_1$-$C_6$-alkoxy, with the proviso that at least one of the radicals J, X or Y is located in the 2-position of the phenyl radical and is not hydrogen, CKE preferably represents one of the groups

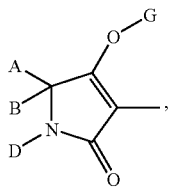 (1)

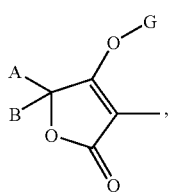 (2)

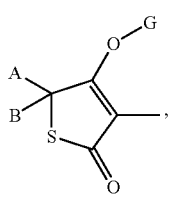 (3)

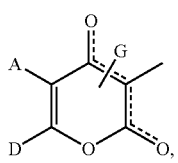 (4)

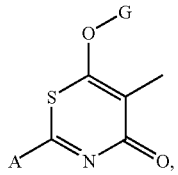 (5)

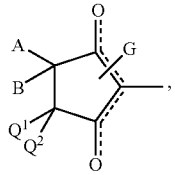 (6)

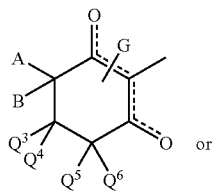 (7) or

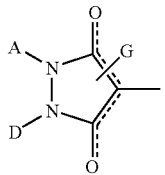 (8)

A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulfur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, B preferably represents hydrogen, $C_1$-$C_{12}$-alkyl or $C_1$-$C_8$-alkoxy-$C_1$-$C_6$-alkyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulfur and which are optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_4$-alkoxy-$C_1$-$C_4$-alkoxy, $C_1$-$C_8$-alkylthio, halogen or phenyl or A, B and the carbon atom to which they are attached preferably represent $C_3$-$C_6$-cycloalkyl which is substituted by an alkylenedithioyl group or by an alkylenedioxyl group or by an alkylenediyl group which optionally contains one or two not directly adjacent oxygen and/or sulfur atoms and which is optionally substituted by $C_1$-$C_4$-alkyl, which group, together with the carbon atom to which it is attached, forms a further five- to eight-membered ring, or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulfur, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulfur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms atoms (for example furanyl, imidazolyl, pyridyl, thiazolyl, pyrazolyl, pyrimidyl, pyrrolyl, thienyl or or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or or triazolyl) or A and D together preferably represent in each case optionally substituted $C_3$-$C_6$-alkanediyl or $C_3$-$C_6$-alkenediyl in which optionally one methylene group is replaced by a carbonyl group, oxygen or sulfur, possible substituents being in each case:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compound of the formula (I-1) A and D in this case together with the atoms to which they are attached represent, for example, the groups AD-1 to AD-10 mentioned further below) that may contain oxygen or sulfur or which optionally contains one of the following groups

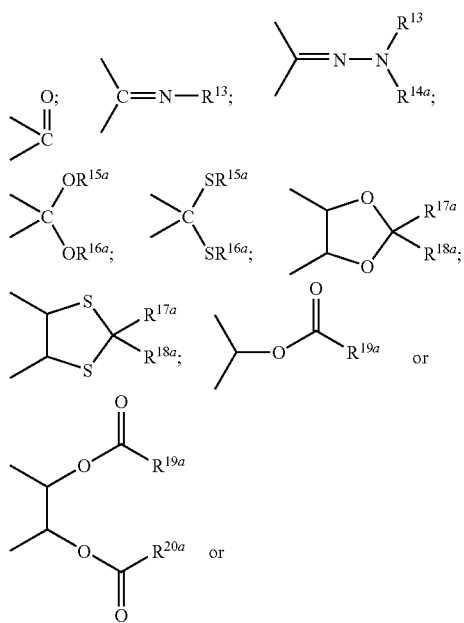

A and $Q^1$ together preferably represent $C_3$-$C_6$-alkanediyl or $C_4$-$C_6$-alkenediyl, each of which is optionally mono- or disubstituted by identical or different substituents from the group consisting of halogen; hydroxyl; $C_1$-$C_{10}$-alkyl, $C_1$-$C_6$-alkoxy, $C_1$-$C_6$-alkylthio, $C_3$-$C_7$-cycloalkyl, each of which is optionally mono- to trisubstituted by identical or different halogen substituents; and benzyloxy or phenyl, each of which is optionally mono- to trisubstituted by identical or different substituents from the group consisting of halogen, $C_1$-$C_6$-alkyl and $C_1$-$C_6$-alkoxy; which $C_3$-$C_6$-alkanediyl or $C_4$-$C_6$-alkenediyl furthermore optionally contains one of the groups below

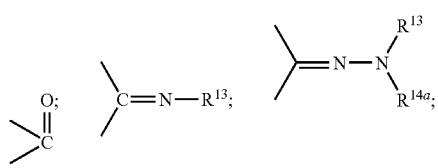

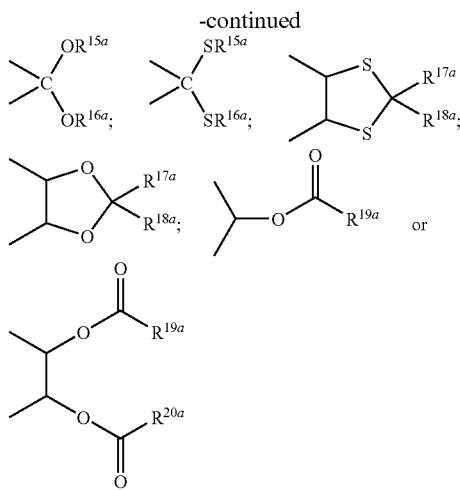

or is bridged by a $C_1$-$C_2$-alkanediyl group or by an oxygen atom or $Q^1$ preferably represents hydrogen or $C_1$-$C_4$-alkyl, $Q^2$, $Q^4$, $Q^5$ and $Q^6$ independently of one another preferably represent hydrogen or $C_1$-$C_4$-alkyl, $Q^3$ preferably represents hydrogen, $C_1$-$C_6$-alkyl, $C_1$-$C_6$-alkoxy-$C_1$-$C_2$-alkyl, $C_1$-$C_6$-alkylthio-$C_1$-$C_2$-alkyl, optionally $C_1$-$C_4$-alkyl- or $C_1$-$C_4$-alkoxy-substituted $C_3$-$C_8$-cycloalkyl in which optionally one methylene group is replaced by oxygen or sulfur or optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, or $Q^3$ and $Q^4$ together with the carbon atom to which they are attached preferably represent an optionally $C_1$-$C_4$-alkyl-, $C_1$-$C_4$-alkoxy- or $C_1$-$C_2$-haloalkyl-substituted $C_3$-$C_7$-ring in which optionally one ring member is replaced by oxygen or sulfur, G preferably represents hydrogen (a) or represents one of the groups (b)
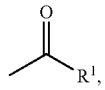

(c)
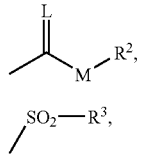

(d)

(e)
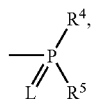

(f)
E or (g)
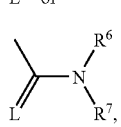

in particular (a), (b), (c) or (g)

in which
E represents a metal ion equivalent or an ammonium ion,
L represents oxygen or sulfur and
M represents oxygen or sulfur.

$R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulfur, preferably represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl, preferably represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, preferably represents optionally halogen- or $C_1$-$C_6$-alkyl-substituted 5- or 6-membered hetaryl (for example pyrazolyl, thiazolyl, pyridyl, pyrimidyl, furanyl or thienyl), preferably represents optionally halogen- or $C_1$-$C_6$-alkyl-substituted phenoxy-$C_1$-$C_6$-alkyl or preferably represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, preferably represents optionally halogen-, $C_1$-$C_6$-alkyl- or $C_1$-$C_6$-alkoxy-substituted $C_3$-$C_8$-cycloalkyl or preferably represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulfur, $R^{13}$ preferably represents hydrogen, preferably represents in each case optionally halogen-substituted $C_1$-$C_8$-alkyl or $C_1$-$C_8$-alkoxy, preferably represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulfur, or preferably represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl or phenyl-$C_1$-$C_4$-alkoxy, $R^{14a}$ preferably represents hydrogen or $C_1$-$C_8$-alkyl, or $R^{13}$ and $R^{14a}$ together preferably represent $C_4$-$C_6$-alkanediyl, $R^{15a}$ and $R^{16a}$ are identical or different and preferably represent $C_1$-$C_6$-alkyl, or $R^{15a}$ and $R^{16a}$ together preferably represent a $C_2$-$C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, or $R^{17a}$ and $R^{18a}$ together with the carbon atom to which they are attached preferably represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulfur, $R^{19a}$ and $R^{20a}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions mentioned as being preferred, halogen represents fluorine, chlorine, bromine and iodine, and in particular fluorine, chlorine and bromine.

J particularly preferably represents iodine, x particularly preferably represents hydrogen, fluorine, chlorine, bromine, iodine, $C_1$-$C_4$-alkyl, trifluoromethyl, $C_1$-$C_4$-alkoxy, difluoromethoxy or trifluoromethoxy, Y particularly preferably represents hydrogen, fluorine, chlorine, bromine, iodine, $C_1$-$C_4$-alkyl or $C_1$-$C_4$-alkoxy, with the proviso that at least one of the radicals J, X or Y is located in the 2-position of the phenyl radical and is not hydrogen.

Here, the radicals J, X and Y, having their particularly preferred meanings, are particularly preferably present in the following phenyl substitution patterns

(A)

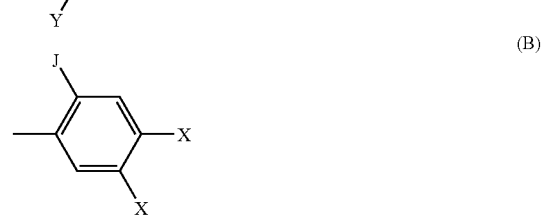

(B)

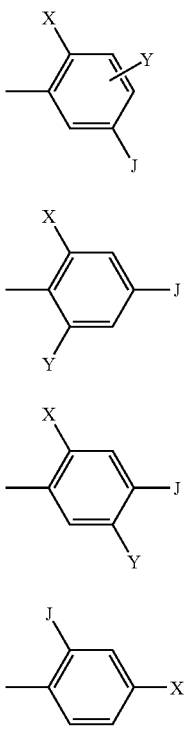

where only in the phenyl substitution patterns (A) and (G) X may also represent hydrogen.

CKE particularly preferably represents one of the groups

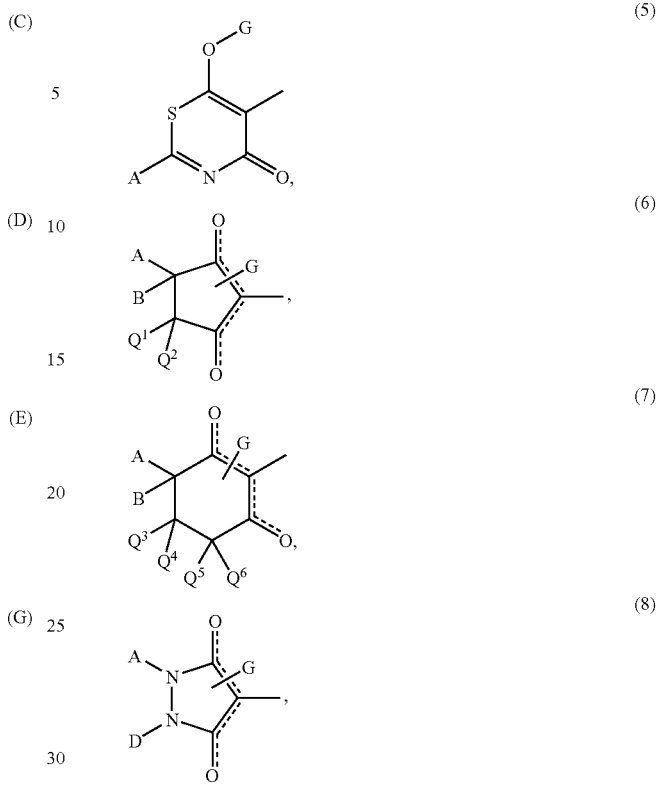

A particularly preferably represents hydrogen, represents $C_1$-$C_6$-alkyl or $C_1$-$C_4$-alkoxy-$C_1$-$C_2$-alkyl, each of which is optionally mono- to trisubstituted by fluorine or chlorine, represents $C_3$-$C_6$-cycloalkyl which is optionally mono- to disubstituted by $C_1$-$C_2$-alkyl or $C_1$-$C_2$-alkoxy or (but not in the case of the compounds of the formulae (I-3), (I-4), (I-6) and (I-7)) represents phenyl or benzyl, each of which is optionally mono- to disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B particularly preferably represents hydrogen, $C_1$-$C_4$-alkyl or $C_1$-$C_2$-alkoxyl-$C_1$-$C_2$-alkyl, or A, B and the carbon atom to which they are attached particularly preferably represent saturated or unsaturated $C_5$-$C_7$-cycloalkyl in which optionally one ring member is replaced by oxygen or sulfur and which is optionally mono- to disubstituted by $C_1$-$C_6$-alkyl, trifluoromethyl, $C_1$-$C_6$-alkoxy or $C_1$-$C_3$-alkoxy-$C_1$-$C_3$-alkoxy, with the proviso that in this case $Q^3$ particularly preferably represents hydrogen or methyl, or A, B and the carbon atom to which they are attached particularly preferably represent $C_5$-$C_6$-cycloalkyl which is substituted by an alkylenedithiol group or by an alkylenedioxyl group or by an alkylenediyl group which optionally contains one or two not directly adjacent oxygen or sulfur atoms and which is optionally substituted by methyl or ethyl, which group together with the carbon atom to which it is attached forms a further five- or six-membered ring, with the proviso that $Q^3$ in this case particularly preferably represents hydrogen or methyl, A, B and the carbon atom to which they are attached particularly preferably represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, with the proviso that $Q^3$ in this case represents hydrogen or methyl, D particularly preferably represents hydrogen, particularly preferably represents $C_1$-$C_6$-alkyl, $C_3$-$C_6$-alkenyl, $C_1$-$C_4$-alkoxy-$C_2$-$C_3$-alkyl, each of which is optionally mono- to trisubstituted by fluorine, particularly preferably represents $C_3$-$C_6$-cycloalkyl which is optionally mono- to disubstituted by $C_1$-$C_4$-alkyl, $C_1$-$C_4$-alkoxy or $C_1$-$C_2$-haloalkyl and in which optionally one methylene group is replaced by oxygen or (but not in the case of the compounds of the formulae (I-1)) represents phenyl or pyridyl, each of which is optionally mono- to disubstituted by fluorine, chlorine, bromine, $C_1$-$C_4$-alkyl, $C_1$-$C_4$-haloalkyl, $C_1$-$C_4$-alkoxy or $C_1$-$C_4$-haloalkoxy, or A and D together particularly preferably represent optionally mono- to disubstituted $C_3$-$C_5$-alkanediyl in which one methylene group may be replaced by a carbonyl group (but not in the case of the compounds of the formula (I-1)), oxgen or sulfur, possible substituents being $C_1$-$C_2$-alkyl or $C_1$-$C_2$-alkoxy, or A and D (in the case of the compounds of the formula (I-1)) together with the atoms to which they are attached represent one of the groups AD-1 to AD-10:

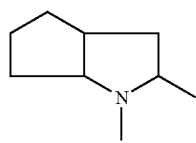 AD-1

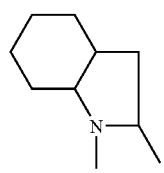 AD-2

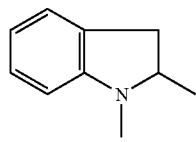 AD-3

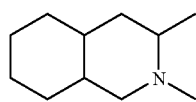 AD-4

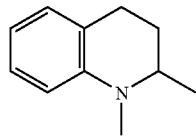 AD-5

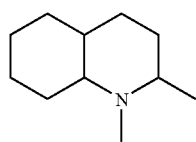 AD-6

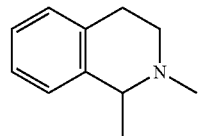 AD-7

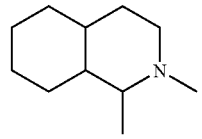 AD-8

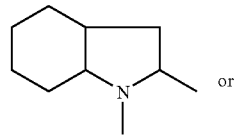 or AD-9

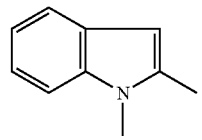 AD-10

A and $Q^1$ together particularly preferably represent $C_3$-$C_4$-alkanediyl which is in each case optionally mono- or disubstituted by identical or different substituents selected from the group consisting of $C_1$-$C_2$-alkyl and $C_1$-$C_2$-alkoxy, or $Q^1$ particularly preferably represents hydrogen, $Q^2$ particularly preferably represents hydrogen, $Q^4$, $Q^5$ and $Q^6$ independently of one another particularly preferably represent hydrogen or $C_1$-$C_3$-alkyl, $Q^3$ particularly preferably represents hydrogen, $C_1$-$C_4$-alkyl, or $C_3$-$C_6$-cycloalkyl which is optionally mono- to disubstituted by methyl or methoxy, or $Q^3$ and $Q^4$ together with the carbon to which they are attached particularly preferably represent an optionally $C_1$-$C_2$-alkyl- or $C_1$-$C_2$-alkoxy-substituted saturated $C_5$-$C_6$-ring in which optionally one ring member is replaced by oxygen or sulfur, with the proviso that in this case A particularly preferably represents hydrogen or methyl, G particularly preferably represents hydrogen (a) or represents one of the groups

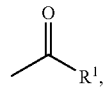 (b)

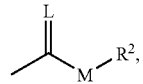 (c)

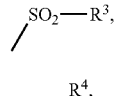 (d)

 (e)

E or (f)

-continued

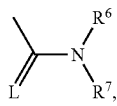
(g)

in particular (a), (b), or (c),
in which
E represents a metal ion equivalent or an ammonium ion,
L represents oxygen or sulfur and
M represents oxygen or sulfur,
$R^1$ particularly preferably represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or $C_3$-$C_6$-cycloalkyl which is optionally mono- to disubstituted by fluorine, chlorine, $C_1$-$C_2$-alkyl or $C_1$-$C_2$-alkoxy and in which optionally one or two not directly adjacent ring members are replaced by oxygen,
particularly preferably represents phenyl which is optionally mono- to disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy,
$R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine,
particularly preferably represents $C_3$-$C_6$-cycloalkyl which is optionally monosubstituted by $C_1$-$C_2$-alkyl or $C_1$-$C_2$-alkoxy or
particularly preferably represents phenyl or benzyl, each of which is optionally mono- to disubstituted by fluorine, chlorine, bromine, cyano, nitro, $C_1$-$C_4$-alkyl, $C_1$-$C_3$-alkoxy, trifluoromethyl or trifluoromethoxy,
$R^3$ particularly preferably represents $C_1$-$C_6$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro,
$R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl,
$R^5$ particularly preferably represents $C_1$-$C_6$-alkoxy or $C_1$-$C_6$-alkylthio,
$R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy,
$R^7$ particularly preferably represents $C_1$-$C_6$-alkyl, $C_3$-$C_6$-alkenyl or $C_1$-$C_6$-alkoxy-$C_1$-$C_4$-alkyl,
$R^6$ and $R^7$ together particularly preferably represent an optionally methyl- or ethyl-substituted $C_4$-$C_5$-alkylene radical in which optionally one methylene group is replaced by oxygen or sulfur.
In the radical definitions mentioned as being particularly preferred, halogen represents fluorine, chlorine and bromine, in particular fluorine and chlorine.

J very particularly preferably represents iodine,
X very particularly preferably represents hydrogen, fluorine, chlorine, bromine, methyl, ethyl, propyl, methoxy or ethoxy,
Y very particularly preferably represents hydrogen, chlorine, bromine, methyl, ethyl, propyl, methoxy or ethoxy,
with the proviso that at least one of the radicals J, X or Y is located in the 2-position of the phenyl radical and is not hydrogen.

Here, the radicals J, X and Y, having their very particularly preferred meanings, are very particularly preferably present in the following phenyl substitution patterns

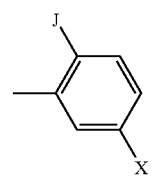
(F)

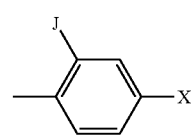
(G)

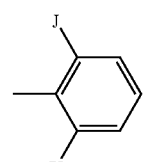
(H)

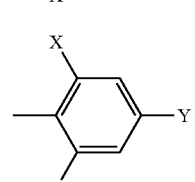
(I)

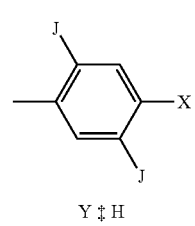
(J)

Y ‡ H

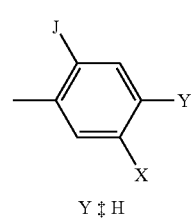
(K)

Y ‡ H

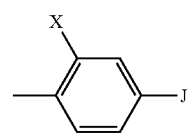
(L)

-continued

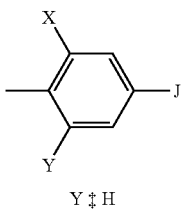
(M)

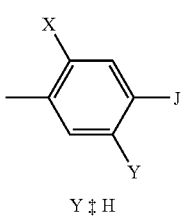
(N)

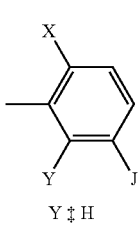
(O)

where only in the phenyl substitution pattern (G) X may also represent hydrogen.

CKE very particularly preferably represents one of the groups

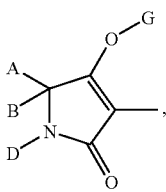
(1)

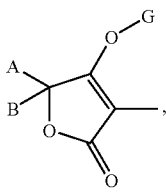
(2)

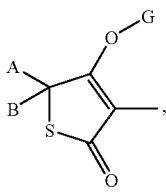
(3)

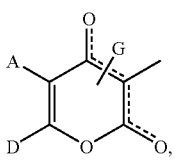
(4)

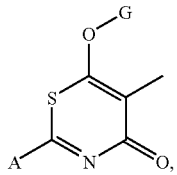
(5)

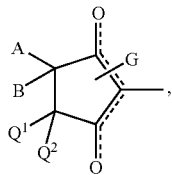
(6)

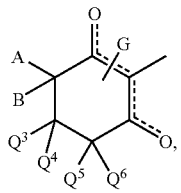
(7)

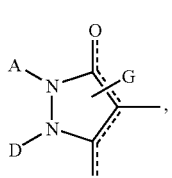
(8)

A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl and, only in the case of the compounds of the formula (I-5), represents phenyl which is optionally mono- to disubstituted by fluorine, chlorine, bromine, methyl, ethyl, n-propyl, isopropyl, methoxy, ethoxy, trifluoromethyl, trifluoromethoxy, cyano or nitro, B very particularly preferably represents hydrogen, methyl or ethyl, or A, B and the carbon atom to which they are attached very particularly preferably represent saturated $C_5$-$C_6$-cycloalkyl in which optionally one ring member is replaced by oxygen or sulfur and which is optionally monosubstituted by methyl, ethyl, propyl, isopropyl, trifluoromethyl, methoxy, ethoxy, propoxy, methoxyethoxy, butoxy or ethoxyethoxy, with the proviso that in this case $Q^3$ very particularly preferably represents hydrogen, or A, B and the carbon atom to which they are attached very particularly preferably represent $C_6$-cycloalkyl which is optionally substituted by alkylenedioxyl group which contains with two not directly adjacent oxygen atoms, with the proviso that in this case $Q^3$ very particularly preferably represents hydrogen, or A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienyl, with the proviso that in this case $Q^3$ very particularly preferably represents hydrogen, D very particularly preferably represents hydrogen, represents $C_1-C_4$-alkyl, $C_3-C_4$-alkenyl, $C_1-C_4$-alkoxy-$C_2-C_3$-alkyl, each of which is optionally mono- to trisubstituted by fluorine, represents cyclopropyl, cyclopentyl or cyclohexyl or (but not in the case of the compounds of the formulae (I-1)) represents phenyl or pyridyl, each of which is optionally monosubstituted by fluorine, chlorine, methyl, ethyl, n-propyl, isopropyl, methoxy, ethoxy or trifluoromethyl, or A and D together very particularly preferably represent $C_3-C_5$-alkanediyl which is optionally monosubstituted by methyl or methoxy and in which optionally one carbon atom is replaced by oxygen or sulfur or represent the group AD-1, A and $Q^1$ together very particularly preferably represent $C_3-C_4$-alkanediyl which is optionally mono- or disubstituted by methyl or methoxy, or $Q^1$ very particularly preferably represents hydrogen, $Q^2$ very particularly preferably represents hydrogen, $Q^4$, $Q^5$ and $Q^6$ independently of one another very particularly preferably represent hydrogen or methyl, $Q^3$ very particularly preferably represents hydrogen, methyl, ethyl or propyl, or $Q^3$ and $Q^4$ together with the carbon to which they are attached very particularly preferably represent a saturated $C_5-C_6$-ring which is optionally monosubstituted by methyl or methoxy, with the proviso that in this case A very particularly preferably represents hydrogen, G very particularly preferably represents hydrogen (a) or represents one of the groups

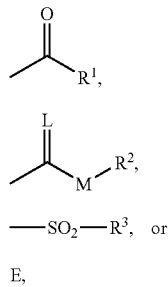

in which
L represents oxygen or sulfur,
M represents oxygen or sulfur and
E represents an ammonium ion,
$R^1$ very particularly preferably represents $C_1-C_6$-alkyl, $C_2-C_{17}$-alkenyl, $C_1-C_2$-alkoxy-$C_1$-alkyl, $C_1-C_2$-alkylthio-$C_1$-alkyl, each of which is optionally monosubstituted by chlorine, or represents cyclopropyl or cyclohexyl, each of which is optionally monosubstituted by fluorine, chlorine, methyl or methoxy,
very particularly preferably represents phenyl which is optionally monosubstituted by fluorine, chlorine, bromine, cyano, nitro, methyl, methoxy, trifluoromethyl or trifluoromethoxy,
$R^2$ very particularly preferably represents $C_1-C_8$-alkyl, $C_2-C_6$-alkenyl or $C_1-C_4$-alkoxy-$C_2-C_3$-alkyl, each of which is optionally monosubstituted by fluorine, or represents phenyl or benzyl,
$R^3$ very particularly preferably represents $C_1-C_8$-alkyl.
J especially preferably represents iodine, X especially preferably represents hydrogen, chlorine, methyl or ethyl,
Y especially preferably represents hydrogen, chlorine, methyl or ethyl, with the proviso that at least one of the radicals J, X or Y is located in the 2-position of the phenyl radical and is not hydrogen.

Here, the radicals J, X and Y, having their especially preferred meanings, are especially preferably present in the following phenyl substitution patterns

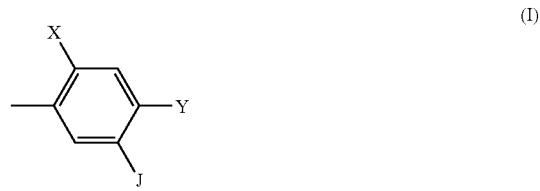

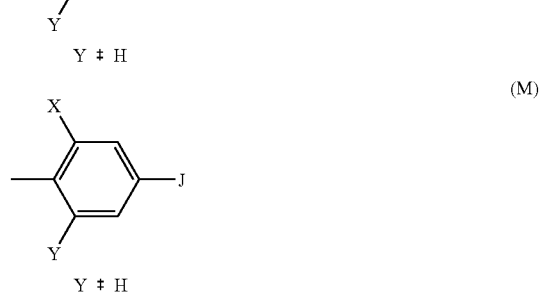

where only in the phenyl substitution pattern (G) X may also represent hydrogen, CKE especially preferably represents one of the groups

-continued (2)

[Structure with A, B, G, O forming a furanone ring]

or (8)

[Pyrazolidinedione structure with A, G, D, N, N]

A especially preferably represents $C_1$-$C_4$-alkyl or cyclopropyl,

B especially preferably represents hydrogen or methyl,

A, B and the carbon atom to which they are attached especially preferably represent saturated $C_5$-$C_6$-cycloalkyl in which optionally one ring member is replaced by oxygen and which is optionally monosubstituted by methyl, methoxy or propoxy, D especially preferably represents hydrogen, or A and D together especially preferably represent the group AD-1, in the case of CKE=group (8) A and D together especially preferably represent $C_3$-$C_5$-alkanediyl, G especially preferably represents hydrogen (a) or represents one of the groups (b)

[Acyl group with R¹]

(c)

[Carbonate group with OR²]

R¹ especially preferably represents $C_1$-$C_6$-alkyl, $C_1$-$C_2$-alkoxy-$C_1$-alkyl, cyclopropyl, each of which is optionally monosubstituted by chlorine, or represents phenyl which is optionally monosubstituted by chlorine, R² especially preferably represents $C_1$-$C_8$-alkyl, $C_2$-$C_6$-alkenyl or benzyl.

The general or preferred radical definitions or illustrations given above can be combined with one another as desired, i.e. including combinations between respective ranges and preferred ranges. They apply both to the end products and, correspondingly, to precursors and intermediates.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Special preference according to the invention is given to the compounds of the formula (I) which contain a combination of the meanings given above as being especially preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals can be mono- or polysubstituted, where in the case of polysubstitution the substituents can be identical or different.

In addition to the compounds mentioned in the preparation examples, particular mention may be made of the following compounds of the formula (I-1-a):

TABLE 1

[Structure showing pyrrolinone with OH, A, B, D, N, O, and phenyl ring with J, X, Y substituents]

2-I; X = H; Y = H.

| A | B | D |
|---|---|---|
| CH₃ | H | H |
| C₂H₅ | H | H |
| C₃H₇ | H | H |
| i-C₃H₇ | H | H |
| C₄H₉ | H | H |
| i-C₄H₉ | H | H |
| s-C₄H₉ | H | H |
| t-C₄H₉ | H | H |
| CH₃ | CH₃ | H |
| C₂H₅ | CH₃ | H |
| C₃H₇ | CH₃ | H |
| i-C₃H₇ | CH₃ | H |
| C₄H₉ | CH₃ | H |
| i-C₄H₉ | CH₃ | H |
| s-C₄H₉ | CH₃ | H |
| t-C₄H₉ | CH₃ | H |
| C₂H₅ | C₂H₅ | H |
| C₃H₇ | C₃H₇ | H |
| cyclopropyl- | CH₃ | H |
| cyclopentyl- | CH₃ | H |
| cyclohexyl- | CH₃ | H |
| —(CH₂)₂— | | H |
| —(CH₂)₄— | | H |
| —(CH₂)₅— | | H |
| —(CH₂)₆— | | H |
| —(CH₂)₇— | | H |
| —(CH₂)₂—O—(CH₂)₂— | | H |
| —CH₂—O—(CH₂)₃— | | H |
| —(CH₂)₂—S—(CH₂)₂— | | H |
| —CH₂—CHCH₃—(CH₂)₃— | | H |
| —CH₂—CHOCH₃—(CH₂)₃— | | H |
| —CH₂—CHOC₂H₅—(CH₂)₃— | | H |
| —CH₂—CHOC₃H₇—(CH₂)₃— | | H |
| —CH₂—CHOC₄H₉—(CH₂)₃— | | H |
| —CH₂—CHO—(CH₂)₂—OCH₃—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |
| —(CH₂)₂—CHi-C₃H₇—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—CHOC₃H₇—(CH₂)₂— | | H |
| —(CH₂)₂—CHO-i-C₃H₇—(CH₂)₂— | | H |
| —(CH₂)₂—C(CH₃)₂—(CH₂)₂— | | H |

TABLE 1-continued

| Structure | B |
|---|---|
| —CH$_2$—(CHCH$_3$)$_2$—(CH$_2$)$_2$— | H |
| CH$_2$—CH—(CH$_2$)$_2$—CH— with CH$_2$ bridge (cyclopentane) | H |
| —CH$_2$—CH—CH—CH$_2$— with (CH$_2$)$_4$ bridge (cyclohexane) | H |
| —CH$_2$—CH—CH—(CH$_2$)$_2$— with (CH$_2$)$_3$ bridge | H |
| indane ring | H |
| tetralin ring | H |

| A | D | B |
|---|---|---|
| —(CH$_2$)$_3$— | | H |
| —(CH$_2$)$_4$— | | H |
| —CH$_2$—CHCH$_3$—CH$_2$— | | H |
| —CH$_2$—CH$_2$—CHCH$_3$— | | H |
| —CH$_2$—CHCH$_3$—CHCH$_3$— | | H |
| —CH$_2$—CH(OCH$_3$)—CH$_2$— | | H |
| —CH$_2$—CH=CH—CH$_2$— | | H |
| —CH$_2$—CH—O—CH—CH$_2$— (epoxide) | | H |
| —CH$_2$—S—CH$_2$— | | H |
| —CH$_2$—S—(CH$_2$)$_2$— | | H |
| —(CH$_2$)$_2$—S—CH$_2$— | | H |
| —CH$_2$—CH—CH— with (CH$_2$)$_3$ bridge | | H |
| H | CH$_3$ | H |
| H | C$_2$H$_5$ | H |
| H | C$_3$H$_7$ | H |
| H | i-C$_3$H$_7$ | H |
| H | cyclopropyl | H |
| H | cyclopentyl | H |
| H | cyclohexyl | H |
| CH$_3$ | CH$_3$ | H |
| CH$_3$ | C$_2$H$_5$ | H |
| CH$_3$ | C$_3$H$_7$ | H |
| CH$_3$ | i-C$_3$H$_7$ | H |
| CH$_3$ | cyclopropyl | H |
| CH$_3$ | cyclopentyl | H |
| CH$_3$ | cyclohexyl | H |
| C$_2$H$_5$ | CH$_3$ | H |
| C$_2$H$_5$ | C$_2$H$_5$ | H |

Table 2: A, B and D as stated in table 1
2-I; X=4-CH$_3$; Y=H

Table 3: A, B and D as stated in table 1
2-I; X=6-CH$_3$; Y=H.

Table 4: A, B and D as stated in table 1
2-I; X=6-C$_2$H$_5$; Y=H.

Table 5: A, B and D as stated in table 1
X=2-CH$_3$; Y=H; 5-I.

Table 6: A, B and D as stated in table 1
X=2-CH$_3$; Y=4-CH$_3$; 5-I.

Table 7: A, B and D as stated in table 1
2-I; X=4-CH$_3$; Y=6-CH$_3$.

Table 8: A, B and D as stated in table 1
2-I; X=6-C$_2$H$_5$; Y=4-CH$_3$.

Table 9: A, B and D as stated in table 1
2-I; X=6-CH$_3$; Y=4-Cl.

Table 10: A, B and D as stated in table 1
2-I; X=6-C$_2$H$_5$; Y=4-Cl.

Table 11: A, B and D as stated in table 1
2-I; X=6-Cl; Y=4-CH$_3$.

Table 12: A, B and D as stated in table 1
2-I; X=5-CH$_3$; Y=4-CH$_3$.

Table 13: A, B and D as stated in table 1
X=2-CH$_3$; 4-I; Y=H.

Table 14: A, B and D as stated in table 1
X=2-C$_2$H$_5$; 4-I; Y=H.

Table 15: A, B and D as stated in table 1
X=2-CH$_3$; 4-I; Y=6-CH$_3$.

Table 16: A, B and D as stated in table 1
X=2-C$_2$H$_5$; 4-I; Y=6-CH$_3$.

Table 17: A, B and D as stated in table 1
X=2-C$_2$H$_5$; 4-I; Y=6-C$_2$H$_5$.

Table 18: A, B and D as stated in table 1
X=2-Cl; 4-I; Y=6-CH$_3$.

Table 19: A, B and D as stated in table 1
X=2-Cl; 4-I; Y=6-C$_2$H$_5$.

Table 20: A, B and D as stated in table 1
X=2-CH$_3$; 4-I; Y=5-CH$_3$.

Table 21: A, B and D as stated in table 1
X=2-CH$_3$; 3-I; Y=6-CH$_3$.

Table 22: A, B and D as stated in table 1
2-I; X=5-CH$_3$; Y=H.

TABLE 23

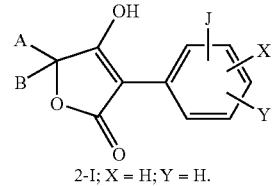

2-I; X = H; Y = H.

| A | B |
|---|---|
| CH$_3$ | H |
| C$_2$H$_5$ | H |
| C$_3$H$_7$ | H |

TABLE 23-continued

| | |
|---|---|
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |
| cyclopropyl | CH$_3$ |
| cyclopentyl | CH$_3$ |
| cyclohexyl | CH$_3$ |
| —(CH$_2$)$_2$— | |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —CH$_2$—O—(CH$_2$)$_3$— | |
| —(CH$_2$)$_2$—S—(CH$_2$)$_2$— | |
| —CH$_2$—CHCH$_3$—(CH$_2$)$_3$— | |
| —CH$_2$—CHOCH$_3$—(CH$_2$)$_3$— | |
| —CH$_2$—CHOC$_2$H$_5$—(CH$_2$)$_3$— | |
| —CH$_2$—CHOC$_3$H$_7$—(CH$_2$)$_3$— | |
| —CH$_2$—CHOC$_4$H$_9$—(CH$_2$)$_3$— | |
| —CH$_2$—CHO—(CH$_2$)$_2$—OCH$_3$—(CH$_2$)$_3$— | |
| —(CH$_2$)$_2$—CHCH$_3$—(CH$_2$)$_2$— | |
| —(CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi-C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHO-i-C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |

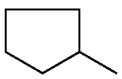

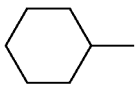

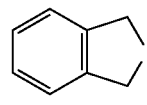

Table 24: A and B as stated in table 23
2-I; X=4-CH$_3$; Y=H

Table 25: A and B as stated in table 23
2-I; X=6-CH$_3$; Y=H.

Table 26: A and B as stated in table 23
2-I; X=6-C$_2$H$_5$; Y=H.

Table 27: A and B as stated in table 23
X=2-CH$_3$; Y=H; 5-I.

Table 28: A and B as stated in table 23
X=2-CH$_3$; Y=4-CH$_3$; 5-I.

Table 29: A and B as stated in table 23
2-I; X=4-CH$_3$; Y=6-CH$_3$.

Table 30: A and B as stated in table 23
2-I; X=6-C$_2$H$_5$; Y=4-CH$_3$.

Table 31: A and B as stated in table 23
2-I; X=6-CH$_3$; Y=4-Cl.

Table 32: A and B as stated in table 23
2-I; X=6-C$_2$H$_5$; Y=4-Cl.

Table 33: A and B as stated in table 23
2-I; X=6-Cl; Y=4-CH$_3$.

Table 34: A and B as stated in table 23
2-I; X=5-CH$_3$; Y=4-CH$_3$.

Table 35: A and B as stated in table 23
X=2-CH$_3$; 4-I; Y=H.

Table 36: A and B as stated in table 23
X=2-C$_2$H$_5$; 4-I; Y=H.

Table 37: A and B as stated in table 23
X=2-CH$_3$; 4-I; Y=6-CH$_3$.

Table 38: A and B as stated in table 23
X=2-C$_2$H$_5$; 4-I; Y=6-CH$_3$.

Table 39: A and B as stated in table 23
X=2-C$_2$H$_5$; 4-I; Y=6-C$_2$H$_5$.

Table 40: A and B as stated in table 23
X=2-Cl; 4-I; Y=6-CH$_3$.

Table 41: A and B as stated in table 23
X=2-Cl; 4-I; Y=6-C$_2$H$_5$.

Table 42: A and B as stated in table 23
X=2-CH$_3$; 4-I; Y=5-CH$_3$.

Table 43: A and B as stated in table 23
X=2-CH$_3$; 3-I; Y=6-CH$_3$.

Table 44: A and B as stated in table 23
2-I; X=5-CH$_3$; Y=H.

Preferred definitions of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

A$^1$ preferably represents one of the divalent heterocyclic groupings shown below

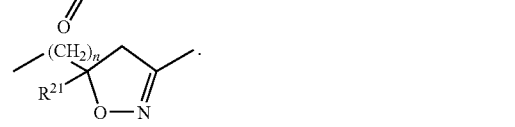

n preferably represents the numbers 0, 1, 2, 3 or 4.

A$^2$ preferably represents in each case optionally methyl-, ethyl-, methoxycarbonyl- or ethoxycarbonyl-substituted methylene or ethylene.

R$^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents in each case optionally fluorine-, chlorine- and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl.

$R^{18}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl, or together with $R^{17}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

$R^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2, or 3.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl(trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

Table Examples of the Compounds of the Formula (IIa)

| Example No. | (Positions) $(X^1)_m$ | $A^1$ | $R^{14}$ |
|---|---|---|---|
| IIa-1 | (2) Cl, (4) Cl | 1,3-dimethyl-5-methyl-4,5-dihydropyrazol-5-yl with CO-OCH$_3$ | OCH$_3$ |
| IIa-2 | (2) Cl, (4) Cl | 1,3-dimethyl-5-methyl-4,5-dihydropyrazol-5-yl with CO-OC$_2$H$_5$ | OCH$_3$ |
| IIa-3 | (2) Cl, (4) Cl | 1,3-dimethyl-5-methyl-4,5-dihydropyrazol-5-yl with CO-OCH$_3$ | OC$_2$H$_5$ |
| IIa-4 | (2) Cl, (4) Cl | 1,3-dimethyl-5-methyl-4,5-dihydropyrazol-5-yl with CO-OC$_2$H$_5$ | OC$_2$H$_5$ |
| IIa-5 | (2) Cl | 1,3-dimethyl-5-phenylpyrazol-4-yl | OCH$_3$ |
| IIa-6 | (2) Cl, (4) Cl | 1,3-dimethyl-5-phenylpyrazol-4-yl | OCH$_3$ |
| IIa-7 | (2) F | 1,3-dimethyl-5-phenylpyrazol-4-yl | OCH$_3$ |
| IIa-8 | (2) F | 1,3-dimethyl-5-(2-chlorophenyl)pyrazol-4-yl | OCH$_3$ |
| IIa-9 | (2) Cl, (4) Cl | 1,3-dimethyl-5-trichloromethyl-1,2,4-triazol-4-yl | OC$_2$H$_5$ |
| IIa-10 | (2) Cl, (4) CF$_3$ | 1-methyl-3-methyl-5-phenyl-1,2,4-triazol-4-yl | OCH$_3$ |
| IIa-11 | (2) Cl | 1,3-dimethyl-5-(2-fluorophenyl)pyrazol-4-yl | OCH$_3$ |
| IIa-12 | — | 3-methyl-5-phenyl-4,5-dihydroisoxazol-5-yl | OC$_2$H$_5$ |
| IIa-13 | (2) Cl, (4) Cl | 1,3-dimethyl-5-methylpyrazol-4-yl | OC$_2$H$_5$ |
| IIa-14 | (2) Cl, (4) Cl | 1,3-dimethyl-5-isopropylpyrazol-4-yl | OC$_2$H$_5$ |
| IIa-15 | (2) Cl, (4) Cl | 1,3-dimethyl-5-tert-butylpyrazol-4-yl | OC$_2$H$_5$ |
| IIa-16 | (2) Cl, (4) Cl | 5-ethyl-3-methyl-4,5-dihydroisoxazol-5-yl | OC$_2$H$_5$ |

(IIa)

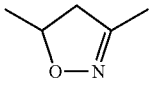

| Example No. | (Positions) $(X^1)_m$ | $A^1$ | $R^{14}$ |
|---|---|---|---|
| IIa-17 | (2) Cl, (4) Cl | 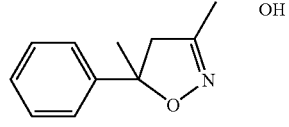 | $OC_2H_5$ |
| IIa-18 | — | 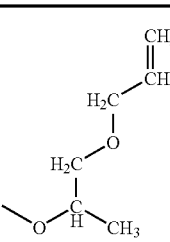 | OH |

Examples of the compounds of the formula (IIb) which are very particularly preferred as herbicide safeners according to the invention are listed in the table below.

(IIb)

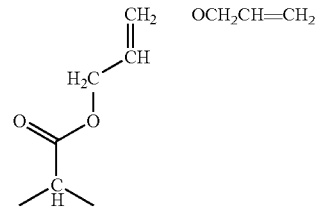

Table Examples of the Compounds of the Formula (IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | 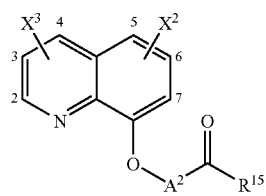 |
| IIb-13 | (5) Cl | — | 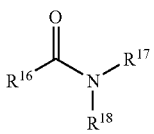 | $OCH_2CH=CH_2$ |
| IIb-14 | (5) Cl | — | 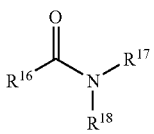 | $OC_2H_5$ |
| IIb-15 | (5) Cl | — | 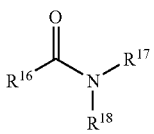 | $OCH_3$ |

(For IIb-13, IIb-14, IIb-15: $A^2$ values are shown with substitutions $C_2H_5$ and $CH_3$ on the $CH$ group respectively as indicated.)

Examples of the compounds of the formula (IIc) which are very particularly preferred as herbicide safeners according to the invention are listed in the table below.

(IIc)

$$R^{16}-\underset{\underset{R^{18}}{|}}{\overset{\overset{O}{\|}}{C}}-N{-}R^{17}$$

Table Examples of the Compounds of the Formula (IIc)

| Example No. | $R^{16}$ | $N(R^{17}, R^{18})$ |
|---|---|---|
| IIc-1 | $CHCl_2$ | $N(CH_2CH=CH_2)_2$ |
| IIc-2 | $CHCl_2$ | 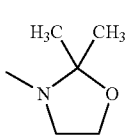 |

-continued

| Example No. | R¹⁶ | N(R¹⁷,R¹⁸) |
|---|---|---|
| IIc-3 | CHCl₂ | (2,2,3-trimethyl-5-methyl-oxazolidine structure) |
| IIc-4 | CHCl₂ | (methyl-spiro oxazolidine structure) |
| IIc-5 | CHCl₂ | (2,2,3-trimethyl-5-phenyl-oxazolidine structure) |
| IIc-6 | CHCl₂ | (3,4-dimethyl-benzoxazine structure) |
| IIc-7 | CHCl₂ | (2,2,3-trimethyl-5-furyl-oxazolidine structure) |

Examples of the compounds of the formula (IId) which are very particularly preferred as herbicide safeners according to the invention are listed in the table below.

(IId)

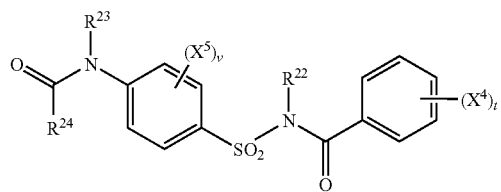

Table Examples of the Compounds of the Formula (IId)

| Example No. | R²² | R²³ | R²⁴ | (Positions) (X⁴)ₜ | (Positions) (X⁵)ᵥ |
|---|---|---|---|---|---|
| IId-1 | H | H | CH₃ | (2) OCH₃ | — |
| IId-2 | H | H | C₂H₅ | (2) OCH₃ | — |
| IId-3 | H | H | C₃H₇-n | (2) OCH₃ | — |
| IId-4 | H | H | C₃H₇-i | (2) OCH₃ | — |
| IId-5 | H | H | cyclopropyl | (2) OCH₃ | — |
| IId-6 | H | H | CH₃ | (2) OCH₃ (5) CH₃ | — |
| IId-7 | H | H | C₂H₅ | (2) OCH₃ (5) CH₃ | — |
| IId-8 | H | H | C₃H₇-n | (2) OCH₃ (5) CH₃ | — |
| IId-9 | H | H | C₃H₇-i | (2) OCH₃ (5) CH₃ | — |
| IId-10 | H | H | cyclopropyl | (2) OCH₃ (5) CH₃ | — |
| IId-11 | H | H | OCH₃ | (2) OCH₃ (5) CH₃ | — |
| IId-12 | H | H | OC₂H₅ | (2) OCH₃ (5) CH₃ | — |
| IId-13 | H | H | OC₃H₇-i | (2) OCH₃ (5) CH₃ | — |
| IId-14 | H | H | SCH₃ | (2) OCH₃ (5) CH₃ | — |
| IId-15 | H | H | SC₂H₅ | (2) OCH₃ (5) CH₃ | — |
| IId-16 | H | H | SC₃H₇-i | (2) OCH₃ (5) CH₃ | — |
| IId-17 | H | H | NHCH₃ | (2) OCH₃ (5) CH₃ | — |
| IId-18 | H | H | NHC₂H₅ | (2) OCH₃ (5) CH₃ | — |
| IId-19 | H | H | NHC₃H₇-i | (2) OCH₃ (5) CH₃ | — |
| IId-20 | H | H | NH-cyclopropyl (N-methyl) | (2) OCH₃ (5) CH₃ | — |
| IId-21 | H | H | NHCH₃ | (2) OCH₃ | — |
| IId-22 | H | H | NHC₃H₇-i | (2) OCH₃ | — |
| IId-23 | H | H | N(CH₃)₂ | (2) OCH₃ | — |
| IId-24 | H | H | N(CH₃)₂ | (3) CH₃ (4) CH₃ | — |
| IId-25 | H | H | CH₂—O—CH₃ | (2) OCH₃ | — |

Examples of the compounds of the formula (IIe) which are very particularly preferred as herbicide safeners according to the invention are listed in the table below.

(IIe)

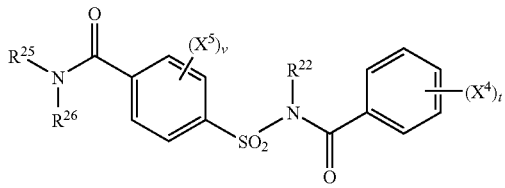

Table Examples of the Compounds of the Formula (IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H |  | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H |  | (2) $OCH_3$ (5) $CH_3$ | — |
| IIe-12 | H | $CH_3$ | $CH_3$ | (2) $OCH_3$ (5) $CH_3$ | — |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyrdiethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selective herbicidal combinations according to the invention comprising in each case one active compound of the formula (I) and one of the safeners defined above are listed in the table below.

TABLE

Examples of the combinations according to the invention

| Active compounds of the formula (I) | Safeners |
|---|---|
| I-1 | cloquintocet-mexyl |
| I-1 | fenchlorazole-ethyl |
| I-1 | isoxadifen-ethyl |
| I-1 | mefenpyr-diethyl |
| I-1 | furilazole |
| I-1 | fenclorim |
| I-1 | cumyluron |
| I-1 | daimuron/dymron |
| I-1 | dimepiperate |
| I-1 | IIe-11 |
| I-1 | IIe-5 |
| I-2 | cloquintocet-mexyl |
| I-2 | fenchlorazole-ethyl |
| I-2 | isoxadifen-ethyl |
| I-2 | mefenpyr-diethyl |
| I-2 | Furilazole |
| I-2 | Fenclorim |
| I-2 | Cumyluron |
| I-2 | daimuron/dymron |
| I-2 | dimepiperate |
| I-2 | IIe-11 |
| I-2 | IIe-5 |
| I-3 | cloquintocet-mexyl |
| I-3 | fenchlorazole-ethyl |
| I-3 | isoxadifen-ethyl |
| I-3 | mefenpyr-diethyl |
| I-3 | furilazole |
| I-3 | fenclorim |
| I-3 | cumyluron |
| I-3 | daimuron/dymron |
| I-3 | dimepiperate |
| I-3 | IIe-5 |
| I-3 | IIe-11 |
| I-4 | cloquintocet-mexyl |
| I-4 | fenchlorazole-ethyl |
| I-4 | isoxadifen-ethyl |
| I-4 | mefenpyr-diethyl |
| I-4 | furilazole |
| I-4 | fenclorim |
| I-4 | cumyluron |
| I-4 | daimuron/dymron |
| I-4 | dimepiperate |
| I-4 | IIe-11 |
| I-4 | IIe-5 |
| I-5 | cloquintocet-mexyl |
| I-5 | fenchlorazole-ethyl |
| I-5 | isoxadifen-ethyl |
| I-5 | mefenpyr-diethyl |
| I-5 | furilazole |
| I-5 | fenclorim |
| I-5 | cumyluron |
| I-5 | daimuron/dymron |
| I-5 | dimepiperate |
| I-5 | IIe-5 |
| I-5 | IIe-11 |
| I-6 | cloquintocet-mexyl |
| I-6 | fenchlorazole-ethyl |
| I-6 | isoxadifen-ethyl |
| I-6 | mefenpyr-diethyl |
| I-6 | furilazole |
| I-6 | fenclorim |
| I-6 | cumyluron |
| I-6 | daimuron/dymron |
| I-6 | dimepiperate |
| I-6 | IIe-5 |
| I-6 | IIe-11 |
| I-7 | cloquintocet-mexyl |
| I-7 | fenchlorazole-ethyl |
| I-7 | isoxadifen-ethyl |
| I-7 | mefenpyr-diethyl |
| I-7 | furilazole |
| I-7 | fenclorim |
| I-7 | cumyluron |
| I-7 | daimuron/dymron |
| I-7 | dimepiperate |
| I-7 | IIe-5 |
| I-7 | IIe-11 |

TABLE-continued

Examples of the combinations according to the invention

| Active compounds of the formula (I) | Safeners |
|---|---|
| I-8 | cloquintocet-mexyl |
| I-8 | fenchlorazole-ethyl |
| I-8 | isoxadifen-ethyl |
| I-8 | mefenpyr-diethyl |
| I-8 | furilazole |
| I-8 | fenclorim |
| I-8 | cumyluron |
| I-8 | daimuron/dymron |
| I-8 | dimepiperate |
| I-8 | IIe-5 |
| I-8 | IIe-11 |

It has now surprisingly been found that the above-defined active-compound combinations of iodophenyl-substituted cyclic ketoenols of the general formula (I) and safeners (antidotes) from the group (b') set out above combine very good useful plant tolerance with a high herbicidal activity and can be used in various crops, in particular in cereals (especially wheat), but also in soya beans, potatoes, corn and rice, for selective weed control.

In this context it is considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of substituted cyclic ketoenols on the crop plants, without at the same time having any critical adverse effect on the herbicidal activity against the weeds.

Emphasis may be given here to the particularly advantageous effect of the particularly preferred and most preferred combination partners from group (b'), particularly with regard to the gentle treatment of cereal plants, such as wheat, barley and rye, for example, but also corn and rice, as crop plants.

Using, for example, according to process (A) ethyl N-(2,6-dimethyl-4-iodophenylacetyl)-1-amino-cyclohexanecarboxylate as starting material, the course of the process according to the invention can be represented by the reaction scheme below:

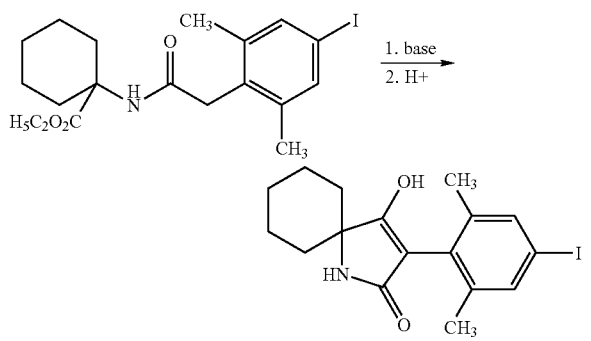

Using, for example, according to process. (B) ethyl O-(2,6-dimethyl-4-iodophenylacetyl)-2-hydroxyisobutyrate, the course of the process according to the invention can be represented by the reaction scheme below:

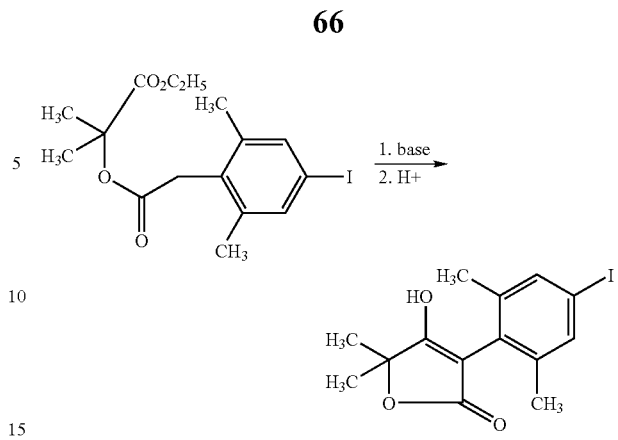

Using, for example, according to process (C) ethyl 2-(2,6-dimethyl-4-iodophenyl)-4-(4-methoxy)benzylmercapto-4-methyl-3-oxovalerate, the course of the process according to the invention can be represented by the reaction scheme below:

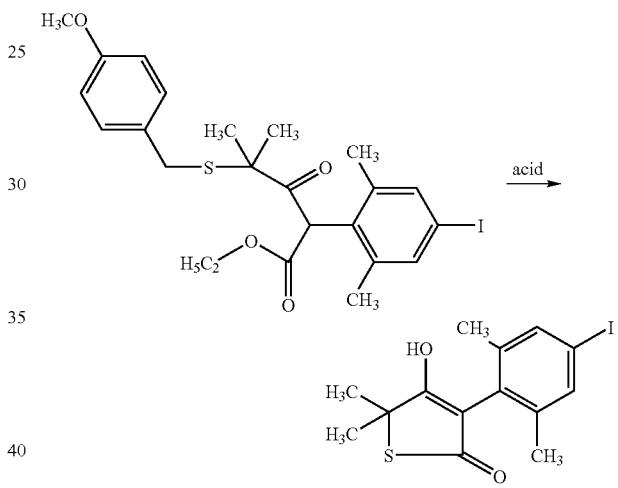

Using, for example, according to process (D) chlorocarbonyl 2-[(2,6-dimethyl-4-iodophenyl)]ketene and acetone as starting materials, the course of the process according to the invention can be represented by the reaction scheme below:

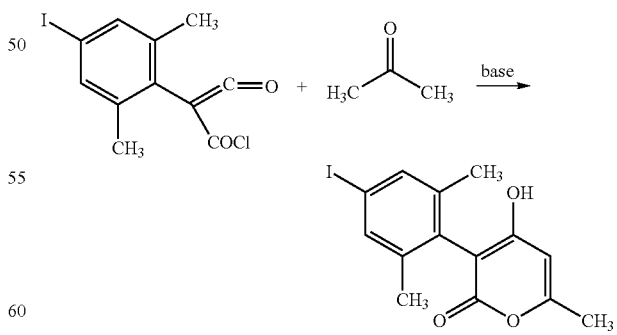

Using, for example, according to process (E) chlorocarbonyl 2-(2,6-dimethyl-4-iodophenyl)ketene and thiobenzamide as starting materials, the course of the process according to the invention can be represented by the reaction scheme below:

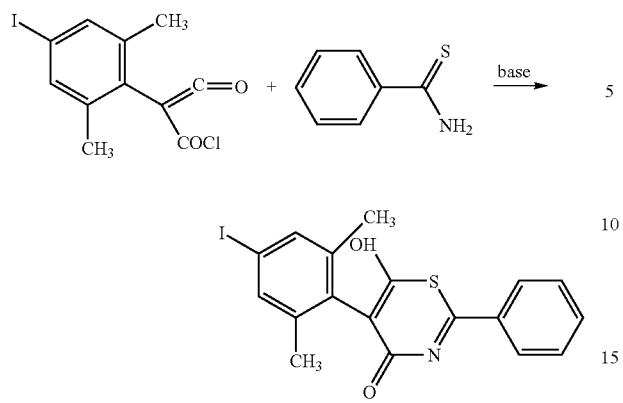

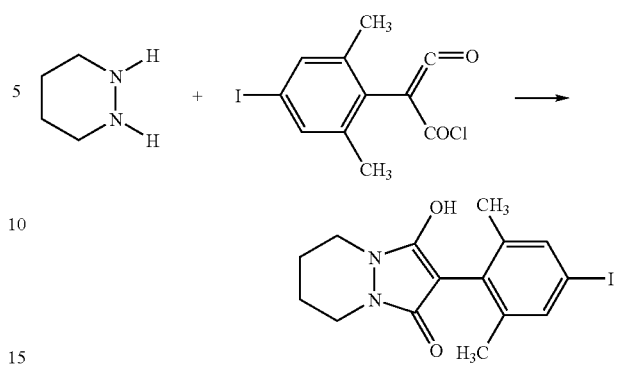

Using, for example, according to process (F) ethyl 5-(2,6-dimethyl-4-iodophenyl)-2,3-trimethylene-4-oxovalerate, the course of the process according to the invention can be represented by the reaction scheme below:

Using, for example, according to process (Hβ) hexahydropyridazine and dimethyl 2-(2,6-dimethyl-4-iodo)phenylmalonate as starting materials, the course of the process according to the invention can be represented by the reaction scheme below:

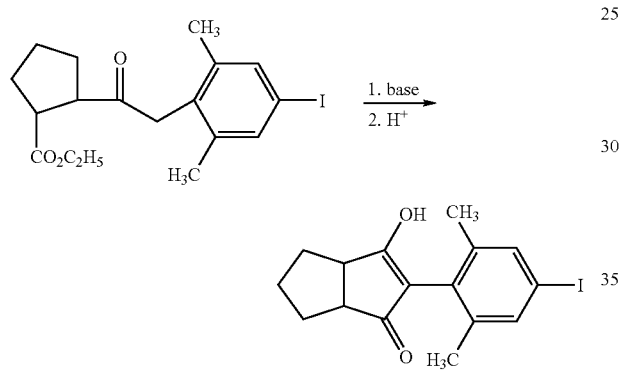

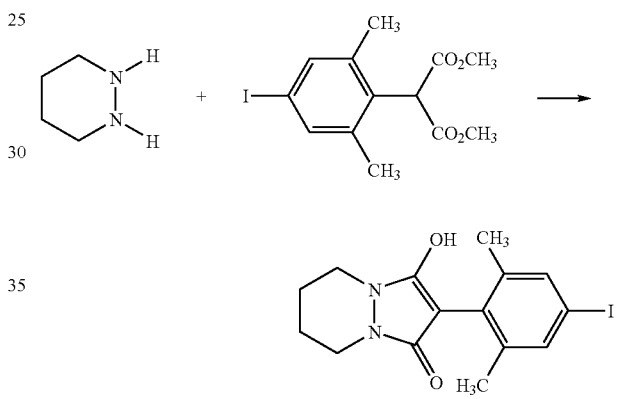

Using, for example, according to process (G) ethyl 5-[(2,6-dimethyl-4-iodo)phenyl]-2-methyl-5-oxohexanoate, the course of the process according to the invention can be represented by the reaction scheme below:

Using, for example, according to process (Hγ) 1-ethoxycarbonyl-2-[(2,6-dimethyl-4-iodo)phenyl-acetyl]hexahydropyridazine as starting material, the course of the reaction can be represented by the scheme below:

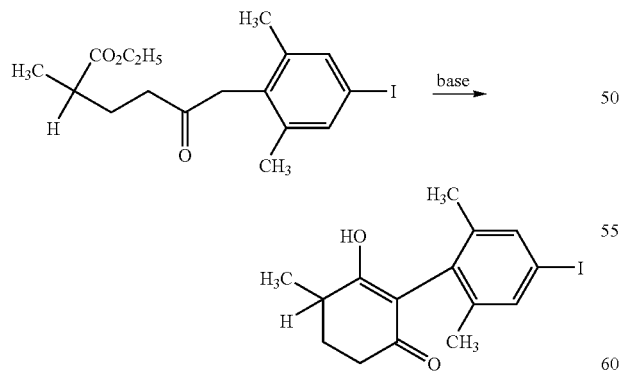

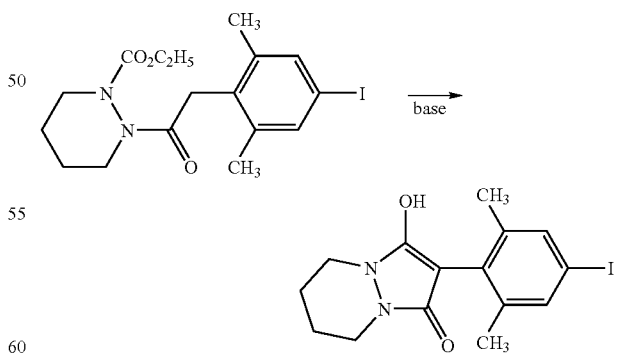

Using, for example, according to process (Hα) hexahydropyridazine and chlorocarbonyl 2-[(2,6-dimethyl-4-iodo)phenyl]ketene as starting materials, the course of the reaction of the process according to the invention can be represented by the reaction scheme below:

Using, for example, according to process (Iα) 3-(2-methyl-4-iodo-6-ethylphenyl)-5,5-dimethylpyrrolidine-2,4-dione and pivaloyl chloride as starting materials, the course of the process according to the invention can be represented by the reaction scheme below:

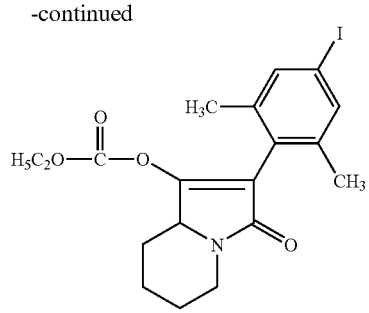

Using, for example, according to process (Iβ) 3-(2,6-dimethyl-4-iodophenyl)-5,5-dimethylpyrrolidine-2,4-dione and acetic anhydride as starting materials, the course of the process according to the invention can be represented by the reaction scheme below:

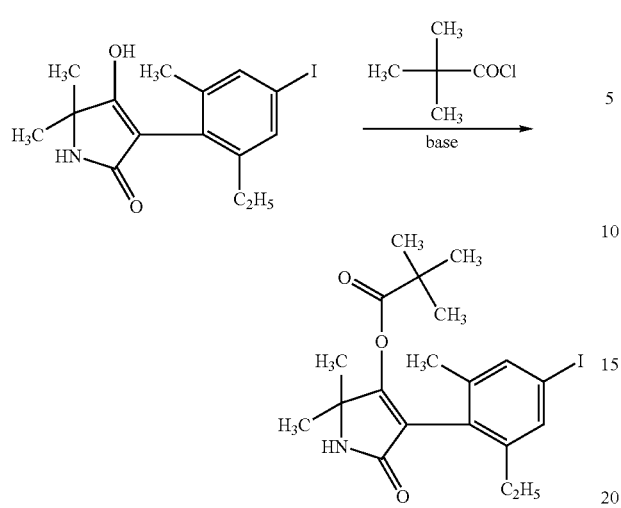

Using, for example, according to process (J) 8-[(2,6-dimethyl-4-iodo)phenyl]-1-azabicyclo-(4.3.0$^{1,6}$)-nonane-7,9-dione and ethyl chloroformate as starting materials, the course of the process according to the invention can be represented by the reaction scheme below:

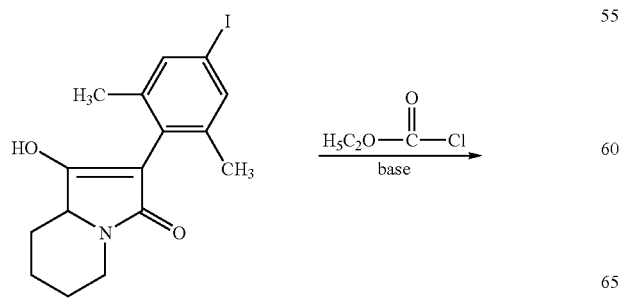

Using, for example, according to process (K) 3-(2,6-dimethyl-4-iodophenyl)-4-hydroxy-5-methyl-6-(3-pyridyl)pyrone and methyl chloromonothioformate as starting materials, the course of the reaction can be represented as follows:

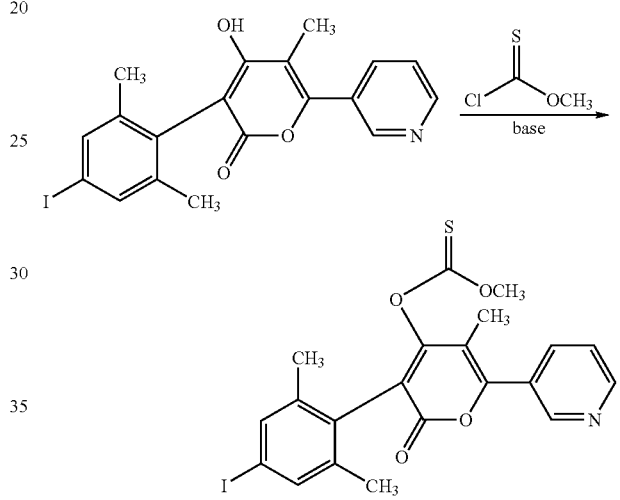

Using, for example, according to process (L) 3-(2,6-dimethyl-4-iodophenyl)-5,5-penta-methylenepyrrolidine-2,4-dione and methanesulfonyl chloride as starting material, the course of the reaction can be represented by the reaction scheme below:

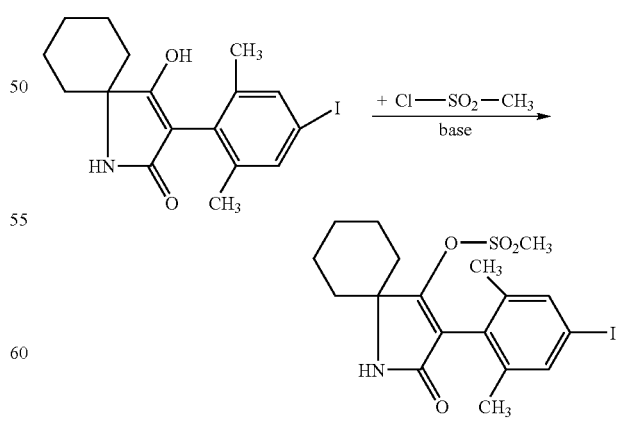

Using, for example, according to process (M) 3-(2,6-dimethyl-4-iodophenyl)-4-hydroxy-5,5-dimethylpyrrolidine-2,4-dione and 2,2,2-trifluoroethyl methanethiophosphonyl chloride as starting materials, the course of the reaction can be represented by the reaction scheme below:

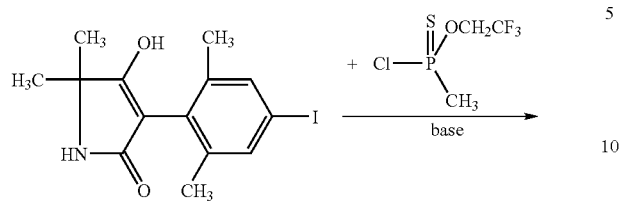

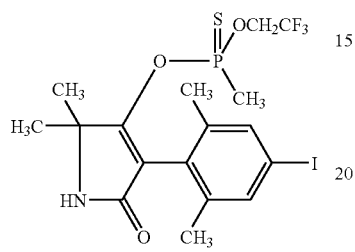

Using, for example, according to process (N) 3-(2-ethyl-4-iodo-6-methylphenyl]-5-cyclopropyl-5-methylpyrrolidine-2,4-dione and NaOH as components, the course of the process according to the invention can be represented by the reaction scheme below:

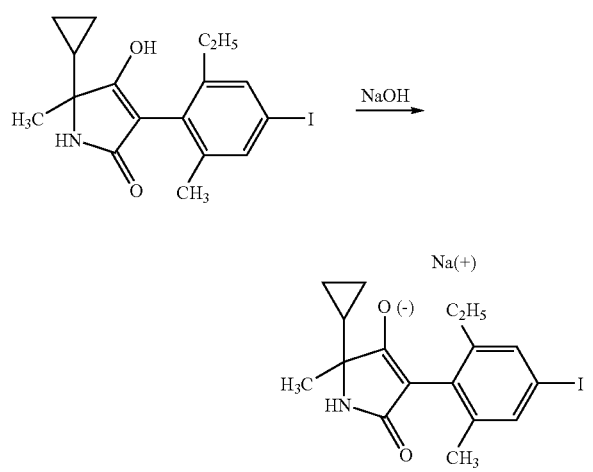

Using, for example, according to process (O) variant a 3-(2,6-dimethyl-4-iodophenyl)-4-hydroxy-5,5-tetramethylene-Δ³-dihydrofuran-2-one and ethyl isocyanate as starting materials, the course of the reaction can be represented by the reaction scheme below:

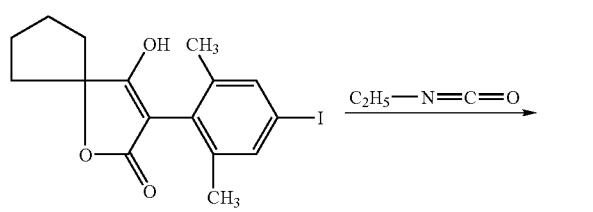

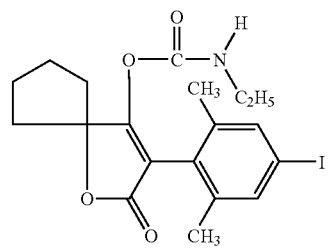

Using, for example, according to process (O) variant β 3-(2-methyl-4-iodo-6-ethylphenyl)-5-methylpyrrolidine-2,4-dione and dimethylcarbamoyl chloride as starting materials, the course of the reaction can be represented by the scheme below:

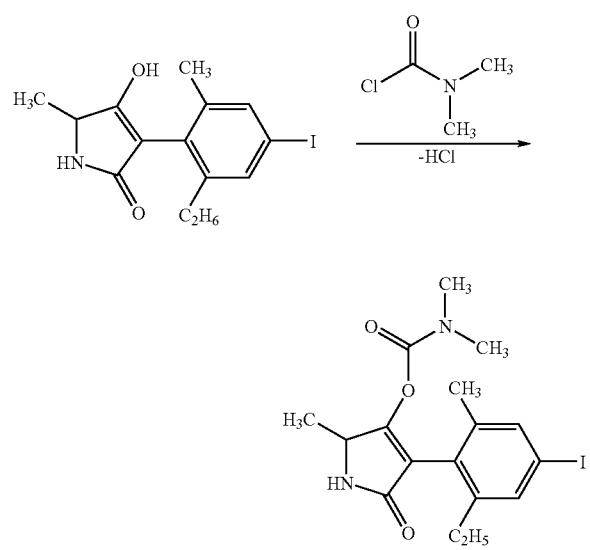

Using, for example, according to process (P) 3-(4-bromo-2,6-dimethylphenyl)-5,5-dimethylpyrrolidine-2,4-dione and sodium methoxide as starting materials, the course of the reaction can be represented by the scheme below:

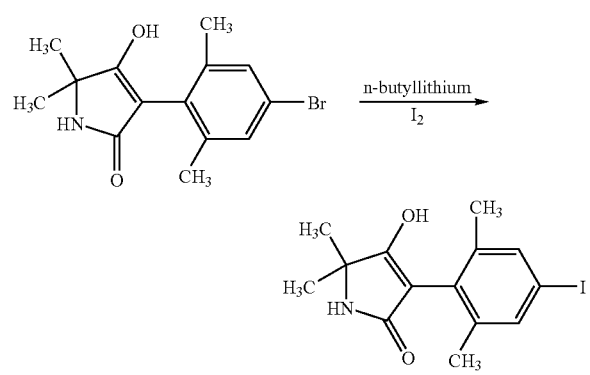 [SMILES: Cc1cc(Br)cc(C)c1C1=C(O)C(C)(C)NC1=O ; "I2" ; Cc1cc(I)cc(C)c1C1=C(O)C(C)(C)NC1=O]

The compounds, required as starting materials for the process (a) according to the invention, of the formula (II)

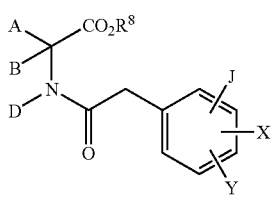
(II)

checker: Above, please change 'J' to 'I'#
in which
A, B, D, J, X, Y and $R^8$ are as defined above
are novel.

The acylamino acid esters of the formula (II) are obtained, for example, when amino acid derivatives of the formula (XXIII)

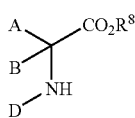
(XXIII)

in which
A, B, $R^8$ and D are as defined above
are acylated with substituted phenylacetic acid derivatives formula (XXIV)

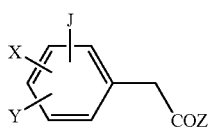
(XXIV)

in which
J, X and Y are as defined above and
Z represents a leaving group introduced by reagents, such as carbonyldiimidazole, carbonyldiimides (such as, for example, dicyclohexylcarbondiimide), phosphorylating agents (such as, for example, $POCl_3$, BOP-Cl), halogenating agents, for example thionyl chloride, oxalyl chloride, phosgene or chloroformic esters, for activating carboxylic acids
(Chem. Reviews 52, 237-416 (1953); Bhattacharya, Indian J. Chem. 6, 341-5, 1968)
or when acylamino acids of the formula (XXV)

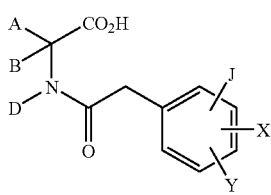
(XXV)

in which
A, B, D, J, X and Y are as defined above
are esterified (Chem. Ind. (London) 1568 (1968)).

The compounds of the formula (XXV)

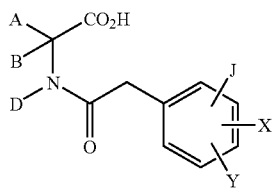
(XXV)

in which
A, B, D, J, X and Y are as defined above
are novel.

The compounds of the formula (XXV) are obtained when amino acids of the formula (XXVI)

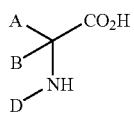
(XXVI)

in which
A, B and D are as defined above
are acylated with substituted phenylacetic acid derivatives of the formula (XXIV)

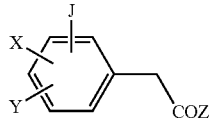
(XXIV)

in which
J, X and Y are as defined above and
Z is as defined above,
for example according to Schotten-Baumann (Organikum, VEB Deutscher Verlag der Wissenschaften, Berlin 1977, p. 505).

The compounds of the formula (XXIV) are novel. They can be prepared by processes known in principle and as illustrated in the examples (see, for example, H. Henecka, Houben-Weyl, Methoden der Organischen Chemie [Methods of Organic Chemistry], Vol. 8, pp. 467-469 (1952)).

The compounds of the formula (XXIV) are obtained, for example, by reacting substituted phenylacetic acids of the formula (XXVII)

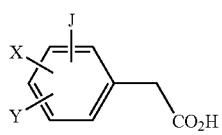
(XXVII)

in which
J, X and Y are as defined above
with halogenating agents (for example thionyl chloride, thionyl bromide, oxalyl chloride, phosgene, phosphorus trichloride, phosphorus tribromide or phosphorus pentachloride), phosphonylating agents, such as (for example $POCl_3$, BOP-Cl), carbonyidiimidazole, carbonyldiimides (for example dicyclohexylcarbonyldiimide), if appropriate in the presence of a diluent (for example optionally chlorinated aliphatic or aromatic hydrocarbons, such as toluene or methylene chloride, or ethers, for example tetrahydrofuran, dioxane, methyl tert-butyl ether) at temperatures of from −20° C. to 150° C., preferably from −10° C. to 100° C.

Some of the compounds of the formulae (XXIII) and (XXVI) are known, and/or they can be prepared by known processes (see, for example, Compagnon, Miocque Ann. Chim. (Paris) [14]5, pp. 11-22, 23-27 (1970)).

The substituted cyclic aminocarboxylic acids of the formula (XXVI) in which A and B form a ring are generally obtainable by the Bucherer-Bergs synthesis or by the Strecker synthesis, where they are obtained in different isomeric forms. Thus, the conditions of the Bucherer-Bergs synthesis afford predominantly the isomers (hereinbelow for the sake of simplicity referred to as β) in which the radicals R and the carboxyl group are in equatorial positions, whereas the conditions of the Strecker synthesis afford predominantly the isomers (hereinbelow for the sake of simpicity referred to as α) in which the amino group and the radicals R are in equatorial positions.

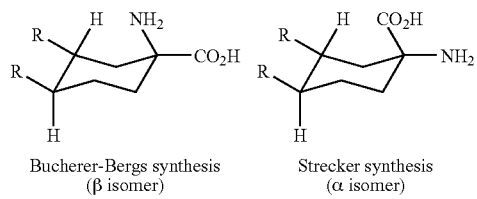

Bucherer-Bergs synthesis (β isomer)     Strecker synthesis (α isomer)

(L. Munday, J. Chem. Soc. 4372 (1961); J. T. Eward, C. Jitrangeri, Can. J. Chem. 53, 3339 (1975).

The starting materials, used in the above process (A), of the formula (II)

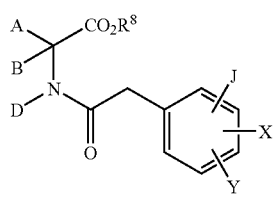
(II)

in which

A, B, D, J, X, Y and $R^8$ are as defined above can furthermore be prepared by reacting aminonitriles of the formula (XXVIII)

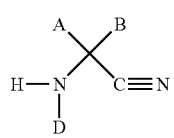
(XXVIII)

in which

A, B and D are as defined above with substituted phenylacetic acid derivatives of the formula (XXIV)

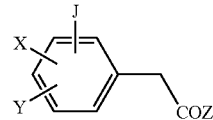
(XXIV)

in which

J, X, Y and Z are as defined above to give compounds of the formula (XXIX)

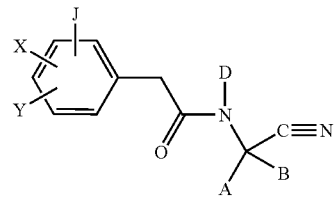
(XXIX)

in which

A, B, D, J, X and Y are as defined above and then subjecting these to an acidic alcoholysis.

The compounds of the formula (XXIX) are likewise novel.

The compounds, required as starting materials in the process (B) according to the invention, of the formula (III)

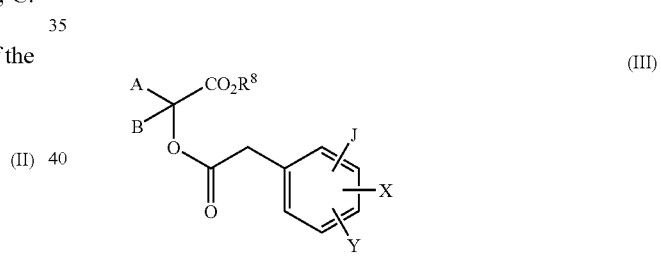
(III)

in which

A, B, J, X, Y and $R^8$ are as defined above, are novel.

They can be prepared by methods known in principle.

Thus, the compounds of the formula (III) are obtained, for example, when 2-hydroxycarboxylic esters of the formula (XXX-A)

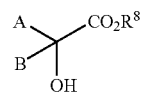
(XXX-A)

in which

A, B and $R^8$ are as defined above are acylated with substituted phenylacetic acid derivatives of the formula (XXIV)

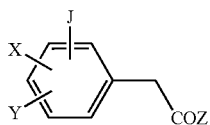
(XXIV)

in which
J, X, Y and Z are as defined above
(Chem. Reviews 52, 237-416 (1953)).

Furthermore, compounds of the formula (III) are obtained when
substituted phenylacetic acids of the formula (XXVII)

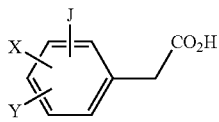
(XXVII)

in which
J, X and Y are as defined above
are alkylated with α-halocarboxylic esters of the formula (XXX-B)

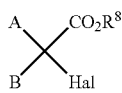
(XXX-B)

in which
A, B and $R^8$ are as defined above and
Hal represents chlorine or bromine.

Some of the compounds of the formula (XXVII) are commercially available, some are known; however, some are also novel.

The compounds of the formula (XXX-B) are commercially available.

The compounds of the formula (XXVII)

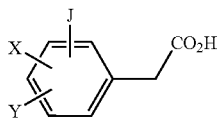
(XXVII)

in which
J, X and Y are as defined above
are obtained, for example, when phenylacetic esters of the formula (XXXI)

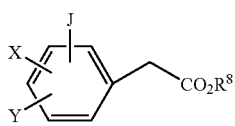
(XXXI)

in which
J, X, Y and $R^8$ are as defined above are hydrolyzed in the presence of acids or bases, in the presence of a solvent under generally known standard conditions.

Some of the compounds of the formula (XXXI) are commercially available, some are known, for example from WO 01/17973; however, some are also novel.

The compounds of the formula (XXXI)

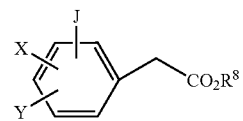
(XXXI)

in which
J, X, Y and $R^8$ are as defined above
are furthermore obtained by the process (Q) described in the examples
when phenylacetic esters of the formula (XXXI-a)

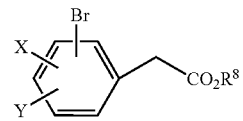
(XXXI-a)

in which
$R^8$, X and Y are as defined above
are reacted in the presence of iodides (preferably sodium iodide or potassium iodide) in the presence of a base and, if appropriate, in the presence of a catalyst (preferably copper salts, such as, for example, copper(I) iodide).

The phenylacetic esters of the formula (XXXI-a) are known in principle, for example from the applications WO 96/35 664, WO 97/02243, WO 97/01535, WO 98/05638 and DE-A-10 301 804, and they can be prepared by the processes described in these publications.

The compounds, required as starting materials for the process (C) above, of the formula (IV)

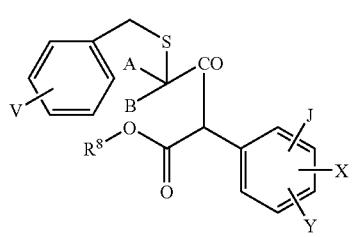
(IV)

in which
A, B, J, V, X, Y and $R^8$ are as defined above
are novel.

They can be prepared by methods known in principle.

The compounds of the formula (IV) are obtained, for example, when substituted phenylacetic esters of the formula (XXXI)

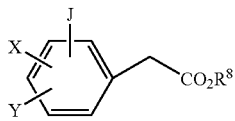
(XXXI)

in which
J, X, Y and $R^8$ are as defined above
are acylated with 2-benzylthiocarbonyl halides of the formula (XXXII)

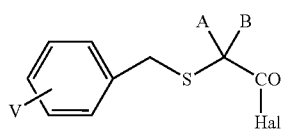
(XXXII)

in which
A, B and V are as defined above and
Hal represents halogen (in particular chlorine or bromine)
in the presence of strong bases (see, for example, M. S. Chambers, E. J. Thomas, D. J. Williams, J. Chem. Soc. Chem. Commun., (1987), 1228).

Some of the benzylthiocarbonyl halides of the formula (XXXII) are known, and/or they can be prepared by known processes (J. Antibiotics (1983), 26, 1589).

The halocarbonyl ketenes of the formula (VI) required as starting materials for the above processes (D), (E) and (H-α) are novel. They can be prepared by methods known in principle (cf., for example, Org. Prep. Proced. Int., 7, (4), 155-158, 1975 and DE 1 945 703). Thus, for example, the compounds of the formula (VI)

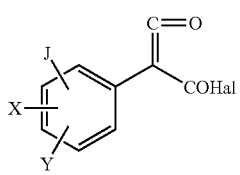
(VI)

in which
J, X and Y are as defined above and
Hal represents chlorine or bromine
are obtained when
substituted phenylmalonic acids of the formula (XXXIII)

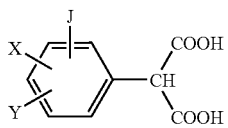
(XXXIII)

in which
J, X and Y are as defined above
are reacted with acid halides, such as, for example, thionyl chloride, phosphorus(V) chloride, phosphorus(III) chloride, oxalyl chloride, phosgene or thionyl bromide, if appropriate in the presence of catalysts, such as, for example, dimethylformamide, methylsterylformamide or triphenylphosphine, and, if appropriate, in the presence of bases, such as, for example, pyridine or triethylamine.

Some of the substituted phenylmalonic acids of the formula (XXXIII) are known or commercially available; however, some are also novel. They can be prepared in a simple manner by known processes (cf., for example, Organikum, VEB Deutscher Verlag der Wissenschaften, Berlin 1977, p. 517 ff, EP-A-528 156, WO 96/35 664, WO 97/02 243, WO 97/01535, WO 97/36868 and WO 98/05638).

Thus, phenylmalonic acids of the formula (XXXIII)

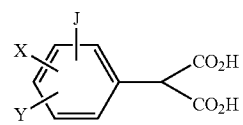
(XXXIII)

in which
J, X and Y are as defined above
are obtained when phenylmalonic esters of the formula (XI)

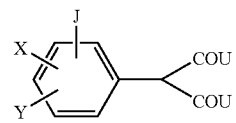
(XI)

in which
J, X and Y are as defined above
and U represents $OR^8$ or $NH_2$,
where $R^8$ is as defined above,
are initially hydrolyzed in the presence of a base and of a solvent and then carefully acidified (see, for example, EP-A-528 156, WO 96/35 664, WO 97/02 243).

The malonic esters of the formula (XI)

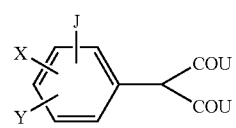
(XI)

in which
J, X and Y are as defined above
and U represents $OR^8$ or $NH_2$,
where $R^8$ is as defined above,
are known (for example WO 01/017973, Larock et al., Tetrahedron 52 2743 ff. (1996); however, some are also novel.

They can be prepared by generally known methods of organic chemistry (cf., for example, Tetrahedron Lett. 27, 2763 (1986), Organikum VEB Deutscher Verlag der Wissenschaften, Berlin 1977, p. 587 ff., WO 96/35664, WO 97/02243, WO 97/01535, WO 97/36868, WO 98/05638 and WO 99/47525).

The carbonyl compounds, required as starting materials for the process (D) according to the invention, of the formula (V)

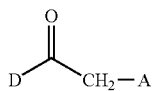

in which

A and D are as defined above or silylenol ethers thereof of the formula (Va)

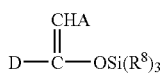

in which

A, D and $R^8$ are as defined above are commercially available compounds, generally known compounds or compounds which can be obtained by known processes.

The preparation of the ketene acid chlorides of the formula (VI) required as starting materials for carrying out the process (E) according to the invention have already been described above. The thioamides, required for carrying out the process (E) according to the invention, of the formula (VII)

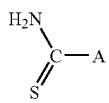

in which

A is as defined above are compounds which are generally known in organic chemistry.

The compounds, required as starting materials in the above process (F), of the formula (VIII)

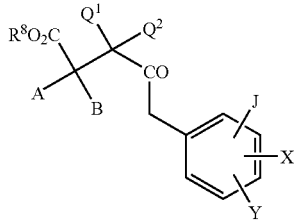

in which

A, B, J, $Q^1$, $Q^2$, X, Y and $R^8$ are as defined above are novel.

They can be prepared by methods known in principle.

The 5-aryl-4-ketocarboxylic esters of the formula (VIII) are obtained, for example, when 5-aryl-4-ketocarboxylic acids of the formula (XXXIV)

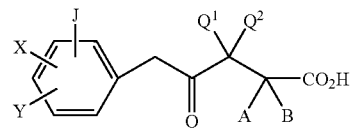

in which

J, X, Y, A, B, $Q^1$ and $Q^2$ are as defined above are esterified (cf., for example, Organikum, 15th edition, Berlin, 1977, page 499) or alkylated (see Preparation Example).

The 5-aryl-4-ketocarboxylic acids of the formula (XXXIV)

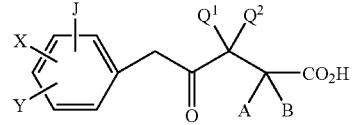

in which

A, B, J, $Q^1$, $Q^2$, X and Y are as defined above are novel; however, they can be prepared by methods known in principle (WO 96/01 798, WO 97/14667, WO 98/39281).

The 5-aryl-4-ketocarboxylic acids of the formula (XXXIV) are obtained, for example, when 2-phenyl-3-oxoadipic esters of the formula (XXXV)

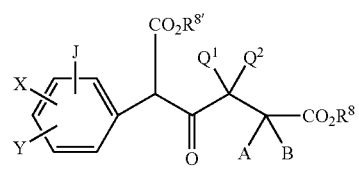

in which

A, B, J, $Q^1$, $Q^2$, X and Y are as defined above and $R^8$ and $R^{8'}$ represent alkyl (in particular $C_1$-$C_8$-alkyl) and, when the compound of the formula (XXXVII-a) is used, $R^8$ represents hydrogen, are decarboxylated, if appropriate in the presence of a diluent and if appropriate in the presence of a base or acid (cf., for example, Organikum, 15th edition, Berlin, 1977, page 519 to 521, WO 96/01798, WO 97/14667, WO 98/39281).

The compounds of the formula (XXXV)

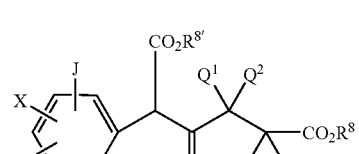

in which

A, B, J, $Q^1$, $Q^2$, X, Y, $R^8$, $R^{8'}$ are as defined above and, when the compound of the formula (XXXVII-a) is used, $R^8$ represents hydrogen are novel.

The compounds of the formula (XXXV) are obtained, for example, when dicarboxylic monoester chlorides of the formula (XXXVI),

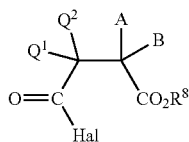
(XXXVI)

in which
A, B, $Q^1$, $Q^2$ and $R^8$ are as defined above and
Hal represents chlorine or bromine
or carboxylic anhydrides of the formula (XXXVII-a)

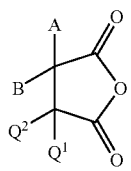
(XXXVII-a)

in which
A, B, $Q^1$ and $Q^2$ are as defined above
are acylated with a phenylacetic ester of the formula (XXXI)

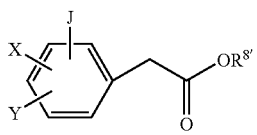
(XXXI)

in which
J, X, Y and $R^{8'}$ are as defined above
in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XXXVI) and (XXXVII-a) are known compounds of organic chemistry, and/or they can be prepared in a simple manner by methods known in principle.

The compounds, required as starting materials in the above process (G), of the formula (IX)

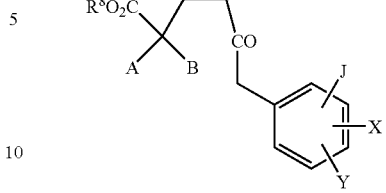
(IX)

in which
A, B, J, $Q^3$, $Q^4$, $Q^5$, $Q^6$, X, Y and $R^8$ are as defined above are novel.
They can be prepared by methods known in principle.
The 6-aryl-5-ketocarboxylic esters of the formula (IX) are obtained, for example, when 6-aryl-5-ketocarboxylic acids of the formula (XXXVIII)

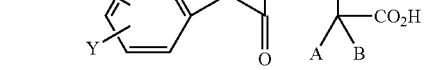
(XXXVIII)

in which
A, B, J, $Q^3$, $Q^4$, $Q^5$, $Q^6$, X and Y are as defined above
are esterified (cf., for example, Organikum, 15th edition, Berlin, 1977, page 499, WO 99/43649, WO 99/48869).
The 6-aryl-5-ketocarboxylic acids of the formula (XXXVIII)

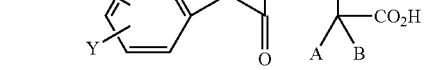
(XXXVIII)

in which
A, B, J, $Q^3$, $Q^4$, $Q^5$, $Q^6$, X and Y are as defined above
are novel. They can be prepared by methods known in principle (WO 99/43649, WO 99/48869), for example when substituted 2-phenyl-3-oxoheptanedioic esters of the formula (XXXIX)

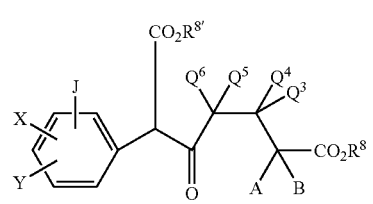
(XXXIX)

in which
A, B, J, $Q^3$, $Q^4$, $Q^5$, $Q^6$, X and Y are as defined above and
$R^8$ and $R^{8'}$ represent alkyl (preferably $C_1$-$C_6$-alkyl) and, when the compound of the formula (XXXVII-b) is used, $R^8$ represents hydrogen, are hydrolyzed and decarboxylated, if appropriate in the presence of a diluent and if appropriate in the presence of a base or acid (cf., for example, Organikum, 15th edition, Berlin, 1977, pages 519 to 521, WO 99/43649, WO 99/48869).

The compounds of the formula (XXXIX)

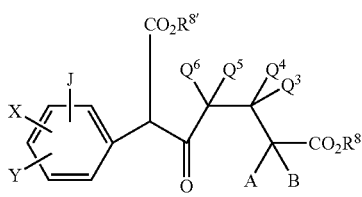

(XXXIX)

in which
A, B, J, $Q^3$, $Q^4$, $Q^5$, $Q^6$, X, Y, $R^8$ and $R^{8'}$ are as defined above
are novel and can be obtained
when dicarboxylic esters of the formula (XL)

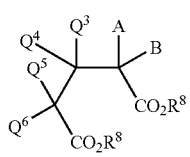

(XL)

in which
A, B, $Q^3$, $Q^4$, $Q^5$, $Q^6$ and $R^8$ are as defined above
or carboxylic anhydrides of the formula (XXXVII-b)

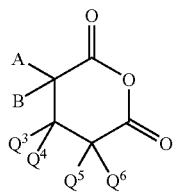

(XXXVII-b)

in which A, B, $Q^3$, $Q^4$, $Q^5$, $Q^6$ are as defined above
are condensed with a substituted phenylacetic ester of the formula (XXXI)

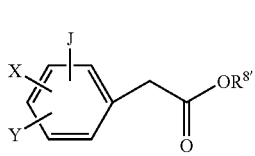

(XXXI)

in which
J, X, Y and $R^{8'}$ are as defined above
in the presence of a diluent and in the presence of a base.

Some of the compounds of the formula (XL) are known, and/or they can be prepared by known processes.

Some of the hydrazines, required as starting materials for the process (H-α) and (H-β) according to the invention, of the formula (X)

A-NH—NH-D (X)

in which
A and D are as defined above are known, and/or they can be prepared by methods known from the literature (cf., for example, Liebigs Ann. Chem. 585, 6 (1954); Reaktionen der organischen Synthese [Reactions of Organic Synthesis], C. Ferri, pages 212, 513; Georg Thieme Verlag Stuttgart, 1978; Liebigs Ann. Chem. 443, 242 (1925); Chem. Ber. 98, 2551 (1965), EP-A-508 126, WO 92/16510, WO 99/47 525, WO 01/17 972).

The compounds, required for the process (H-γ) according to the invention, of the formula (XII)

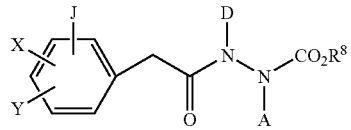

(XII)

in which
A, D, J, X, Y and $R^8$ are as defined above
are novel.

The acylcarbazates of the formula (XII) are obtained, for example, when carbazates of the formula (XLI)

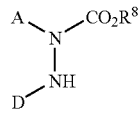

(XLI)

in which
A, $R^8$ and D are as defined above
are acylated with substituted phenylacetic acid derivatives of the formula (XXIV)

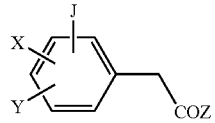

(XXIV)

in which
J, X, Y and Z are as defined above
(Chem. Reviews 52, 237-416 (1953); Bhattacharya, Indian J. Chem. 6, 341-5, 1968).

Some of the carbazates of the formula (XLI) are commercially available compounds and some are known compounds, or they can be prepared by processes of organic chemistry known in principle.

The compounds of the formula (XXIV) have already been described in connection with the intermediates for the process (A) and (B).

The acid halides of the formula (XIII), carboxylic anhydrides of the formula (XIV), chloroformic esters or chloroformic thioesters of the formula (XV), chloromonothioformic esters or chlorodithioformic esters of the formula (XVI), sulfonyl chlorides of the formula (XVII), phosphorus compounds of the formula (XVIII) and metal hydroxides, metal alkoxides or amines of the formulae (XIX) and (XX) and isocyanates of the formula (XXI) and carbamoyl chlorides of the formula (XXII) furthermore required as starting materials for carrying out the processes (I), (J), (K), (L), (M), (N) and (O) according to the invention are generally known compounds of organic or inorganic chemistry.

In addition, the compounds of the formulae (V), (VII), (XIII) to (XXII), (XXIII), (XXVI), (XXVIII), (XXX-A), (XXX-B), (XXXII), (XXXVI), (XXXVII-a), (XXXVII-b), (XL) and (XLI) are furthermore known from the patent applications cited at the outset, and/or they can be prepared by the methods stated in these publications.

The process (A) is characterized in that compounds of the formula (II) in which A, B, D, J, X, Y and $R^8$ are as defined above are subjected to an intramolecular condensation in the presence of a base.

Suitable for use as diluents in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures can be varied within a relatively wide range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in approximately doubly equimolar amounts. However, it is also possible to use a relatively large excess (up to 3 mol) of one or the other component.

The process (B) is characterized in that compounds of the formula (III) in which A, B, J, X, Y and $R^8$ are as defined above are subjected to an intramolecular condensation in the presence of a diluent and in the presence of a base.

Suitable for use as diluents in the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperatures can be varied within a relatively wide range. In general, the process is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (II) and the deprotonating bases are generally employed in approximately equimolar amounts. However, it is also possible to use a relatively large excess (up to 3 mol) of one or the other component.

The process (C) is characterized in that compounds of the formula (IV) in which A, B, V, J, X, Y and $R^8$ are as defined above are cyclized intramolecularly in the presence of an acid and, if appropriate, in the presence of a diluent.

Suitable diluents for the process (C) according to the invention are all inert organic solvents. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulfoxide, sulfolane, dimethylformamide and N-methylpyrrolidone. It is furthermore possible to use alcohols, such as methanol, ethanol, propanol, isopropanol, butanol, isobutanol, tert-butanol.

If appropriate, the acid used may also serve as diluent.

Suitable for use as acid in the process (C) according to the invention are all customary inorganic and organic acids, such as, for example, hydrohalic acids, sulfuric acid, alkyl-, aryl- and haloalkylsulfonic acids, in particular halogenated alkylcarboxylic acids, such as, for example, trifluoroacetic acid.

When carrying out the process (C) according to the invention, the reaction temperatures can be varied within a relatively wide range. In general, the process is carried out at temperatures between 0° C. and 250° C., preferably between 50° C. and 150° C.

The process (C) according to the invention is generally carried out under atmospheric pressure.

When carrying out the process (C) according to the invention, the reaction components of the formula (IV) and the acid are, for example, employed in equimolar amounts. However, it is also possible, if appropriate, to use the acid as solvent or as catalyst.

The process (D) according to the invention is characterized in that carbonyl compounds of the formula (V) or their enole ethers of the formula (V-a) are reacted with ketene acid halides of the formula (VI) in the presence of a diluent and, if appropriate, in the presence of an acid acceptor.

Suitable diluents for use in the process (D) according to the invention are all inert organic solvents. Preference is given to using optionally halogenated hydrocarbons, such as toluene, xylene, mesitylene, chlorobenzene and dichlorobenzene, furthermore ethers, such as dibutyl ether, glycol dimethyl ether diglycol dimethyl ether and diphenyl ether, moreover polar solvents, such as dimethyl sulfoxide, sulfolane, dimethylformamide or N-methylpyrrolidone.

Suitable acid acceptors for carrying out the process variant (D) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (D) according to the invention, the reaction temperatures can be varied within a relatively wide range. Expediently, the process is carried out at temperatures between 0° C. and 250° C., preferably between 50° C. and 220° C.

The process (D) according to the invention is expediently carried out under atmospheric pressure.

When carrying out the process (D) according to the invention, the reaction components of the formulae (V) and (VI), in which A, D, J, X and Y are as defined above and Hal represents halogen, and, if appropriate, the acid acceptors are generally employed in approximately equimolar amounts. However, it is also possible to use a relatively large excess (up to 5 mol) of one component or the other.

The process (E) according to the invention is characterized in that thioamides of the formula (VII) are reacted with ketene acid halides of the formula (VI) in the presence of a diluent and, if appropriate, in the presence of an acid acceptor.

Suitable for use as diluents for the process variant (E) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulfoxide, sulfolane, dimethylformamide and N-methylpyrrolidone.

Suitable for use as acid acceptors for carrying out the process (E) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process (E) according to the invention, the reaction temperatures can be varied within a relatively wide range. Expediently, the process is carried out at temperatures between 0° C. and 250° C., preferably between 20° C. and 220° C.

The process (E) according to the invention is expediently carried out under atmospheric pressure.

When carrying out the process (E) according to the invention, the reaction components of the formulae (VII) and (VI), in which A, J, X and Y are as defined above and Hal represents halogen, and, if appropriate, the acid acceptors are generally employed in approximately equimolar amounts. However, it is also possible to use a relatively large excess (up to 5 mol) of one component or the other.

The process (F) is characterized in that compounds of the formula (VIII) in which A, B, J, $Q^1$, $Q^2$, X, Y and $R^8$ are as defined above are subjected to an intramolecular condensation in the presence of a base.

Suitable diluents for use in the process (F) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (F) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (F) according to the invention, the reaction temperatures can be varied within a relatively wide range. In general, the process is carried out at temperatures between −75° C. and 250° C., preferably between −50° C. and 150° C.

The process (F) according to the invention is generally carried out under atmospheric pressure.

When carrying out the process (F) according to the invention, the reaction components of the formula (VIII) and the deprotonating bases are generally employed in approximately equimolar amounts. However, it is also possible to use a relatively large excess (up to 3 mol) of one or the other component.

The process (G) is characterized in that compounds of the formula (IX) in which A, B, $Q^3$, $Q^4$, $Q^5$, $Q^6$, J, X, Y and $R^8$ are as defined above are subjected to an intramolecular condensation in the presence of bases.

Suitable diluents for use in the process (G) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (G) according to the invention are all customary proton acceptors.

Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide. When carrying out the process (G) according to the invention, the reaction temperatures can be varied within a relatively wide range. In general, the process is carried out at temperatures between 0° C. and 250° C., preferably between 50° C. and 150° C.

The process (G) according to the invention is generally carried out under atmospheric pressure.

When carrying out the process (G) according to the invention, the reaction components of the formula (IX) and the deprotonating bases are generally employed in approximately equimolar amounts. However, it is also possible to use a relatively large excess (up to 3 mol) of one or the other component.

The process (H-α) according to the invention is characterized in that hydrazines of the formula (X) or salts of these compounds are reacted with ketene acid halides of the formula (VI) in the presence of a diluent and, if appropriate, in the presence of an acid acceptor.

Suitable diluents for use in the process (H-α) according to the invention are all inert organic solvents. Preference is given to using optionally chlorinated hydrocarbons, such as, for example, mesitylene, chlorobenzene and dichlorobenzene, toluene, xylene, furthermore ethers, such as dibutyl ether, glycol dimethyl ether, diglycol dimethyl ether and diphenylethane, moreover polar solvents, such as dimethyl sulfoxide, sulfolane, dimethylformamide or N-methylpyrrolidone.

Suitable acid acceptors for carrying out the process variant (H-α) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (H-α) according to the invention, the reaction temperatures can be varied within a relatively wide range. Expediently, the process is carried out at temperatures between 0° C. and 250° C., preferably between 50° C. and 220° C.

The process (H-α) according to the invention is expediently carried out under atmospheric pressure.

When carrying out the process (H-α) according to the invention, the reaction components of the formulae (VI) and (X), in which A, D, J, X and Y are as defined above and Hal represents halogen, and, if appropriate, the acid acceptors are generally employed in approximately equimolar amounts. However, it is also possible to use a relatively large excess (up to 5 mol) of one component or the other.

The process (H-β) is characterized in that hydrazines of the formula (X) or salts of this compound, in which A and D are as defined above, are subjected to a condensation with malonic esters or malonamides of the formula (XI) in which U, J, X, Y and $R^8$ are as defined above, in the presence of a base.

Suitable diluents for use in the process (H-β) according to the invention are all inert organic solvents. Preference is given to using optionally halogenated hydrocarbons, such as toluene, xylene, mesitylene, chlorobenzene and dichlorobenzene, furthermore ethers, such as dibutyl ether, tetrahydrofuran, dioxane, diphenyl ether, glycol dimethyl ether and diglycol dimethyl ether, moreover polar solvents, such as dimethyl sulfoxide, sulfolane, dimethylformamide, dimethylacetamide and N-methylpyrrolidone, and also alcohols, such as methanol, ethanol, propanol, isopropanol, butanol, isobutanol and tert-butanol.

Suitable bases (deprotonating agents) for carrying out the process (H-β) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

It is also possible to use tertiary amines, such as triethylamine, pyridine, diazabicyclooctane (DABCO), diazabicycloundecane (DBU), diazabicyclononene (DBN), Hünig base and N,N-dimethylaniline.

When carrying out the process (H-β) according to the invention, the reaction temperatures can be varied within a relatively wide range. In general, the process is carried out at temperatures between 0° C. and 280° C., preferably between 50° C. and 180° C.

The process (H-β) according to the invention is generally carried out under atmospheric pressure.

When carrying out the process (H-β) according to the invention, the reaction components of the formulae (XI) and (X) are generally employed in approximately equimolar amounts. However, it is also possible to use a relatively large excess (up to 3 mol) of one component or the other.

The process (H-γ) is characterized in that compounds of the formula (XII) in which A, D, J, X, Y and $R^8$ are as defined above are subjected to an intramolecular condensation in the presence of a base.

Suitable for use as diluents in the process (H-γ) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (H-γ) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. It is also possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (H-γ) according to the invention, the reaction temperatures can be varied within a relatively wide range. In general, the process is carried out at temperatures between 0° C. and 250° C., preferably between 50° C. and 150° C.

The process (H-γ) according to the invention is generally carried out under atmospheric pressure.

When carrying out the process (H-γ) according to the invention, the reaction components of the formula (XII) and the deprotonating bases are generally employed in approximately doubly equimolar amounts. However, it is also possible to use a relatively large excess (up to 3 mol) of one or the other component.

The process (I-α) is characterized in that compounds of the formulae (I-1-a) to (I-8-a) are in each case reacted with carbonyl halides of the formula (XIII), if appropriate in the presence of a diluent and if appropriate in the presence of an acid binder.

Suitable diluents for use in the process (I-α) according to the invention are all solvents which are inert toward the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulfoxide and sulfolane. The hydrolytic stability of the acid halide permitting, the reaction can also be carried out in the presence of water.

Suitable acid binders for the reaction according to the process (I-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (I-α) according to the invention may be varied within a relatively wide range. In general, the process is carried out at temperatures between $-20°$ C. and $+150°$ C., preferably between $0°$ C. and $100°$ C.

When carrying out the process (I-α) according to the invention, the starting materials of the formulae (I-1-a) to (I-8-a) and the carbonyl halide of the formula (XIII) are generally each employed in approximately equivalent amounts. However, it is also possible to use a relatively large excess (up to 5 mol) of the carbonyl halide. Work-up is carried out by customary methods.

The process (I-β) is characterized in that compounds of the formulae (I-1-a) to (I-8-a) are reacted with carboxylic anhydrides of the formula (XIV), if appropriate in the presence of a diluent and if appropriate in the presence of an acid binder.

Suitable for use as diluents in the process (I-β) according to the invention are, preferably, those diluents which are also preferred when acid halides are used. Besides, it is also possible for excess carboxylic anhydride to act simultaneously as diluent.

Suitable acid binders for process (I-β), which are added, if appropriate, are preferably those acid binders which are also preferred when acid halides are used.

The reaction temperatures in the process (I-β) according to the invention can be varied within a relatively wide range. In general, the process is carried out at temperatures between $-20°$ C. and $+150°$ C., preferably between $0°$ C. and $100°$ C.

When carrying out the process (I-β) according to the invention, the starting materials of the formulae (I-1-a) to (I-8-a) and the carboxylic anhydride of the formula (XIV) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (J) is characterized in that compounds of the formulae (I-1-a) to (I-a) are in each case reacted with chloroformic esters or chloroformic thioesters of the formula (XV), if appropriate in the presence of a diluent and if appropriate in the presence of an acid binder.

Suitable acid binders for the reaction according to process (J) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (J) according to the invention are all solvents which are inert toward the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulfoxide and sulfolane.

When carrying out the process (J) according to the invention, the reaction temperatures can be varied within a relatively wide range. If the reaction is carried out in the presence of a diluent and an acid binder, reaction temperatures are generally between $-20°$ C. and $+100°$ C., preferably between $0°$ C. and $50°$ C.

The process (J) according to the invention is generally carried out under atmospheric pressure.

When carrying out the process (J) according to the invention, the starting materials of the formulae (I-1-a) to (I-8-a) and the appropriate chloroformic ester or chloroformic thioester of the formula (XIII) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (K) according to the invention is characterized in that compounds of the formulae (I-1-a) to (I-8-a) are in each case reacted with compounds of the formula (XVI) in the presence of a diluent and, if appropriate, in the presence of an acid binder.

In preparation process (K), about 1 mol of chloromonothioformic ester or chlorodithioformic ester of the formula (XVI) is reacted per mole of the starting material of the formulae (I-1-a) to (I-8-a) at from 0 to $120°$ C., preferably from 20 to $60°$ C.

Suitable diluents, which are added, if appropriate, are all inert polar organic solvents, such as ethers, amides, sulfones, sulfoxides, and also halogenated alkanes.

Preference is given to using dimethyl sulfoxide, tetrahydrofuran, dimethylformamide or methylene chloride.

If, in a preferred embodiment, the enolate salt of the compounds (I-1-a) to (I-8-a) is prepared by addition of strong deprotonating agents, such as, for example, sodium hydride or potassium tert-butoxide, the further addition of acid binders may be dispensed with.

If acid binders are used, customary inorganic or organic bases are suitable, by way of example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (L) according to the invention is characterized in that compounds of the formulae (I-1-a) to (I-8-a) are in each case reacted with sulfonyl chlorides of the formula (XVII), if appropriate in the presence of a diluent and if appropriate in the presence of an acid binder.

In preparation process (L), about 1 mol of sulfonyl chloride of the formula (XVII) is reacted per mole of starting material of the formula (I-1-a to I-8-a), at from −20 to 150° C., preferably from 20 to 70° C.

Suitable diluents, which are added, if appropriate, are all inert polar organic solvents, such as ethers, amides, nitriles, sulfones, sulfoxides or halogenated hydrocarbons, such as methylene chloride.

Preference is given to using dimethyl sulfoxide, tetrahydrofuran, dimethylformamide, methylene chloride.

If, in a preferred embodiment, the enolate salt of the compounds (I-1-a) to (I-8-a) is prepared by addition of strong deprotonating agents (such as, for example, sodium hydride or potassium tert-butoxide), the further addition of acid binders may be dispensed with.

If acid binders are used, customary inorganic or organic bases are suitable, by way of example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (M) according to the invention is characterized in that compounds of the formulae (I-1-a) to (I-8-a) are in each case reacted with phosphorus compounds of the formula (XVIII), if appropriate in the presence of a diluent and if appropriate in the presence of an acid binder.

In preparation process (M), to obtain compounds of the formulae (I-1-e) to (I-8-e) 1 to 2, preferably 1 to 1.3, mol of the phosphorus compound of the formula (XVIII) are employed per mole of the compounds (I-1-e) to (I-8-e), at temperatures between −40° C. and 150° C., preferably between −10 and 110° C.

Suitable diluents which are added, if appropriate, are all inert polar organic solvents, such as ethers, amides, nitriles, alcohols, sulfides, sulfones, sulfoxides, etc.

Preference is given to using acetonitrile, dimethyl sulfoxide, tetrahydrofuran, dimethylformamide, methylene chloride.

Suitable acid binders, which are added, if appropriate, are customary inorganic or organic bases, such as hydroxides, carbonates or amines. Sodium hydroxide, sodium carbonate, potassium carbonate, pyridine, triethylamine may be mentioned by way of example.

The reaction can be carried out at atmospheric pressure or under elevated pressure and is preferably carried out at atmospheric pressure. Work-up is carried out by customary methods of organic chemistry. The end products obtained are preferably purified by crystallization, chromatographic purification or by so-called "incipient distillation", i.e. removal of the volatile components under reduced pressure.

The process (N) is characterized in that compounds of the formulae (I-1-a) to (I-8-a) are reacted with metal hydroxides or metal alkoxides of the formula (XIX) or amines of the formula (XX), if appropriate in the presence of a diluent.

Suitable for use as diluents in the process (N) according to the invention are, preferably, ethers, such as tetrahydrofuran, dioxane, diethyl ether, or else alcohols, such as methanol, ethanol, isopropanol, but also water.

The process (N) according to the invention is generally carried out under atmospheric pressure.

The reaction temperatures are generally between −20° C. and 100° C., preferably between 0° C. and 50° C.

The process (O) according to the invention is characterized in that compounds of the formulae (I-1-a) to (I-8-a) are in each case reacted with (O-α) compounds of the formula (XXI), if appropriate in the presence of a diluent and if appropriate in the presence of a catalyst, or (O-β) with compounds of the formula (XXII), if appropriate in the presence of a diluent and if appropriate in the presence of an acid binder.

In preparation process (O-α), about 1 mol of isocyanate of the formula (XXI) is employed per mole of starting material of the formulae (I-1-a) to (I-8-a), at from 0 to 100° C., preferably from 20 to 50° C.

Suitable diluents, which are added, if appropriate, are all inert organic solvents, such as ethers, amides, nitriles, sulfones, sulfoxides.

If appropriate, catalysts may be added to accelerate the reaction. Suitable for use as catalysts are, very advantageously, organotin compounds, such as, for example, dibutyltin dilaurate. The reaction is preferably carried out at atmospheric pressure.

In preparation process (O-β), about 1 mol of carbamoyl chloride of the formula (XXII) is employed per mole of starting material of the formulae (I-1-a) to (I-8-a) at from −20 to 150° C., preferably from 0 to 70° C.

Suitable diluents, which are added, if appropriate, are all inert polar organic solvents, such as ethers, amides, sulfones, sulfoxides or halogenated hydrocarbons.

Preference is given to using dimethyl sulfoxide, tetrahydrofuran, dimethylformamide or methylene chloride.

If, in a preferred embodiment, the enolate salt of the compound (I-1-a) to (I-8-a) is prepared by addition of strong deprotonating agents (such as, for example, sodium hydride or potassium tert-butoxide), the further addition of acid binders may be dispensed with.

If acid binders are used, customary inorganic or organic bases are suitable, by way of example sodium hydroxide, sodium carbonate, potassium carbonate, triethylamine or pyridine.

The reaction may be carried out at atmospheric pressure or under elevated pressure and is preferably carried out at atmospheric pressure. Work-up is carried out by customary methods.

The process (Pα) is characterized in that compounds of the formulae (I-1-a') to (I-8-a') in which A, B, D, $Q^1$, $Q^2$, $Q^3$, $Q^4$, $Q^5$, $Q^6$, X and Y are as defined above and W' preferably represents bromine are reacted with metal iodides (for example sodium iodide, potassium iodide), if appropriate in the presence of a base and a Cu(I) salt (for example CuBr or CuI).

Suitable for use as diluents in the process (Pα) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide, dimethylacetamide and N-methylpyrrolidone, esters, such as methyl acetate, ethyl acetate, propyl acetate, and also alcohols, such as, for example, methanol, ethanol, propanol, isopropanol, butanol and isobutanol.

Suitable bases for carrying out the process (Pα) according to the invention are especially organic bases. Preference is given to using amines, such as, for example, N,N-dimethylethylenediamine, 1,2-diaminocyclohexane.

When carrying out the process (Pα) according to the invention, the reaction temperature can be varied within a relatively wide range. In general, the process is carried out at temperatures between 0° C. and 250° C., preferably between 50° C. and 150° C.

The process (Pα) according to the invention is generally carried out under atmospheric pressure.

When carrying out the process (Pα) according to the invention, the reaction component of the formula (I-1-a') to (I-8-a') is generally reacted with excesses of the metal iodides of up to 20 mol, preferably from 1.1 to 5 mol. The copper(I) salts are generally employed in catalytic amounts; from 0.001 to 0.5 mol, preferably from 0.01 to 0.2 mol. However, they can also be employed in equimolar amounts.

The process (Pβ) is characterized in that compounds of the formulae (I-1-a') to (I-8-a') in which A, B, D, $Q^1$, $Q^2$, $Q^3$, $Q^4$, $Q^5$, $Q^6$, X and Y are as defined above and W' preferably represents bromine are subjected to a halogen/metal exchange with metal organyls and the anion formed is reacted with iodinating agents.

Suitable diluents for use in the process (Pβ) according to the invention are all organic solvents which are inert toward the reaction participants. Preference is given to using hydrocarbons, such as toluene and xylene, furthermore ethers, such as diethyl ether, methyl tert-butyl ether, dibutyl ether, tetrahydrofuran, dioxane, glycol dimethyl ether and diglycol dimethyl ether.

Suitable for use as iodinating agents for carrying out the process (Pβ) are customary reagents, such as iodine, iodine monochloride, iodine monobromide.

When carrying out the process (Pβ) according to the invention, all customary metal organyls can be used for the halogen/metal exchange. Preference is given to using n-butyllithium, sec-butyllithium, tert-butyllithium, phenyllithium.

When carrying out the process (Pβ) according to the invention, the reaction temperature can be varied within a relatively wide range. In general, the process is carried out at temperatures between −120° C. and 50° C., preferably between −78° C. and 30° C.

The process (Pβ) according to the invention is generally carried out under atmospheric pressure.

When carrying out the process (Pβ) according to the invention, the reaction component of the formula (I-1-a') to (I-8-a') is generally reacted with excesses of the metal organyls and the iodinating agents of up to 20 mol, preferably from 1.2 to 5 mol.

The inventive active compounds/active compound combinations, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa*.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp.,

*Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control Protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Aphelenchoides* spp., *Bursaphelenchus* spp., *Ditylenchus dipsaci*, *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

If appropriate, the compounds/active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds/active compound combinations is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds/active compound combinations can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds/active compound combinations with extenders, that is liquid solvents and/or solid carriers, optionally with the use of surfactants, that is emulsifiers and/or dispersants and/or foam-formers.

If the extender used is water, it is also possible to use organic solvents, for example, as auxiliary solvents. Suitable liquid solvents are essentially aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, as well as their ethers and esters, ketones, such as acetone, methyl ethyl ketone, methyl isobutyl ketone or cyclohexanone, strongly polar solvents, such as dimethyl sulfoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulfates, arylsulfonates, or else protein hydrolyzates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound/active compound combinations according to the invention can be present in their commercially available formulations, as well as in the use forms prepared from these formulations, in a mixture with other active compounds such as insecticides, attractants, sterilizers, bactericides, acaricides, nematicides, fungicides, growth-regulating substances, herbicides, safeners, fertilizers or semiochemicals.

Compounds which are suitable as mixing partners are, for example, the following:

Fungicides:

2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-A1; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulfonyl)amino]butanamide; 1-(1-naphthalenyl)-1H-pyrrole-2,5- dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulfate; cufraneb; cuprous oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:

1. Acetylcholine esterase (AChE) inhibitors 1.1 Carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate 1.2 Organophosphates, for example acephate, azamethiphos, azinphos (-methyl, -ethyl), bromophos-ethyl, brom-fenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methyl sulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methi-dathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion 2. Sodium channel modulators/voltage-gated sodium channel blockers 2.1 Pyrethroids, for example acrinathrin, allethrin (d-cis-trans, d-trans), beta-cyfluthrin, bifenthrin, bioallethrin, bioallethrin-S cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (IR isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, trans-fluthrin, ZXI 8901, pyrethrins (pyrethrum)

DDT 2.2 Oxadiazines, for example indoxacarb

Acetylcholine receptor agonists/antagonists 3.1 Chloronicotinyls, for example acetamiprid, clothianidin, dinotefuran, imidacloprid, nitenpyram, nithiazine, thiacloprid, thiamethoxam 3.2 Nicotine, bensultap, cartap Acetylcholine receptor modulators 4.1 Spinosyns, for example spinosad GABA-gated chloride channel antagonists 5.1 Cyclodiene organochlorines, for example camphechlor, chlordane, endosulfan, gamma-HCH, HCH, heptachlor, lindane, methoxychlor 5.2 Fiproles, for example acetoprole, ethiprole, fipronil, pyrafluprole, pyripole, vaniliprole Chloride channel activators 6.1 Mectins, for example avermectin, emamectin, emamectin benzoate, ivermectin, milbemycin Juvenile hormone mimetics, for example diofenolan, epofenonane, fenoxycarb, hydroprene, kinoprene, methoprene, pyriproxifen, triprene Ecdyson agonists/disruptors 8.1 Diacylhydrazines, for example chromafenozide, halofenozide, methoxyfenozide, tebufenozide Chitin biosynthesis inhibitors 9.1 Benzoylureas, for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron 9.2 Buprofezin 9.3 Cyromazine Oxidative phosphorylation inhibitors, ATP disruptors 10.1 Diafenthiuron 10.2 Organotins, for example azocyclotin, cyhexatin, fenbutatin oxide Oxidative phosphorylation decouplers acting by interrupting the H-proton gradient 11.1 Pyrroles, for example chlorfenapyr 11.2 Dinitrophenols, for example binapacyrl, dinobuton, dinocap, DNOC Page-I electron transport inhibitors 12.1 METIs, for example fenazaquin, fenpyroximate, pyrimidifen, pyridaben, tebufenpyrad, tolfenpyrad 12.2 Hydramethylnone 12.3 Dicofol Page-II electron transport inhibitors Rotenone Page-III electron transport inhibitors Acequinocyl, fluacrypyrim Microbial disruptors of the insect gut membrane
*Bacillus thuringiensis* strains
Fat synthesis inhibitors
tetronic acids,
for example spirodiclofen, spiromesifen tetramic acids, for example spirotetramat (CAS Reg. No.: 203313-25-1) and 3-(2,5-dimethylphenyl)-8-methoxy-2-oxo-1-aza-spiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS Reg. No.: 382608-10-8)

carboxamides, for example flonicamid octopaminergic agonists, for example amitraz Inhibitors of magnesium-stimulated ATPase, propargite benzoic acid dicarboxamides, for example flubendiamides nereistoxin analogs for example thiocyclam hydrogen oxalate, thiosultap-sodium Biologicals, hormones or pheromones azadirachtin, *Bacillus* spec., *Beauveria* spec., *codlemone, Metarrhizium* spec.,

*Paecilomyces* spec., *thuringiensin, Verticillium* spec.

Active compounds with unknown or unspecific mechanisms of action 23.1 Fumigants, for example aluminum phosphide, methyl bromide, sulfuryl fluoride 23.2 Antifeedants, for example cryolite, flonicamid, pymetrozine 23.3 Mite growth inhibitors, for example clofentezine, etoxazole, hexythiazox 23.4 Amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as herbicides, fertilizers, growth regulators, safeners, semiochemicals, or else with agents which improve plant properties is also possible.

When used as insecticides in their commercially available formulations and in the use forms prepared from these formulations, the active compounds/active compound combinations according to the invention can furthermore be present in the form of a mixture with synergists. Synergists are compounds by which the activity of the active compounds is increased without it being necessary for the synergist added to be active itself.

When used as insecticides in their commercially available formulations and in the use forms prepared from these formulations, the active compounds/active compound combinations according to the invention can furthermore be present in the form of mixtures with inhibitors which reduce the degradation of the active compound after application in the habitat of the plant, on the surface of parts of plants or in plant tissues.

The active compound content of the use forms prepared from the commercially available formulations can vary within wide ranges. The active compound concentration of the use forms can be from 0.00000001 up to 95% by weight of active compound and is preferably between 0.00001 and 1% by weight.

Application is in a customary manner adapted to suit the use forms.

As already mentioned above, it is possible to treat all plants and their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher harvest yields, higher quality and/or higher nutritional value of the harvested products, better storage characteristics and/or better processability of the harvested products. Further examples of such traits, examples which must be mentioned especially, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, sugar beet, tomatoes, peas and other vegetable varieties, cotton, tobacco, oilseed rape and fruit plants (with the fruits apples, pears, citrus fruits and grapes), with particular emphasis on maize, soybeans, potatoes, cotton, tobacco, and oilseed rape. Traits which are especially emphasized are the increased defense of the plants against insects, arachnids, nematodes and slugs and snails, owing to toxins being formed in the plants, in particular toxins which are generated in the plants by the genetic material of Bacillus thuringiensis (for example by the genes CryIA(a), CryIA(b), CryIA(c), CryIIA, CryIIIA, CryIIIB2, Cry9c Cry2Ab, Cry3Bb and CryIF and their combinations (hereinbelow "Bt plants"). Other traits which are particularly emphasized are the increased defense of plants against fungi, bacteria and viruses by the systemic acquired resistance (SAR), systemins, phytoalexins, elicitors and resistance genes and correspondingly expressed proteins and toxins. Other traits which are especially emphasized are the increased tolerance of the plants to certain herbicidal active compounds, for example imidazolinones, sulfonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize), Boligard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybeans), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula I or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds/active compound combinations according to the invention are not only active against plant, hygiene and stored-product pests, but also, in the veterinary medicine sector, against animal parasites (ectoparasites and endoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the sub-class of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds/active compound combinations of the formula (I) according to the invention are also suitable for controlling arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds/active compound combinations according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (D can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds/active compound combinations according to the invention have a potent insecticidal action against insects which destroy industrial materials.

The following insects may be mentioned by way of example and as being preferred, but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Dermapterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example:

construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flash point of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably o-monochloronaphthalene, are used.

The organic oily or oil-type solvents of low volatility having an evaporation number of above 35 and a flash point of above 30° C., preferably above 45° C., can be partially replaced by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odor-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di(2-ethylhexyl) adipate, the stearates, such as butyl stearate or amyl stearate, the oleates, such as butyl oleate, the glycerol ethers or relatively high molecular weight glycol ethers, glycerol esters and p-toluenesulfonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid, triflumuron, chlothianidin, spinosad, tefluthrin, and fungicides, such as epoxyconazole, hexaconazole, azaconazole, propiconazole, tebuconazole, cyproconazole, metconazole, imazalil, dichlorfluanid, tolylfluanid, 3-iodo-2-propynyl butylcarbamate, N-octyl-isothiazolin-3-one and 4,5-dichloro-N-octylisothiazolin-3-one.

The compounds according to the invention can at the same time be employed for protecting objects which come into contact with saltwater or brackish water, in particular hulls, screens, nets, buildings, moorings and signaling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulfides, tri-n-butyltin laurate, tri-n-butyltin chloride, copper(I) oxide, triethyltin chloride, tri-n-butyl-(2-phenyl-4-chlorophenoxy)tin, tributyltin oxide, molybdenum disulfide, antimony oxide, polymeric butyl titanate, phenyl(bispyridine) bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:

algicides such as
2-tert-butylamino-4-cyclopropylamino-6-methylthio-1,3, 5-triazine, dichlorophen, diuron, endothal, fentin acetate, isoproturon, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propynyl butylcarbamate, tolylfluanid and azoles such as azaconazole, cyproconazole, epoxyconazole, hexaconazole, metconazole, propiconazole and tebuconazole;

molluscicides such as
fentin acetate, metaldehyde, methiocarb, niclosamid, thiodicarb and trimethacarb, Fe chelates;

or conventional antifouling active compounds such as
4,5-dichloro-2-octyl-4-isothiazolin-3-one, diiodomethylparatryl sulfone, 2-(N,N-dimethyl-thiocarbamoylthio)-5-nitrothiazyl, potassium, copper, sodium and zinc salts of 2-pyridinethiol
1-oxide, pyridine-triphenylborane, tetrabutyldistannoxane, 2,3,5,6-tetrachloro-4-(methylsulfonyl)-pyridine, 2,4,5, 6-tetrachloroisophthalonitrile, tetramethylthiuram disulfide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in saltwater. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyci-*

*phagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

They are used in the household insecticides sector alone or in combination with other suitable active compounds such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds/active compound combinations according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds/active compound combinations according to the invention can be used, for example, in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds/active compound combinations according to the invention is in no way restricted to these genera, but extends in the same manner to other plants.

Depending on the concentration, the active compounds/active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantations and hop fields, on lawns, turf and pastureland, and for the selective control of weeds in annual crops.

The compounds of the formula (I)/active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds/active compound combinations according to the invention can also be employed for controlling animal pests and fungal or bacterial plant diseases. If appropriate, they can also be used as intermediates or precursors for the synthesis of other active compounds.

The active compounds/active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian blue, and organic colorants, such as alizarin colorants, azo colorants and metal phthalocyanine colorants, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds/active compound combinations according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example
acetochlor, acifluorfen (-sodium), aclonifen, alachlor, alloxydim (-sodium), ametryne, amicarbazone, amidochlor, amidosulfuron, aminopyralid, anilofos, asulam, atrazine, azafenidin, azimsulfuron, beflubutamid, benazolin (-ethyl), benfuresate, bensulfuron (-methyl), bentazone, bencarbazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, KIH 485, lactofen, lenacil, linuron, MCPA, mecoprop, mefenacet, mesosulfuron, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrimisulfan, pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thifensulfuron (-methyl), thiobencarb, tiocarbazil, tropramezone, tralkoxydim, triallate, triasulfuron, tribenuron (-methyl), triclopyr, tridiphane, trifluralin, trifloxysulfuron, triflusulfuron (-methyl), tritosulfuron and

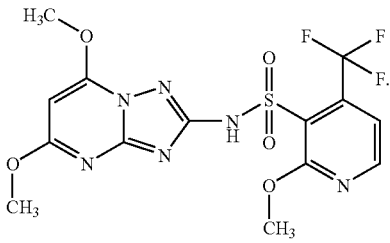 [SMILES: COc1cc(OC)n2nc(NS(=O)(=O)c3c(C(F)(F)F)ccnc3OC)nc2n1]

A mixture with other known active compounds, such as fungicides, insectides, acaricides, nematicides, bird repellents, plant nutrients and soil conditioners, is also possible.

The active compounds/active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds/active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are compatible with plants (for example the commercial preparation "Rako Binol"), or ammonium salts, such as, for example, ammonium sulfate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by watering, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Preparation and use of the active compounds according to the invention are illustrated in the examples below.

PREPARATION EXAMPLES

Example I-1-a-1

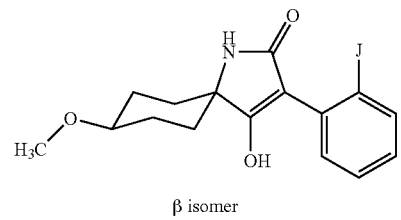

β isomer

Under argon, 5.24 g of potassium tert-butoxide-95% pure- (44.4 mmol) are initially charged in 10 ml of dimethylacetamide in a 100 ml three-necked flask fitted with thermometer and reflux condenser.

At 40 to 50° C., 8.7 g of the compound according to Example II-1 (20.2 mmol) in 10 ml of dimethylacetamide are added dropwise. The mixture is stirred at 60° C. for 1 h and monitored by thin-layer chromatography during this time.

The reaction solution is then stirred into 100 ml of ice-water, the pH is adjusted to 2 using conc. HCl and the precipitate is filtered off with suction. The product is then purified by column chromatography on silica gel (dichloromethane:ethyl acetate 5:3).

Yield 7.8 g (94% of theory), m.p. 225.6° C.

Example I-1-a-3

Process P-β

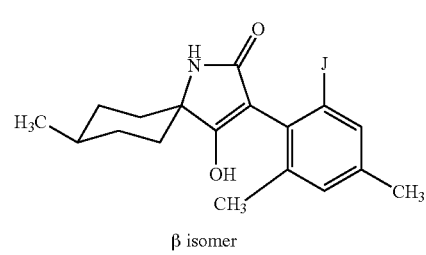

β isomer

Under argon, 1.413 g (3 mmol) of example I-1-c-4 from WO 97/02243 are initially charged in 30 ml of anhydrous tetrahydrofuran in a 100 ml three-necked flask. At −78° C., 2.64 ml of n-butyllithium (2.5 m in n-hexane) are added dropwise. After 15 min of stirring, 0.761 g (3 mmol) of iodine in 5 ml of anhydrous tetrahydrofuran is added dropwise at −78° C., and the mixture is allowed to slowly warm to room temperature. The solvent is evaporated and the residue is pre-purified by flash chromatography on silica gel using the mobile phase methylene chloride/acetone 5:1. The product-containing fractions were combined, the solvent was removed under reduced pressure and the residue 250 mg was purified by reversed-phase chromatography using acetonitrile/water (gradient program 70:30→10:90). Yield: 40 mg (≙ 2.7% of theory) m.p. 245° C.

The following compounds of the formula (I-1-a) are obtained analogously to example (I-1-a-1) and in accordance with the general statements on the preparation

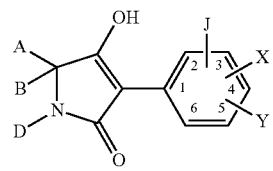

(I-1-a)

| Ex. No. | J | X | Y | D | A | B | m.p. ° C. | Isomer |
|---|---|---|---|---|---|---|---|---|
| I-1-a-2 | 4-J | 2-C$_2$H$_5$ | 6-CH$_3$ | H | —(CH$_2$)$_2$—CHOCH$_3$—(CH$_2$)$_2$— | | 262 | β |
| I-1-a-3 | 2-J | 4-CH$_3$ | 6-CH$_3$ | H | —(CH$_2$)$_2$—CHCH$_3$—(CH$_2$)$_2$— | | 245 | β |
| I-1-a-4 | 2-J | 4-Cl | 6-CH$_3$ | H | —(CH$_2$)$_2$—CHOCH$_3$—(CH$_2$)$_2$— | | 295 | β |
| I-1-a-5 | 2-J | 5-CH$_3$ | H | H | —(CH$_2$)$_2$—CHOCH$_3$—(CH$_2$)$_2$— | | 222 | β |
| I-1-a-6 | 2-J | 5-CH$_3$ | H | H | —(CH$_2$)$_2$—O—(CH$_2$)$_2$— | | Decomposition | — |
| I-1-a-7 | 2-J | 4-Cl | 6-C$_2$H$_5$ | H | —(CH$_2$)$_2$—O—(CH$_2$)$_2$— | | 324 | — |
| I-1-a-8 | 2-J | 4-Cl | 6-C$_2$H$_5$ | H | —(CH$_2$)$_2$—CHOCH$_3$—(CH$_2$)$_2$— | | *1.02 (t, 3H, ArCH$_2$C$\underline{H}_3$), 7.31, (d. 1H, Ar—$\underline{H}$), 7.74 (d, 1H, Ar—$\underline{H}$), | β |
| I-1-a-9 | 2-J | 4-Cl | 6-CH$_3$ | H | —(CH$_2$)$_2$—O—(CH$_2$)$_2$— | | *3.83-3.88 (m, 2H, O-CH$_2$), 7.35, (d, 1H, Ar—$\underline{H}$), 7.74 (d, 1H, Ar—$\underline{H}$), | — |
| I-1-a-10 | 3-J | 6-CH$_3$ | H | H | —(CH$_2$)$_2$—CHOCH$_3$—(CH$_2$)$_2$— | | 248 | β |
| I-1-a-11 | 4-J | 2-C$_2$H$_5$ | 6-CH$_3$ | H | —(CH$_2$)$_2$—O—(CH$_2$)$_2$— | | 300 | — |
| I-1-a-12 | 4-J | 2-C$_2$H$_5$ | 6-CH$_3$ | H | CH$_3$ | CH$_3$ | 254 | — |
| I-1-a-13 | 4-J | 2-C$_2$H$_5$ | 6-CH$_3$ | H | ▷ | CH$_3$ | *2.05 (d, 3H, ArC$\underline{H}_3$), 1.20 (m, 1H, CH (C$_1$-cyclopropyl)) | — |
| I-1-a-14 | 4-J | 2-C$_2$H$_5$ | 6-CH$_3$ | H | n-C$_3$H$_7$ | CH$_3$ | *2.05 (d, 3H, ArC$\underline{H}_3$), 1.31 (d, 3H, CH$_3$ tetramic acid) | — |
| I-1-a-15 | 4-J | 2-C$_2$H$_5$ | 6-CH$_3$ | —CH—CH—CH$_2$— \\ (CH$_2$)$_4$ / | | H | *2.03 (s, 3H, ArC$\underline{H}_3$), 4.34 (dd, 1H, N-C$\underline{H}$ tetramic acid) | — |
| I-1-a-16 | 4-J | 2-C$_2$H$_5$ | 6-CH$_3$ | H | —(CH$_2$)$_5$— | | *2.40 (m, 2H, Ar—C$\underline{H}_2$), 2.05 (s, 3H, Ar—C$\underline{H}_3$) 1.05 (t, 3H, ArCH$_2$C$\underline{H}_3$) | — |
| I-1-a-17 | 4-J | 2-C$_2$H$_5$ | 6-CH$_3$ | H | —(CH$_2$)$_2$—CHCH$_3$—(CH$_2$)$_2$— | | *7.4 (s, br, 2H, Ar—$\underline{H}$) 1.10 (tr, 3H, ArC$\underline{H}_2$—CH$_3$) 0.95 ("tr", 3H, CHCH$_3$) | — |
| I-1-a-18 | 4-J | 2-CH$_3$ | 6-CH$_3$ | H | —(CH$_2$)$_2$—CHOCH$_3$—(CH$_2$)$_2$— | | 295 | β |
| I-1-a-19 | 4-J | 2-CH$_3$ | 6-CH$_3$ | H | —(CH$_2$)$_2$—O—(CH$_2$)$_2$— | | >300 | — |
| I-1-a-20 | 4-J | 2-C$_2$H$_5$ | 6-Cl | H | —(CH$_2$)$_2$—O—(CH$_2$)$_2$— | | 274 | — |
| I-1-a-21 | 4-J | 2-CH$_3$ | 6-CH$_3$ | H | —CH$_2$—CHOC$_4$H$_9$—(CH$_2$)$_3$— | | 182 | β |
| I-1-a-22 | 4-J | 2-CH$_3$ | 6-Cl | H | —(CH$_2$)$_2$—O—(CH$_2$)$_2$— | | >300 | — |
| I-1-a-23 | 4-J | 2-C$_2$H$_5$ | 6-CH$_3$ | H | —CH$_2$—CHOC$_4$H$_9$—(CH$_2$)$_3$— | | 166 | β |
| I-1-a-24 | 4-J | 2-C$_2$H$_5$ | 6-Cl | H | —(CH$_2$)$_2$—CHOCH$_3$—(CH$_2$)$_2$— | | >300 | β |
| I-1-a-25 | 4-J | 2-CH$_3$ | 6-Cl | H | —(CH$_2$)$_2$—CHOCH$_3$—(CH$_2$)$_2$— | | 299 | β |
| I-1-a-26 | 4-J | 2-C$_2$H$_5$ | 6-CH$_3$ | H | i-C$_3$H$_7$ | CH$_3$ | 80 | — |
| I-1-a-27 | 4-J | 2-C$_2$H$_5$ | 6-CH$_3$ | H | i-C$_4$H$_9$ | CH$_3$ | 225 | — |

*$^1$H-NMR (400 MHZ, d$_6$-DMSO): shifts δ in ppm.

Example I-1-b-1

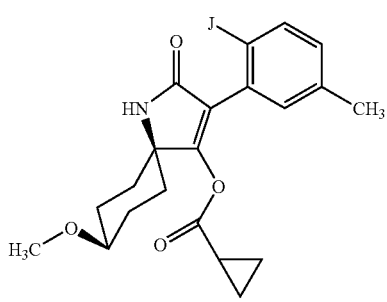

Under an atmosphere of protective gas, 0.48 g of the compound of example I-1-a-5 is initially charged in 30 ml of ethyl acetate, 0.15 ml of triethylamine and 10 mg of Steglich base are added and 0.115 g of cyclopropylcarbonyl chloride in 5 ml of ethyl acetate is added dropwise under reflux and the mixture is stirred further under reflux.

After the reaction has ended (monitored by thin-layer chromatography) the product is purified by flash column separation on silica gel (mobile phase ethyl acetate)

Yield: 0.4 g (75% of theory), m.p. 167° C.

The following compounds of the formula (I-1-b) are obtained analogously to example (I-1-b-1) and in accordance with the general statements on the preparation (I-1-b)

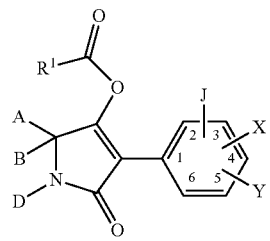

| Ex. No. | J | X | Y | D | A | B | $R^1$ | m.p. ° C. | Isomer |
|---|---|---|---|---|---|---|---|---|---|
| I-1-b-2 | 2-J | 5-$CH_3$ | H | H | —$(CH_2)_2$—$CHOCH_3$—$(CH_2)_2$— | | i-$C_3H_7$ | **0.95, 1.01 (2s, 6H, CH($\underline{CH_3}$)$_2$) 2.67, (m, 1H, $\underline{CH}$ ($CH_3$)$_2$) 7.71, (d, 1H, Ar$\underline{H}$), | β |
| I-1-b-3 | 2-J | 4-Cl | 6-$C_2H_5$ | H | —$(CH_2)_2$—$CHOCH_3$—$(CH_2)_2$— | | $H_3C$—O—$CH_2$— | *1.20 (t, 3H, Ar—$CH_2\underline{CH_3}$), 3.25, (m, 1H, $\underline{CH}$—$OCH_3$), 7.25, 7.70, (2d, 2H, Ar-H), | β |
| I-1-b-4 | 2-J | 4-Cl | 6-$C_2H_5$ | H | —$(CH_2)_2$—O—$(CH_2)_2$— | | $H_3C$—O—$CH_2$— | *4.11 (q, 2H, $OCH_2$), 3.64, (dt, 2H, $OCH_2$ (tetrahydropyran)), 2.61 (m, 2H, Ar—$CH_2$), | — |
| I-1-b-5 | 4-J | 2-$C_2H_5$ | 6-$CH_3$ | H | —$(CH_2)_2$—O—$(CH_2)_2$— | | i-$C_3H_7$ | *1.15 (t, 3H, Ar—$CH\underline{CH_3}$), 2.55, (s, 1H, $\underline{CH}$ ($CH_3$)$_2$) 4.00 (m, 2H, O—$\underline{CH_2}$) | — |

| Bsp.-Nr. | J | X | Y | D | A | B | $R^1$ | Fp ° C. | Isomer |
|---|---|---|---|---|---|---|---|---|---|
| I-1-b-6 | 4-J | 2-$C_2H_5$ | 6-$CH_3$ | H | $C_3H_7$ | $CH_3$ | i-$C_3H_7$ | *1.40 (s, 3H, N—C—$CH_3$), 2.55, (m, 1H, CH($CH_3$)$_2$) 7.4, 7.43 (2s, 2H, Ar—$\underline{H}$) | — |
| I-1-b-7 | 4-J | 2-$CH_3$ | 6-$CH_3$ | H | —$CH_2$—CH—$OC_4H_9$—$(CH_2)_3$— | | $H_3C$—O—$CH_2$— | 168-170 | β |
| I-1-b-8 | 4-J | 2-$CH_3$ | 6-$CH_3$ | H | —$CH_2$—$CHOC_4H_9$—$(CH_2)_3$— | | cyclopropyl | *3.43 (m, 3H, $O\underline{CH}$, $O\underline{CH_2}$), 2.21 (s, 3H, Ar—$\underline{CH_3}$) 0.83 (m, 4H, cyclopropyl $\underline{H}$) | β |
| I-1-b-9 | 4-J | 2-$CH_3$ | 6-$CH_3$ | H | —$CH_2$—$CHOC_4H_9$—$(CH_2)_3$— | | Cl—$CH_2$— | 185 | β |
| I-1-b-10 | 4-J | 2-$CH_3$ | 6-$CH_3$ | H | —$CH_2$—$CHOC_4H_9$—$(CH_2)_3$— | | 3-Cl-4-methylphenyl | 245 | β |
| I-1-b-11 | 4-J | 2-$C_2H_5$ | 6-$CH_3$ | H | —$(CH_2)_2$—O—$(CH_2)_2$— | | $H_3C$—O—$CH_2$— | *4.04 (m, 4H, 2 × $O\underline{CH_2}$), 2.18 (s, 3H, Ar—$\underline{CH_3}$) | — |
| I-1-b-12 | 4-J | 2-$C_2H_5$ | 6-Cl | H | —$(CH_2)_2$—O—$(CH_2)_2$— | | $H_3C$—O—$CH_2$— | *4.13 (q, 2H, $O\underline{CH_2}$), 2.64 (q, 2H, Ar—$\underline{CH_2}$) | — |
| I-1-b-13 | 4-J | 2-$C_2H_5$ | 6-$CH_3$ | H | —$CH_2$—$CHOC_4H_9$—$(CH_2)_3$— | | i-$C_3H_7$ | *3.45 (m, 3H, OCH, $O\underline{CH_2}$), 2.52 (sept, 1H, CH($CH_3$)$_2$) | β |
| I-1-b-14 | 4-J | 2-$C_2H_5$ | 6-$CH_3$ | H | i-$C_3H_7$ | $CH_3$ | i-$C_3H_7$ | 130 | — |
| I-1-b-15 | 4-J | 2-$C_2H_5$ | 6-$CH_3$ | H | —$CH_2$—$CHOC_4H_9$—$(CH_2)_3$— | | $H_3C$—O—$CH_2$— | *3.98 (m, 2H, $O\underline{CH_2}$), 3.45 (m, 3H, OCH, $O\underline{CH_2}$) 2.20 (s, 3H, Ar—$\underline{CH_3}$) | β |
| I-1-b-16 | 4-J | 2-$C_2H_5$ | 6-$CH_3$ | H | —$(CH_2)_5$— | | $H_3C$—O—$CH_2$— | 201 | — |

-continued

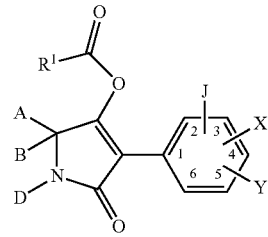

(I-1-b)

| Ex. No. | J | X | Y | D | A | B | R¹ | m.p. °C | Isomer |
|---|---|---|---|---|---|---|---|---|---|
| I-1-b-17 | 4-J | 2-C₂H₅ | 6-CH₃ | H | —(CH₂)₅— | | i-C₃H₇ | 217 | — |
| I-1-b-18 | 4-J | 2-C₂H₅ | 6-CH₃ | H | CH₃ | CH₃ | i-C₃H₇ | 137 | — |
| I-1-b-19 | 4-J | 2-C₂H₅ | 6-CH₃ | H | —(CH₂)₅— | | t-C₄H₉ | 206 | — |
| I-1-b-20 | 4-J | 2-C₂H₅ | 6-CH₃ | H | i-C₃H₇ | CH₃ | H₃C—O—CH₂— | *4.05 (dd, 2H, OC$\underline{H}_2$) 3.20 (s, 3H, OCH₃) 1.50 (d, 3H, CH₃) | — |
| I-1-b-21 | 4-J | 2-C₂H₅ | 6-CH₃ | H | CH₃ | CH₃ | H₃C—O—CH₂— | 165 | — |
| I-1-b-22 | 4-J | 2-C₂H₅ | 6-CH₃ | H | i-C₃H₇ | CH₃ | i-C₃H₇ | 130 | — |

*¹H-NMR (300 MHz/400 MHz, CDCl₃): shifts δ in ppm.
**¹H-NMR (400 MHz, d₆-DMSO): shifts δ in ppm

Example I-1-c-1

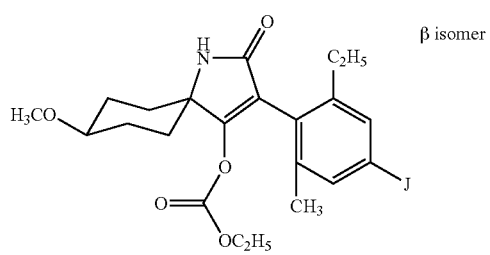

β isomer

Under argon, 0.66 g (1.5 mmol) of example I-1-a-2 is initially charged in 20 ml of anhydrous methylene chloride in a 100 ml three-necked flask, 0.21 ml (1.5 mmol) of triethylamine is added and 0.14 ml (1.5 mmol) of ethyl chloroformate is added dropwise at 20° C. The mixture is stirred for 4 hours, the solvent is evaporated under reduced pressure and the residue is chromatographed on silica gel using the mobile phase methylene chloride/ethyl acetate 10:1.

Yield: 0.4 g ($\hat{=}$ 43% of theory) m.p. 198° C.

The following compounds of the formula (I-1-c) are obtained analogously to example (I-1-c-1) and in accordance with the general statements on the preparation

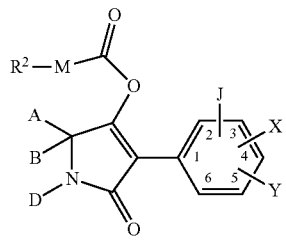

(I-1-c)

| Ex. No. | J | X | Y | D | A | B | M | R² | m.p. °C | Isomer |
|---|---|---|---|---|---|---|---|---|---|---|
| I-1-c-2 | 2-J | 5-CH₃ | H | H | —(CH₂)₂—CHOCH₃—(CH₂)₂— | | O | C₆H₅—CH₂— | 152 | β |
| I-1-c-3 | 2-J | 4-Cl | 6-CH₃ | H | —(CH₂)₂—CHOCH₃—(CH₂)₂— | | O | C₂H₅ | 186 | β |
| I-1-c-4 | 2-J | 5-CH₃ | H | H | —(CH₂)₂—CHOCH₃—(CH₂)₂— | | O | C₂H₅ | Wax | β |
| I-1-c-5 | 2-J | 4-Cl | 6-C₂H₅ | H | —(CH₂)₂—O—(CH₂)₂— | | O | C₂H₅ | *4.11 (q, 2H, O—C$\underline{H}_2$), 4.03, (m, 2H, OC$\underline{H}_2$) 2.20 (s, 3H, Ar—C$\underline{H}_3$) | — |
| I-1-c-6 | 2-J | 4-Cl | 6-C₂H₅ | H | —(CH₂)₂—CHOCH₃—(CH₂)₂— | | O | C₂H₅ | *4.11 (q, 2H, O—C$\underline{H}_2$), 3.39, (s, 3H, OC$\underline{H}_3$) 2.61 (q, 2H, Ar—C$\underline{H}_2$) | β |
| I-1-c-7 | 3-J | 6-CH₃ | H | H | —(CH₂)₂—CHOCH₃—(CH₂)₂— | | O | C₂H₅ | Wax | β |
| I-1-c-8 | 4-J | 2-CH₃ | 6-CH₃ | H | —(CH₂)₂—CHOCH₃—(CH₂)₂— | | O | C₂H₅ | 208 | β |
| I-1-c-9 | 4-J | 2-CH₃ | 6-Cl | H | —(CH₂)₂—O—(CH₂)₂— | | O | C₂H₅ | 214 | — |
| I-1-c-10 | 4-J | 2-C₂H₅ | 6-CH₃ | H | n-C₃H₇ | CH₃ | O | C₂H₅ | *4.02 (m, 2H, OC$\underline{H}_2$), 2.21 (d, 3H, ArC$\underline{H}_3$) 1.46 (s, 3H, C$\underline{H}_3$) | — |

-continued

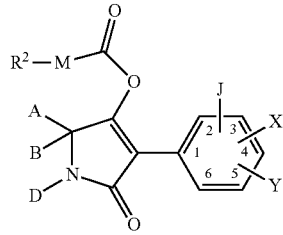

(I-1-c)

| Ex. No. | J | X | Y | D | A | B | M | R² | m.p. ° C. | Isomer |
|---|---|---|---|---|---|---|---|---|---|---|
| I-1-c-11 | 4-J | 2-$C_2H_5$ | 6-$CH_3$ | H | (cyclopropyl) | $CH_3$ | O | $C_2H_5$ | *4.05 (m, 2H, O$CH_2$), 2.21 (d, 3H, Ar$CH_3$) 1.51 (s, 3H, $CH_3$) | — |
| I-1-c-12 | 4-J | 2-$C_2H_5$ | 6-$CH_3$ | H | —$(CH_2)_2$—O—$(CH_2)_2$— | | O | $C_2H_5$ | *4.07 (q, 2H, O$CH_2$), 4.00 (m, 2H, O$CH_2$) 2.47 (q, 2H, Ar—$CH_2$ | — |
| I-1-c-13 | 4-J | 2-$C_2H_5$ | 6-Cl | H | —$(CH_2)_2$—O—$(CH_2)_2$— | | O | $C_2H_5$ | *4.11 (q, 2H, O$CH_2$), 4.03 (m, 2H, O$CH_2$) 2.61 (q, 2H, Ar—$CH_2$) | — |
| I-1-c-14 | 4-J | 2-$CH_3$ | 6-$CH_3$ | H | —$CH_2$—CHO$C_4H_9$—$(CH_2)_3$— | | O | $C_6H_5$—$CH_2$— | *5.00 (q, 2H, O$CH_2$), 3.43 (m, 3H, OCH, O$CH_2$) 2.14 (s, 3H, Ar—$CH_3$) | β |
| I-1-c-15 | 4-J | 2-$CH_3$ | 6-$CH_3$ | H | —$CH_2$—CHO$C_4H_9$—$(CH_2)_3$— | | O | $CH_2$=CH—$CH_2$— | *4.38 (d, 2H, O$CH_2$), 3.37 (m, 3H, O$CH$, O$CH_2$) 2.13 (s, 3H, Ar—$CH_3$) | β |
| I-1-c-16 | 4-J | 2-$CH_3$ | 6-$CH_3$ | H | —$CH_2$—CHO$C_4H_9$—$(CH_2)_3$— | | O | $C_2H_5$ | *4.04 (q, 2H, O—$CH_2$), 3.43 (m, 3H, O$CH$, O$CH_2$) 2.17 (s, 3H, Ar—$CH_3$)— | β |
| I-1-c-17 | 4-J | 2-$C_2H_5$ | 6-$CH_3$ | H | —$(CH_2)_5$— | | O | $C_2H_5$ | 188 | — |
| I-1-c-18 | 4-J | 2-$C_2H_5$ | 6-$CH_3$ | H | $CH_3$ | $CH_3$ | O | $C_2H_5$ | *4.05 (q, 2H, O—$CH_2$), 2.20 (s, 3H, Ar$CH_3$) 1.50 (2s, 6H, 2 × $CH_3$)— | — |
| I-1-c-19 | 4-J | 2-$C_2H_5$ | 6-$CH_3$ | H | i-$C_4H_9$ | $CH_3$ | O | $C_2H_5$ | *4.00 (m, 2H, O—$CH_2$), 2.50 (m, 2H, Ar$CH_2$) 2.20 (d, 3H, Ar—$CH_3$)— | — |
| I-1-c-20 | 4-J | 2-$CH_3$ | 6-$CH_3$ | H | —$(CH_2)_2$—O—$(CH_2)_2$— | | O | $C_2H_5$ | 216 | — |

*¹H-NMR (400 MHz, CDCl₃): shifts δ in ppm.

Example II-1

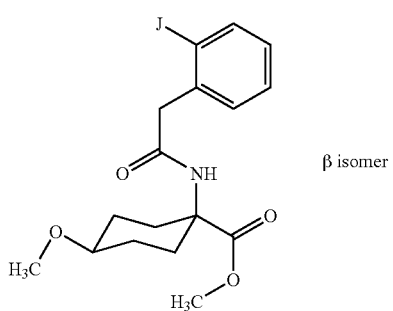

β isomer

Under argon, 5.1 g of methyl cis-1-amino-4-methoxycyclohexanecarboxylate hydrochloride (0.0226 mol) are initially charged under argon in 50 ml of anhydrous tetrahydrofuran in a 100 ml three-necked flask fitted with thermometer and reflux condenser. At 20° C., 6.3 ml (0.0452 mol) of triethylamine are added dropwise. The mixture is stirred for 5 min, and 5.4 g of 2-iodophenylacetic acid (0.0205 mol) are added at 20° C. After 15 min, 4.3 ml of triethylamine (0.0308 mol) are added dropwise, immediately followed by 1.15 ml of phosphorus oxychloride; the solution should boil gently. The mixture is stirred under reflux for another 30 min. After cooling and removal of the solvent under reduced pressure, the product is purified by column chromatography on silica gel (dichloromethane:ethyl acetate 3:1)

Yield: 8.7 g (96% of theory), m.p. 152° C.

Example II-25

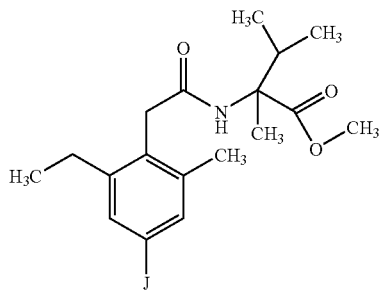

1.8 g (4.5 mmol) of the compound of example XXIX-1 in 20 ml of methylene chloride are added dropwise to 1.4 ml of concentrated sulfuric acid, and the mixture is stirred at an external temperature of 30-40° C. for 2 hours. 3.3 ml of methanol are then added dropwise, the mixture is stirred at an external temperature of 40-70° C. for 4 hours, allowed to stand overnight and stirred at 40 to 70° C. for a further 3 hours. The reaction solution is then poured onto ice/H$_2$O and extracted with dichloromethane, and the extracts are washed with sat. NaHCO$_3$ solution, dried and concentrated using a rotary evaporator.

$^1$H-NMR (CDCl$_3$ 300 MHz): δ=7.40 (s, 2H, Ar—H), 3.65 (s, 3H, OCH$_3$), 3.55 (s, 2H, CH$_2$) 1.90 (sept, 1H, CH(CH$_3$)$_2$) ppm.

The following compounds of the formula (II) are obtained analogously to examples (II-1) and (II-25) and in accordance with the general statements on the preparation

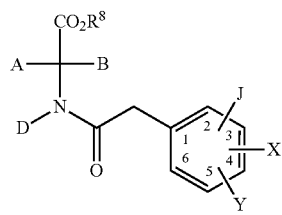

(II)

| Ex. No. | J | X | Y | D | A | B | R$^8$ | m.p. ° C. | Isomer |
|---|---|---|---|---|---|---|---|---|---|
| II-2 | 4-J | 2-C$_2$H$_5$ | 6-CH$_3$ | H | —(CH$_2$)$_2$—CHOCH$_3$—(CH$_2$)$_2$— | | CH$_3$ | 138 | β |
| II-3 | 2-J | 4-Cl | 6-CH$_3$ | H | —(CH$_2$)$_2$—CHOCH$_3$—(CH$_2$)$_2$— | | CH$_3$ | 151 | β |
| II-4 | 2-J | 4-Cl | 6-C$_2$H$_5$ | H | —(CH$_2$)$_2$—CHOCH$_3$—(CH$_2$)$_2$— | | CH$_3$ | 147 | β |
| II-5 | 2-J | 5-CH$_3$ | H | H | —(CH$_2$)$_2$—CHOCH$_3$—(CH$_2$)$_2$— | | CH$_3$ | 157 | β |
| II-6 | 2-J | 4-Cl | 6-CH$_3$ | H | —(CH$_2$)$_2$—O—(CH$_2$)$_2$— | | CH$_3$ | 187 | — |
| II-7 | 2-J | 4-Cl | 6-C$_2$H$_5$ | H | —(CH$_2$)$_2$—O—(CH$_2$)$_2$— | | CH$_3$ | 164 | — |
| II-8 | 2-J | 5-CH$_3$ | H | H | —(CH$_2$)$_2$—O—(CH$_2$)$_2$— | | CH$_3$ | 154 | — |
| II-9 | 2-J | 4-Cl | 6-CH$_3$ | H | —CH$_2$—CHOC$_4$H$_9$—(CH$_2$)$_3$— | | CH$_3$ | 131 | β |
| II-10 | 3-J | 6-CH$_3$ | H | H | —(CH$_2$)$_2$—CHOCH$_3$—(CH$_2$)$_2$— | | CH$_3$ | 138 | β |
| II-11 | 4-J | 2-C$_2$H$_5$ | 6-CH$_3$ | H | —(CH$_2$)$_2$—O—(CH$_2$)$_2$— | | CH$_3$ | 163 | — |
| II-12 | 4-J | 2-C$_2$H$_5$ | 6-CH$_3$ | H | CH$_3$ | CH$_3$ | CH$_3$ | 169 | — |
| II-13 | 4-J | 2-C$_2$H$_5$ | Cl | H | —(CH$_2$)$_2$—CHOCH$_3$—(CH$_2$)$_2$— | | CH$_3$ | 134 | β |
| II-14 | 4-J | 2-C$_2$H$_5$ | 6-CH$_3$ | H | —(CH$_2$)$_2$—CHOCH$_3$—(CH$_2$)$_2$— | | CH$_3$ | 169 | β |
| II-15 | 4-J | 2-C$_2$H$_5$ | 6-Cl | H | —(CH$_2$)$_2$—O—(CH$_2$)$_2$— | | CH$_3$ | 165 | — |
| II-16 | 4-J | 2-C$_2$H$_5$ | 6-CH$_3$ | H | —(CH$_2$)$_2$—O—(CH$_2$)$_2$— | | CH$_3$ | 173 | — |
| II-17 | 4-J | 2-CH$_3$ | 6-CH$_3$ | H | —CH$_2$CHOC$_4$H$_9$—(CH$_2$)$_3$— | | CH$_3$ | 172 | β |
| II-18 | 4-J | 2-CH$_3$ | 6-Cl | H | —(CH$_2$)$_2$—O—(CH$_2$)$_2$— | | CH$_3$ | 173 | — |
| II-19 | 4-J | 2-CH$_3$ | 6-Cl | H | —(CH$_2$)$_2$—CHOCH$_3$—(CH$_2$)$_2$— | | CH$_3$ | 157 | β |
| II-20 | 4-J | 2-C$_2$H$_5$ | 6-CH$_3$ | H | —CH$_2$—CHOC$_4$H$_9$—(CH$_2$)$_3$— | | CH$_3$ | 131 | β |
| II-21 | 4-J | 2-CH$_3$ | 6-Cl | H | —CH$_2$—CHOC$_4$H$_9$—(CH$_2$)$_3$— | | CH$_3$ | 163 | β |
| II-22 | 4-J | 2-C$_2$H$_5$ | 6-Cl | H | —CH$_2$—CHOC$_4$H$_9$—(CH$_2$)$_3$— | | CH$_3$ | 119 | β |
| II-23 | 4-J | 2-C$_2$H$_5$ | 6-CH$_3$ | —CH—CH—CH$_2$— with (CH$_2$)$_4$ bridge | | H | CH$_3$ | *4.24 (dd, 1H, N—CH), 3.57 (s, 3H, OCH$_3$), 2.11 (s, 3H, Ar—CH$_3$) | Mixture |
| II-24 | 4-J | 2-C$_2$H$_5$ | 6-CH$_3$ | H | —(CH$_2$)$_5$— | | CH$_3$ | 144 | — |
| II-25 | 4-J | 2-C$_2$H$_5$ | 6-CH$_3$ | H | i-C$_3$H$_7$ | CH$_3$ | CH$_3$ | oil | — |
| II-26 | 4-J | 2-C$_2$H$_5$ | 6-CH$_3$ | H | —(CH$_2$)$_2$—CHCH$_3$—(CH$_2$)$_2$— | | CH$_3$ | 130 | β |
| II-27 | 4-J | 2-C$_2$H$_5$ | 6-CH$_3$ | H | i-C$_4$H$_9$ | CH$_3$ | CH$_3$ | 143 | — |

Example XXIX-1

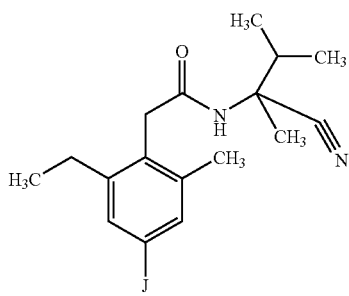

1.7 g (5.59 mmol) of 4-iodo-2-ethyl-6-methylphenylacetic acid are initially charged in 25 ml of tetrahydrofuran, 2 ml of triethylamine and 0.627 g (5.59 mmol) of 2-amino-2-methylisobutyronitrile are added, the mixture is stirred at room temperature for 15 minutes, 1 ml of triethylamine is added followed by the dropwise addition of 0.6 ml of phosphorus oxychloride such that the mixture boils gently. The mixture is stirred under reflux for 30 minutes, concentrated on a rotary evaporator and worked up with ethyl acetate/water, and the organic phase is dried with sodium sulfate, stirred with silica gel, filtered off and concentrated using a rotary evaporator.

Yield: 1.82 g (74% of theory), m.p. 186° C.

The following compounds of the formula (XXIX) are obtained analogously to example (XXIX-1) and in accordance with the general statements on the preparation

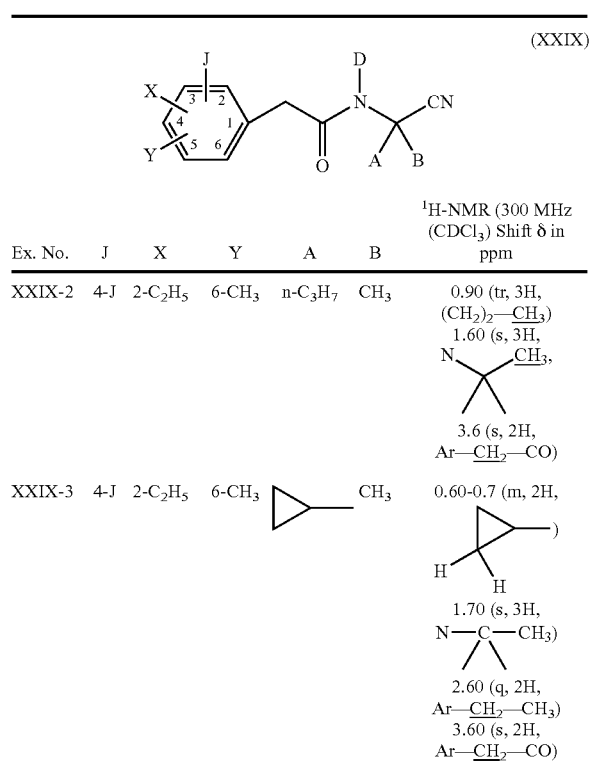

(XXIX)

| Ex. No. | J | X | Y | A | B | $^1$H-NMR (300 MHz (CDCl$_3$) Shift δ in ppm |
|---|---|---|---|---|---|---|
| XXIX-2 | 4-J | 2-C$_2$H$_5$ | 6-CH$_3$ | n-C$_3$H$_7$ | CH$_3$ | 0.90 (tr, 3H, (CH$_2$)$_2$—CH$_3$) 1.60 (s, 3H, N—C(CH$_3$)—), 3.6 (s, 2H, Ar—CH$_2$—CO) |
| XXIX-3 | 4-J | 2-C$_2$H$_5$ | 6-CH$_3$ | (cyclopropyl) | CH$_3$ | 0.60-0.7 (m, 2H, cyclopropyl-H), 1.70 (s, 3H, N—C(CH$_3$)—), 2.60 (q, 2H, Ar—CH$_2$—CH$_3$) 3.60 (s, 2H, Ar—CH$_2$—CO) |

Example I-2-a-1

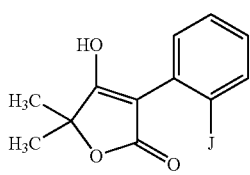

1.31 g (5 mmol) of 2-Iodophenylacetyl chloride and 0.66 g (5 mmol) of ethyl 2-methyl-2-hydroxy-propionate are heated at 140° C. for 10 h, after cooling, 10 ml of dimethylformamide are added, and 6 ml of 1M potassium t-butoxide solution (6 mmol) are added dropwise. The mixture is stirred at room temperature for 10 h and concentrated using a rotary evaporator, and the residue is partitioned between water and ethyl acetate. The aqueous phase is acidifed with 2N HCl and the product is extracted with ethyl acetate, the organic phase is dried and concentrated using a rotary evaporator.

Yield: 1.11 g (68% of theory)

log P 1.80

The following compounds of the formula (I-2-a) are obtained analogously to example (I-2-a-1) and in accordance with the general statements on the preparation

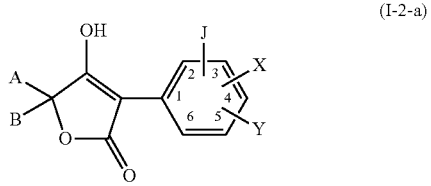

(I-2-a)

| Ex. No. | J | X | Y | A | B | logP |
|---|---|---|---|---|---|---|
| I-2-a-2 | 2-J | H | H | —(CH$_2$)$_2$—CHOCH$_3$—(CH$_2$)$_2$— | | 1.92 |
| I-2-a-3 | 2-J | 5-CH$_3$ | H | —(CH$_2$)$_4$— | | 2.51 |
| I-2-a-4 | 2-J | 5-CH$_3$ | H | —(CH$_2$)$_2$—CHOCH$_3$—(CH$_2$)$_2$— | | 2.19 |
| I-2-a-5 | 4-J | 2-C$_2$H$_5$ | 6-CH$_3$ | —(CH$_2$)$_2$—O—(CH$_2$)$_2$— | | 2.63 |
| I-2-a-6 | 4-J | 2-C$_2$H$_5$ | 6-CH$_3$ | —(CH$_2$)$_2$—CHOCH$_3$—(CH$_2$)$_2$— | | 2.92 |
| I-2-a-7 | 4-J | 2-C$_2$H$_5$ | 6-CH$_3$ | CH$_3$ | CH$_3$ | 2.81 |
| I-2-a-8 | 4-J | 2-C$_2$H$_5$ | 6-CH$_3$ | —(CH$_2$)$_4$— | | 3.00 |
| I-2-a-9 | 4-J | 2-CH$_3$ | 6-CH$_3$ | —(CH$_2$)$_2$—CHOCH$_3$—(CH$_2$)$_2$— | | 2.94 |

Example I-2-b-1

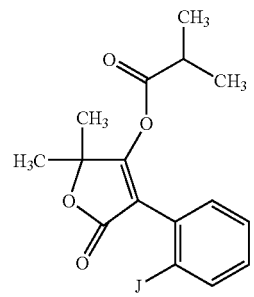

0.25 g (0.757 mmol) of the compound of example I-2-a-1 and 0.092 g (0.909 mmol) of triethylamine are initially charged in 10 ml of dichloromethane, 0.097 g (0.909 mmol) of isobutyryl chloride is added dropwise and the mixture is stirred at room temperature overnight, washed with 10% strength citric acid and 10% strength aqueous sodium hydroxide solution, dried and concentrated using a rotary evaporator. The crude product is purified by column chromatography on silica gel (gradient dichloromethane>dichloromethane/ethyl acetate 95:5).

Yield: 0.23 g (74% of theory), log P 3.53

The following compounds of the formula (I-2-b) are obtained analogously to example (I-2-b-1) and in accordance with the general statements on the preparation 0.25 g (0.757 mmol) of the compound of example I-2-a-1 and 0.092 g (0.909 mmol) of triethylamine are initially charged in 10 ml of dichloromethane, 0.111 g (0.909 mmol)

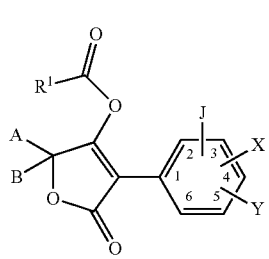

(1-2-b)

| Ex. No. | J | X | Y | A | B | $R^1$ | logP |
|---|---|---|---|---|---|---|---|
| I-2-b-2 | 2-J | H | H | —(CH$_2$)$_2$—CHOCH$_3$—(CH$_2$)$_2$— | | t-C$_4$H$_9$ | 3.95 |
| I-2-b-3 | 2-J | H | H | —(CH$_2$)$_2$—CHOCH$_3$—(CH$_2$)$_2$— | | i-C$_3$H$_7$ | 3.6 |
| I-2-b-4 | 2-J | H | H | CH$_3$ | CH$_3$ | t-C$_4$H$_9$ | 3.87 |
| I-2-b-5 | 2-J | 5-CH$_3$ | H | —(CH$_2$)$_4$— | | t-C$_4$H$_9$ | 4.68 |
| I-2-b-6 | 2-J | 5-CH$_3$ | H | —(CH$_2$)$_2$—CHOCH$_3$—(CH$_2$)$_2$— | | t-C$_4$H$_9$ | 4.57 α isomer |
| I-2-b-7 | 2-J | 5-CH$_3$ | H | —(CH$_2$)$_2$—CHOCH$_3$—(CH$_2$)$_2$— | | t-C$_4$H$_9$ | 4.24 β isomer |
| I-2-b-8 | 4-J | 2-C$_2$H$_5$ | 6-CH$_3$ | CH$_3$ | CH$_3$ | i-C$_3$H$_7$ | 4.72 |
| I-2-b-9 | 4-J | 2-C$_2$H$_5$ | 6-CH$_3$ | —(CH$_2$)$_2$—O—(CH$_2$)$_2$— | | i-C$_3$H$_7$ | 4.42 |
| I-2-b-10 | 4-J | 2-C$_2$H$_5$ | 6-CH$_3$ | —(CH$_2$)$_2$—CHOCH$_3$—(CH$_2$)$_2$— | | i-C$_3$H$_7$ | 4.79 |
| I-2-b-11 | 4-J | 2-CH$_3$ | 6-CH$_3$ | —(CH$_2$)$_4$— | | t-C$_4$H$_9$ | 5.26 |
| I-2-b-12 | 4-J | 2-CH$_3$ | 6-CH$_3$ | —(CH$_2$)$_2$—CHOCH$_3$—(CH$_2$)$_2$— | | t-C$_4$H$_9$ | 5.21 α isomer |
| I-2-b-13 | 4-J | 2-CH$_3$ | 6-CH$_3$ | —(CH$_2$)$_2$—CHOCH$_3$—(CH$_2$)$_2$— | | t-C$_4$H$_9$ | 4.9 β isomer |

Example I-2-c-1

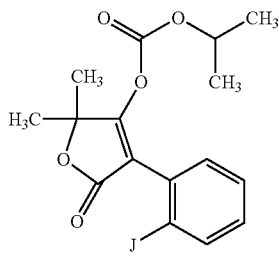

of isopropyl chloroformate is added dropwise, and the mixture is stirred at room temperature overnight, washed with 10% strength citric acid and 10% strength aqueous sodium hydroxide solution, dried and concentrated using a rotary evaporator. The crude product is purified by column chromatography on silica gel (gradient dichloromethane>dichloromethane/ethyl acetate 95:5).

Yield: 0.16 g (46% of theory), log P 3.47

The following compounds of the formula (I-2-c) are obtained analogously to example (I-2-c-1) and in accordance with the general statements on the preparation

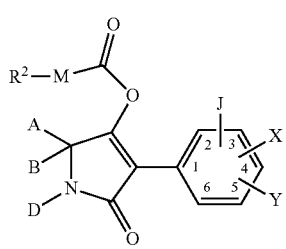

(1-2-c)

| Ex. No. | J | X | Y | A | B | M | $R^2$ | logP |
|---|---|---|---|---|---|---|---|---|
| I-2-c-2 | 2-J | H | H | —(CH$_2$)$_2$—CHOCH$_3$—(CH$_2$)$_2$— | | O | i-C$_3$H$_7$ | 3.54 |
| I-2-c-3 | 4-J | 2-C$_2$H$_5$ | 6-CH$_3$ | CH$_3$ | CH$_3$ | O | i-C$_3$H$_7$ | 4.66 |
| I-2-c-4 | 4-J | 2-C$_2$H$_5$ | 6-CH$_3$ | —(CH$_2$)$_2$—CHOCH$_3$—(CH$_2$)$_2$— | | O | i-C$_3$H$_7$ | 4.77 |
| I-2-c-5 | 4-J | 2-C$_2$H$_5$ | 6-CH$_3$ | —(CH$_2$)$_2$—O—(CH$_2$)$_2$— | | O | i-C$_3$H$_7$ | 4.41 |

Example I-8-a-1

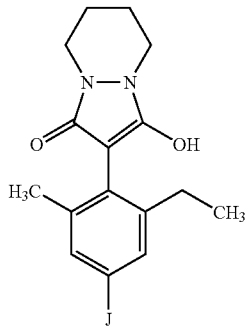

0.566 g of potassium tert-butoxide is initially charged in 5 ml of N,N-dimethylacetamide at 50° C., 1 g of the compound of example (XII-1) in 5 ml of N,N-dimethylacetamide is added and the mixture is stirred at 60° C. for 2 h. The cooled reaction solution is then added dropwise to ice-water/concentrated HCl. The crystals are filtered off with suction.

Yield: 0.54 g (86% of theory), m.p. 229° C.

Example I-8-b-1

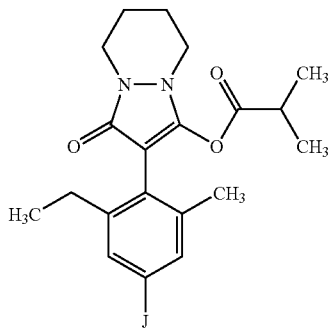

0.25 g (0.001 mol) of the compound of example I-8-a-1 and 0.074 g of 2-methylpropionyl chloride are initially charged in 15 ml of toluene at room temperature, 0.11 ml of triethylamine is added dropwise, the mixture is stirred for 2 h, water is added and the mixture is extracted. The organic phase is dried and concentrated using a rotary evaporator, and the residue is crystallized using n-heptane and a little ethyl acetate.

Yield: 0.1 g (32% of theory)

$^1$H-NMR (300 MHz, CDCl$_3$): δ=7.40 ppm (s, 2H, Ar—H), 3.80 ppm (m, 2H, N—C$\underline{H}_2$), 3.40 ppm (m, 2H, N—C$\underline{H}_2$), 2.40 ppm (sept, 1H, C$\underline{H}$C(CH$_3$)$_2$), 2.00-1.80 ppm (m, 4H, 2×C$\underline{H}_2$ cycle).

Example No. (I-8-b-2) is obtained analogously to example (I-8-b-1)

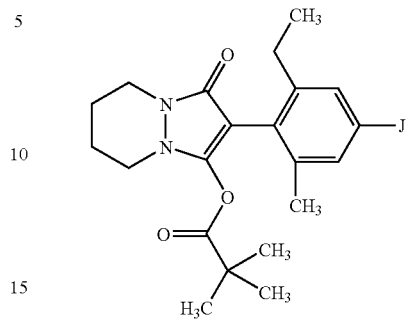

$^1$H-NMR (300 MHz, CDCl$_3$): δ=7.40 (s, 2H, Ar—H), 3.90 (m, 2H, N—C$\underline{H}_2$), 3.40 (m, 2H, N—C$\underline{H}_2$), 2.60-2.40 (m, 2H, Ar—C$\underline{H}_2$) ppm.

Example I-8-c-1

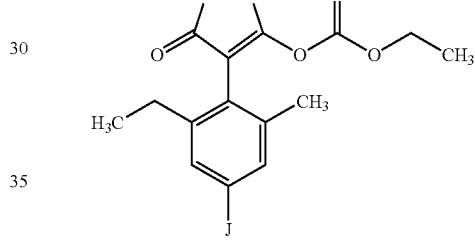

0.07 ml of ethyl chloroformate is added to 0.25 g (0.001 mol) of the compound of example I-8-a-1 and 0.11 ml of triethylamine and 15 ml of toluene, and the mixture is stirred at room temperature for 1 hour. The reaction solution is extracted with water and the organic phase is dried. Purification is carried out by HPLC.

Yield: 0.09 g (29% of theory)

$^1$H-NMR (300 MHz, CDCl$_3$): δ=7.40 (s, 2H, Ar—H), 4.15 (q, 2H, O—C$\underline{H}_2$), 3.80 (tr, 2H, N—C$\underline{H}_2$), 3.45 (tr, 2H, Ar—C$\underline{H}_2$), 2.50 (m, 2H, Ar—C$\underline{H}_2$), 2.00-1.80 (m, 4H, 2×C$\underline{H}_2$ cycle) ppm.

Example XII-1

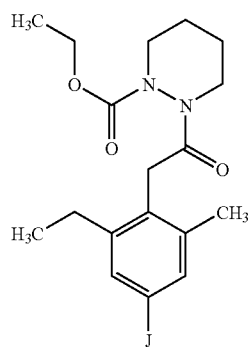

1.83 ml of triethylamine are added to 2 g of 4-iodo-2-ethyl-6-methylphenylacetic acid in 40 ml of tetrahydrofuran, and the mixture is stirred for 15 minutes. 1.095 g of ethyl hexahydropyridazine carbamate are then added, the mixture is stirred for 10 minutes and 1.92 ml of triethylamine are added. Immediately afterward, 0.55 ml of phosphoryl chloride is slowly added dropwise. The mixture is stirred under reflux for 30 minutes.

After cooling, the mixture is concentrated using a rotary evaporator, the residue is worked up with ethyl acetate/water and the organic phase is separated off, dried with sodium sulfate, filtered off and concentrated using a rotary evaporator.

Yield: 2.5 g (85% of theory)

$^1$H-NMR (400 MHz, CDCl$_3$): δ=1.15, 1.30 (2 t, 6H, OCH$_2$CH$_3$, Ar CH$_2$CH$_3$), 2.20 (s, 3H, Ar—CH$_3$), 2.50 (q, 2H, Ar—CH$_2$CH$_3$), 3.60, 3.70 (2d, 2H, NCH$_2$), 7.40 (s, 2H, Ar—H) ppm.

Process Q

Example XXXI-1

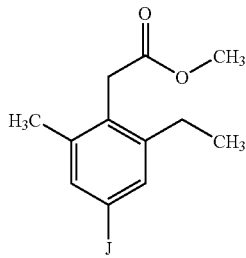

Under argon, a solution of 10 g of methyl(4-bromo-2-methyl-6-ethylphenyl)acetate, 11.056 g of sodium iodide, 7.023 g of copper(I) iodide and 3.172 g of N,N'-dimethylethylenediamine in 250 ml of dioxane is heated at 110° C. for 18 h. After the reaction has ended, the reaction mixture is filtered and the mother liquor is diluted with 300 ml of water and extracted twice with 200 ml of dichloromethane. The organic phase is washed with 25% strength ammonia solution, dried over sodium sulfate and freed from the solvent. Yield of methyl(2-ethyl-4-iodo-6-methylphenyl)acetate: 7.8 g, 65%.

$^1$H-NMR (300 MHz, d$_6$-DMSO): δ=7.42 (d, 1H), 7.39 (d, 1H), 3.68 (s, 2H), 3.61 (s, 3H), 2.55 (q, 2H), 219 (s, 3H), 1.10 (t, 3H) ppm.

Example XXVII-1

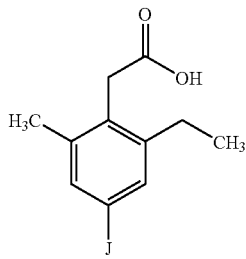

A solution of 0.696 g of LiOH in 50 ml of water is added to a solution of 7.7 g of methyl(2-ethyl-4-iodo-6-methylphenyl)acetate in 50 ml of THF, and the mixture is stirred at room temperature for 18 h. The mixture is then evaporated to dryness using a rotary evaporator, and in each case 50 ml of ethyl acetate and water are added to the residue. The phases are separated and the ethyl acetate phase is washed with water. The combined aqueous phases are adjusted to pH=1 using HCl, and the precipitated solid is filtered off with suction, washed with water and dried under reduced pressure. Yield of (2-ethyl-4-iodo-6-methylphenyl)acetic acid: 6 g, 78%.

$^1$H-NMR (300 MHz, d$_6$-DMSO): δ=12.5 (s(br), 1H), 7.40 (d, 1H), 7.38 (d, 1H), 3.57 (s, 2H), 2.56 (q, 2H), 1.09 (t, 3H) ppm.

Example XXXI-2

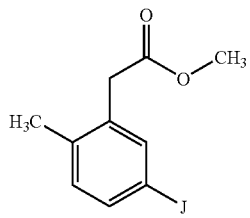

Under argon, a solution of 20 g of methyl(5-bromo-2-methylphenyl)acetate, 24.663 g of sodium iodide, 15.668 g of copper(I) iodide and 7.075 g of N,N'-dimethylethylenediamine in 500 ml of dioxane is heated at 110° C. for 3 days. Another 8 g of sodium, 5.5 g of copper(I) iodide and 3.3 g of N,N'-dimethylethylenediamine are then added. After a further 3 days of heating at 110° C., the reaction mixture is filtered and the mother liquor is diluted with 300 ml of water and extracted twice with 200 ml of dichloromethane. The organic phase is washed with 25% strength ammonia solution, dried over Na$_2$SO$_4$ and freed from the solvent. Yield of methyl(5-iodo-2-methylphenyl)acetate: 11.6 g, 30%.

$^1$H-NMR (300 MHz, d$_6$-DMSO): δ=7.56 (d, 1H), 7.51 (d, 1H), 6.99 (d, 1H), 3.62 (s, 2H), 3.57 (s, 3H), 2.16 (s, 3H) ppm.

Example XXVII-2

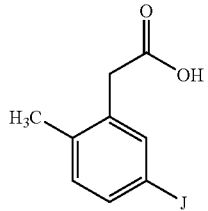

A solution of 1.048 g of LiOH in 75 ml of water is added to a solution of 10.7 g of methyl(5-iodo-2-methylphenyl)acetate in 75 ml of THF, and the mixture is stirred at room temperature for 18 h. The mixture is then concentrated to dryness using a rotary evaporator, and in each case 75 ml of ethyl acetate and water are added to the residue. The phases are separated and the organic phase is washed with water. The combined aqueous phases are adjusted to pH=1 using HCl and the precipitated solid is triturated successively with dichloromethane and ethyl acetate, filtered off with suction and dried under reduced pressure. For further purification, it is triturated with diethyl ether and filtered off. Yield of (5-iodo-2-methylphenyl)acetic acid: 5.5 g, 44%.

¹H-NMR (300 MHz, d₆-DMSO): δ=12.2 (s, (br) 1H), 7.55 (d, 1H), 7.49 (d, 1H), 6.98 (d, 1H), 3.56 (s, 2H), 2.17 (s, 3H) ppm.

The following compounds of the formula (XXXI) are obtained analogously to examples (XXXI-1) and (XXXI-2)

| Structure | Ex. No. | ¹H-NMR (400 MHz, d₆ DMSO) |
|---|---|---|
| (2-iodo-5-methylphenyl acetate methyl ester) | XXXI-3 | δ = 7.70 (d, 1H), 7.19 (d, 1H), 6.85 (dd, 1H), 3.76 (s, 2H), 3.63 (s, 3H), 2.25 (s, 2H) ppm. |
| (2,6-dimethyl-4-iodophenyl acetate methyl ester) | XXXI-4 | δ = 7.41 (s, 2H), 3.66 (s, 2H), 3.60 (s, 3H), 2.20 (s, 6H) ppm. |
| (2-iodo-4-chloro-6-methylphenyl acetate methyl ester) | XXXI-5 | δ = 7.76 (d, 1H), 7.35 (d, 1H), 3.90 (s, 2H), 3.64 (s, 3H), 2.30 (s, 3H), ppm. |

-continued

| Structure | Ex. No. | ¹H-NMR (400 MHz, d₆ DMSO) |
|---|---|---|
| (2-iodo-4-chloro-6-ethylphenyl acetate methyl ester) | XXXI-6 | δ = 7.79 (d, 1H), 7.34 (d, 1H), 3.91 (s, 2H), 3.64 (s, 3H), 2.64 (q, 2H), 1.11 (t, 3H) ppm. |
| (2-chloro-4-iodo-6-methylphenyl acetate methyl ester) | XXXI-7 | Only a GC was measured for monitoring the reaction, directly reacted further. |
| (2-chloro-4-iodo-6-ethylphenyl acetate methyl ester) | XXXI-8 | Only a GC was measured for monitoring the reaction, directly reacted further. |

The following compounds of the formula (XXVII) are obtained analogously to examples (XXVII-1) and (XXVII-2)

| Structure | Ex. No. | ¹H-NMR (400 MHz, d₆ DMSO) |
|---|---|---|
| (2-iodo-5-methylphenyl acetic acid) | XXVII-3 | δ = 12.31 (s (br), 1H), 7.69 (d, 1H), 7.18 (d, 1H), 6.83 (dd, 1H), 3.66 (s, 2H), 2.24 (s, 2H) ppm. |
| (2,6-dimethyl-4-iodophenyl acetic acid) | XXVII-4 | δ = 12.3 (s (br), 1H), 7.40 (s, 2H), 3.55 (s, 2H), 2.21 (s, 6H) ppm. |

| Structure | Ex. No. | $^1$H-NMR (400 MHz, d$_6$ DMSO) |
|---|---|---|
| (structure: 2-(2-iodo-4-chloro-6-methylphenyl)acetic acid) | XXVII-5 | δ = 12.46 (s (br), 1H), 7.75 (d, 1H), 7.33 (d, 1H), 3.80 (s, 2H), 2.31 (s, 3H), ppm. |
| (structure: 2-(2-iodo-4-chloro-6-ethylphenyl)acetic acid) | XXXI-6 | δ = 12.47 (s (br), 1H), 7.76 (d, 1H), 7.31 (d, 1H), 3.81 (s, 2H), 2.64 (q, 2H), 1.11 (t, 3H) ppm. |
| (structure: 2-(2-chloro-4-iodo-6-methylphenyl)acetic acid) | XXVII-7 | δ = 12.50 (s (br), 1H), 7.65 (d, 1H), 7.58 (d, 1H), 3.71 (s, 2H), 2.25 (s, 3H), ppm. |
| (structure: 2-(2-chloro-4-iodo-6-ethylphenyl)acetic acid) | XXVII-8 | δ = 12.41 (s (br), 1H), 7.66 (d, 1H), 7.55 (d, 1H), 3.72 (s, 2H), 2.63 (q, 2H), 1.11 (t, 3H) ppm. |

The logP values given in the Tables and Preparation Examples above are determined in accordance with EEC Directive 79/831 Annex V.A8 by HPLC (High Performance Liquid Chromatography) on a reversed-phase column (C18). Temperature: 43° C.

The determination is carried out in the acidic range at pH 2.3 using the mobile phases 0.1% aqueous phosphoric acid and acetonitrile; linear gradient from 10% acetonitrile to 95% acetonitrile.

The LC-MS determination in the acidic range is carried out at pH 2.7 using the mobile phases 0.1% aqueous formic acid and acetonitrile (contains 0.1% formic acid); linear gradient from 10% acetonitrile to 95% acetonitrile.

The LC-MS determination in the neutral range is carried out at pH 7.8 using the mobile phases 0.001 molar aqueous ammonium bicarbonate solution and acetonitrile; linear gradient from 10% acetonitrile to 95% acetonitrile.

Calibration is carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Use Examples

Example A

Phaedon Test (Spray Treatment)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show, at an application rate of 500 g/ha, an efficacy of ≥80%.

I-1-a-1, I-1-a-2, I-1-a-3, I-1-a-4, I-1-a-5, I-1-a-11, I-1-a-12, I-1-a-13, I-1-a-14, I-1-a-18, I-1-a-19, I-1-a-21, I-1-a-23, I-1-b-1, I-1-b-7, I-1-b-11, I-1-b-18, I-1-c-4, I-1-c-7, I-1-c-8, I-1-c-9, I-1-c-10, I-1-c-11, I-1-c-17, I-1-c-20, I-2-a-6, I-2-b-10, I-2-b-11.

Example B

Myzus Test (Spray Treatment)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show, at an application rate of 500 g/ha, an efficacy of ≥80%.

I-1-a-1, I-1-a-2, I-1-a-3, I-1-a-4, I-1-a-5, I-1-a-7, I-1-a-8, I-1-a-9, I-1-a-11, I-1-a-18, I-1-a-19, I-1-a-20, I-1-a-22, I-1-a-24, I-1-b-1, I-1-b-2, I-1-b-9, I-1-b-11, I-1-c-1, I-1-c-2, I-1-c-3, I-1-c-4, I-1-c-6, I-1-c-7, I-1-c-8, I-1-c-9, I-1-c-12, I-1-c-20, I-2-a-2, I-2-a-4, I-2-a-5, I-2-a-6, I-2-a-9, I-2-b-2, I-2-b-3, I-2-b-4, I-2-b-6, I-2-b-7, I-2-b-9, I-2-b-10, I-2-b-11, I-2-b-12, I-2-b-13, I-2-c-2, I-2-c-4, I-2-c-5, I-8-b-2.

Example C

Nilaparvata Lugens Test (Hydroponic Treatment)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

The active compound preparation is pipetted into water. The stated concentration refers to the amount of active compound per volume unit of water (mg/l=ppm). After the desired period of time, the water is infected with the brown plant hopper (*Nilaparvata lugens*).

After the desired period of time, the effect in % is determined. 100% means that all plant hoppers have been killed; 0% means that none of the plant hoppers have been killed.

In this test, the compound of Preparation Example I-2-a-2 showed, at a concentration of 20 ppm, an efficacy of ≥80%.

Example D

Tetranychus Test; OP-Resistant/Spray Treatment (TETRUR)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are heavily infested by all stages of the greenhouse red spider mite (*Tetranychus urticae*) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 100 g/ha, an efficacy of ≥80%.

I-1-a-2, I-1-a-4, I-1-a-5, I-1-a-7, I-1-a-11, I-1-a-12, I-1-a-18, I-1-a-19, I-1-a-21, I-1-a-21, I-1-a-22, I-1-b-2, I-1-b-18, I-1-c-1, I-1-c-4, I-1-c-5, I-1-c-20, I-2-a-6, I-2-b-2, I-2-b-5, I-2-b-6, I-2 b-8, I-2-b-10, I-2-b-11, I-2-c-2, I-2-c-3, I-2-c-4, I-2-c-5, I-8-b-1, I-8-b-2.

In this test, for example, the following compound of the Preparation Example showed, at an application rate of 500 g/ha, an efficacy of ≥80%:

I-1-a-14.

Example E

Herbicidal Pre-Emergence Action

Seeds of monocotyledonous and dicotyledonous weed and crop plants are placed in sandy loam in wood fiber pots and covered with soil. The test compounds, formulated in the form of wettable powders (WP) or as emulsion concentrates (EC), are then, as an aqueous suspension with a water application rate of 800 l/ha (converted), with 0.2% of wetting agent added, applied to the surface of the covering soil.

After the treatment, the pots are placed in a greenhouse and kept under growth conditions for the test plants. The visual assessment of the emergence damage on the test plants is carried out after a trial period of 3 weeks by comparison with untreated controls (herbicidal effect in percent (%): 100% effect=the plants have died, 0% effect=like control plants).

Here, the following compounds, for example, controlled *Avena sativa, Lolium multiflorum* and *Setaria viridis* at an application rate of 320 g/ha with ≥70% efficacy:

I-1-a-8, I-1-a-14, I-1-a-21, I-1-a-7.

Example F

Herbicidal Post-Emergence Action

Seeds of monocotyledonous and dicotyledonous weed and crop plants are placed in sandy loam in wood fiber pots, covered with soil and cultivated in a greenhouse under good growth conditions. Two to three weeks after sowing, the test plants are treated at the one-leaf stage. The test compounds, formulated as wettable powders (WP) or as emulsion concentrates (EC), are then, as an aqueous suspension with a water application rate of 800 l/ha (converted), with 0.2% of wetting agent added, sprayed onto the green parts of the plants. After the test plants have been kept in the greenhouse under optimum growth conditions for about 3 weeks, the effect of the preparations is rated visually in comparison to treated controls (herbicidal effect in percent (%): 100% effect=the plants have died, 0% effect=like control plants).

Here, the following compounds, for example, controlled *Avena sativa, Echinochloa crus*-galli, *Lolium multiflorum* and *Setaria viridis* at an application rate of 320 g/ha with ≥70% efficacy:

I-1-a-8, I-1-a-11, I-1-a-12, I-1-a-13, I-1-a-14, I-1-a-21, I-1-c-1, I-1-c-6, I-1-c-11, I-1-c-12, I-2-b-10, I-2-c-3, I-8-b-2.

Example G

Herbicidal Post-Emergence Action

Seeds of monocotyledonous and dicotyledonous weed and crop plants are placed into sandy loam in wood fiber pots or in plastic pots, covered with soil and cultivated in a greenhouse, during the vegetation period also outdoors outside of the greenhouse, under good growth conditions. Two to three weeks after sowing, the test plants are treated at the one- to three-leaf stage. The test compounds, formulated as wettable powders (WP) or liquid (EC), are, in various dosages at a water application rate of 300 l/ha (converted), with wetting agent (0.2 to 0.3%) added, sprayed onto the plants and the surface of the soil. Three to four weeks after the treatment of the test plants, the effect of the preparations is rated visually in comparison to treated controls (herbicidal effect in %) (%): 100% effect=the plants have died, 0% effect=like control plants).

Use of Safeners

If it is additionally to be tested as to whether safeners can improve the plant compatibility of test substances in the case of crop plants, the following options are used for applying the safener:
- seeds of the crop plants are, before sowing, dressed with the safener substance (the amount of safener stated in percent, based on the weight of the seed)
- before the application of the test substances, the crop plants are sprayed with the safener at a certain application rate per hectare (usually 1 day before the application of the test substances)
- the safener is applied together with the test substance as a tank mix (the amount of safener is stated in g/ha or as a ratio, based on the herbicide).

By comparing the effect of test substances on crop plants without or with safener treatment, it is possible to assess the effect of the safener substance.

Container Trials with Cereal in a Greenhouse
Mefenpyr 1 day prior to herbicide application

|  | 10 days after application | |
|---|---|---|
|  | Application rate g of a.i./ha | Summer wheat observed (%) |
| Example I-1-a-3 | 100 | 40 |
|  | 50 | 30 |
|  | 25 | 20 |
|  | 12.5 | 10 |
| Example I-1-a-3 + mefenpyr | 100 + 100 | 20 |
|  | 50 + 100 | 10 |
|  | 25 + 100 | 5 |
|  | 12.5 + 100 | 0 |

|  | 10 days after application | |
|---|---|---|
|  | Application rate g of a.i./ha | Summer wheat observed (%) |
| Example I-1-c-1 | 12.5 | 50 |
| Example I-1-c-1 + mefenpyr | 12.5 + 100 | 15 |

|  | 10 days after application | | |
|---|---|---|---|
|  | Application rate g of a.i./ha | Summer wheat observed (%) | Summer wheat observed (%) |
| Example I-2-b-10 | 200 | 70 |  |
|  | 100 | 50 |  |
|  | 50 | 30 | 65 |
|  | 25 | 15 | 60 |
| Example I-2-b-10 + mefenpyr | 200 + 100 | 20 |  |
|  | 100 + 100 | 10 |  |
|  | 50 + 100 | 5 | 40 |
|  | 25 + 100 | 5 | 15 |

|  | 28 days after application | |
|---|---|---|
|  | Application rate g of a.i./ha | Summer wheat observed (%) |
| Example I-2-b-10 | 200 | 75 |
|  | 100 | 50 |
|  | 50 | 40 |
|  | 25 | 25 |
| Example I-2-b-10 + mefenpyr | 200 + 100 | 20 |
|  | 100 + 100 | 5 |
|  | 50 + 100 | 0 |
|  | 25 + 100 | 0 |

Example H

Critical Concentration Test/Soil Insects—Treatment of Transgenic Plants

Test insect: *Diabrotica balteata*—larvae in the soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per unit volume of soil, which is stated in ppm (mg/l), matters. The soil is filled into 0.25 l pots, and these are allowed to stand at 20° C.

Immediately after the preparation, 5 pregerminated corn grains of the cultivar YIELD GUARD (trademark of Monsanto Comp., USA) are placed into each pot. After 2 days, the appropriate test insects are placed into the treated soil. After a further 7 days, the efficacy of the active compound is determined by counting the corn plants that have emerged (1 plant=20% activity).

Example I

*Heliothis virescens* Test—Treatment of Transgenic Plants
Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soybean shoots (Glycine max) of the cultivar Roundup Ready (trademark of Monsanto Comp. USA) are treated by being dipped into the preparation of active compound of the desired concentration and are populated with the tobacco budworm Heliothis virescens while the leaves are still moist.

After the desired period of time, the kill of the insects is determined.

The invention claimed is:

1. A compound of the formulae (I-1-a), (I-1-b) or (I-1-c):

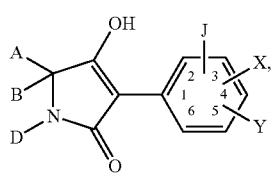
(I-1-a)

Wherein
A, B, D, J, X and Y have the meanings given in the table:

| Compound | J | X | Y | D | A | B |
|---|---|---|---|---|---|---|
| I-1-a-1 | 2-I | H | H | H | —(CH$_2$)$_2$—CHOCH$_3$—(CH$_2$)$_2$— | |
| I-1-a-2 | 4-I | 2-C$_2$H$_5$ | 6-CH$_3$ | H | —(CH$_2$)$_2$—CHOCH$_3$—(CH$_2$)$_2$— | |
| I-1-a-3 | 2-I | 4-CH$_3$ | 6-CH$_3$ | H | —(CH$_2$)$_2$—CHCH$_3$—(CH$_2$)$_2$— | |
| I-1-a-5 | 2-I | 5-CH$_3$ | H | H | —(CH$_2$)$_2$—CHOCH$_3$—(CH$_2$)$_2$— | |
| I-1-a-6 | 2-I | 5-CH$_3$ | H | H | —(CH$_2$)$_2$—O—(CH$_2$)$_2$— | |
| I-1-a-7 | 2-I | 4-Cl | 6-C$_2$H$_5$ | H | —(CH$_2$)$_2$—O—(CH$_2$)$_2$— | |
| I-1-a-8 | 2-I | 4-Cl | 6-C$_2$H$_5$ | H | —(CH$_2$)$_2$—CHOCH$_3$—(CH$_2$)$_2$— | |
| I-1-a-10 | 3-I | 6-CH$_3$ | H | H | —(CH$_2$)$_2$—CHOCH$_3$—(CH$_2$)$_2$— | |
| I-1-a-11 | 4-I | 2-C$_2$H$_5$ | 6-CH$_3$ | H | —(CH$_2$)$_2$—O—(CH$_2$)$_2$— | |
| I-1-a-12 | 4-I | 2-C$_2$H$_5$ | 6-CH$_3$ | H | CH$_3$ | CH$_3$ |
| I-1-a-13 | 4-I | 2-C$_2$H$_5$ | 6-CH$_3$ | H | ▷ | CH$_3$ |
| I-1-a-14 | 4-I | 2-C$_2$H$_5$ | 6-CH$_3$ | H | n-C$_3$H$_7$ | CH$_3$ |
| I-1-a-15 | 4-I | 2-C$_2$H$_5$ | 6-CH$_3$ | —CH——CH—CH$_2$—\\(CH$_2$)$_4$ | | H |
| I-1-a-16 | 4-I | 2-C$_2$H$_5$ | 6-CH$_3$ | H | —(CH$_2$)$_5$— | |
| I-1-a-17 | 4-I | 2-C$_2$H$_5$ | 6-CH$_3$ | H | —(CH$_2$)$_2$—CHCH$_3$—(CH$_2$)$_2$— | |
| I-1-a-18 | 4-I | 2-CH$_3$ | 6-CH$_3$ | H | —(CH$_2$)$_2$—CHOCH$_3$—(CH$_2$)$_2$— | |
| I-1-a-19 | 4-I | 2-CH$_3$ | 6-CH$_3$ | H | —(CH$_2$)$_2$—O—(CH$_2$)$_2$— | |
| I-1-a-20 | 4-I | 2-C$_2$H$_5$ | 6-Cl | H | —(CH$_2$)$_2$—O—(CH$_2$)$_2$— | |
| I-1-a-21 | 4-I | 2-CH$_3$ | 6-CH$_3$ | H | —CH$_2$—CHOC$_4$H$_9$—(CH$_2$)$_3$— | |
| I-1-a-23 | 4-I | 2-C$_2$H$_5$ | 6-CH$_3$ | H | —CH$_2$—CHOC$_4$H$_9$—(CH$_2$)$_3$— | |
| I-1-a-24 | 4-I | 2-C$_2$H$_5$ | 6-Cl | H | —(CH$_2$)$_2$—CHOCH$_3$—(CH$_2$)$_2$— | |
| I-1-a-26 | 4-I | 2-C$_2$H$_5$ | 6-CH$_3$ | H | i-C$_3$H$_7$ | CH$_3$ |
| I-1-a-27 | 4-I | 2-C$_2$H$_5$ | 6-CH$_3$ | H | i-C$_4$H$_9$ | CH$_3$ |

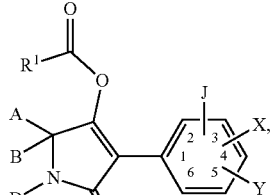
(I-1-b)

wherein
A, B, D, R$^1$, J, X and Y have the meanings given in the table:

| Compound | J | X | Y | D |
|---|---|---|---|---|
| I-1-b-1 | 2-I | 5-CH$_3$ | H | H |
| I-1-b-2 | 2-I | 5-CH$_3$ | H | H |
| I-1-b-3 | 2-I | 4-Cl | 6-C$_2$H$_5$ | H |
| I-1-b-4 | 2-I | 4-Cl | 6-C$_2$H$_5$ | H |
| I-1-b-5 | 4-I | 2-C$_2$H$_5$ | 6-CH$_3$ | H |
| I-1-b-6 | 4-I | 2-C$_2$H$_5$ | 6-CH$_3$ | H |
| I-1-b-7 | 4-I | 2-CH$_3$ | 6-CH$_3$ | H |
| I-1-b-8 | 4-I | 2-CH$_3$ | 6-CH$_3$ | H |
| I-1-b-9 | 4-I | 2-CH$_3$ | 6-CH$_3$ | H |
| I-1-b-10 | 4-I | 2-CH$_3$ | 6-CH$_3$ | H |
| I-1-b-11 | 4-I | 2-C$_2$H$_5$ | 6-CH$_3$ | H |
| I-1-b-12 | 4-I | 2-C$_2$H$_5$ | 6-Cl | H |
| I-1-b-13 | 4-I | 2-C$_2$H$_5$ | 6-CH$_3$ | H |
| I-1-b-14 | 4-I | 2-C$_2$H$_5$ | 6-CH$_3$ | H |
| I-1-b-15 | 4-I | 2-C$_2$H$_5$ | 6-CH$_3$ | H |
| I-1-b-16 | 4-I | 2-C$_2$H$_5$ | 6-CH$_3$ | H |
| I-1-b-17 | 4-I | 2-C$_2$H$_5$ | 6-CH$_3$ | H |
| I-1-b-18 | 4-I | 2-C$_2$H$_5$ | 6-CH$_3$ | H |
| I-1-b-19 | 4-I | 2-C$_2$H$_5$ | 6-CH$_3$ | H |
| I-1-b-20 | 4-I | 2-C$_2$H$_5$ | 6-CH$_3$ | H |
| I-1-b-21 | 4-I | 2-C$_2$H$_5$ | 6-CH$_3$ | H |
| I-1-b-22 | 4-I | 2-C$_2$H$_5$ | 6-CH$_3$ | H |

| Compound | A | B | R$^1$ |
|---|---|---|---|
| I-1-b-1 | —(CH$_2$)$_2$—CHOCH$_3$—(CH$_2$)$_2$— | | ▷ |
| I-1-b-2 | —(CH$_2$)$_2$—CHOCH$_3$—(CH$_2$)$_2$— | | i-C$_3$H$_7$ |
| I-1-b-3 | —(CH$_2$)$_2$—CHOCH$_3$—(CH$_2$)$_2$— | | H$_3$C—O—CH$_2$— |
| I-1-b-4 | —(CH$_2$)$_2$—O—(CH$_2$)$_2$— | | H$_3$C—O—CH$_2$— |
| I-1-b-5 | —(CH$_2$)$_2$—O—(CH$_2$)$_2$— | | i-C$_3$H$_7$ |
| I-1-b-6 | C$_3$H$_7$ | CH$_3$ | i-C$_3$H$_7$ |
| I-1-b-7 | —CH$_2$—CH—OC$_4$H$_9$—(CH$_2$)$_3$— | | H$_3$C—O—CH$_2$— |
| I-1-b-8 | —CH$_2$—CHOC$_4$H$_9$—(CH$_2$)$_3$— | | ▷ |
| I-1-b-9 | —CH$_2$—CHOC$_4$H$_9$—(CH$_2$)$_3$— | | Cl—CH$_2$— |
| I-1-b-10 | —CH$_2$—CHOC$_4$H$_9$—(CH$_2$)$_3$— | | (3-Cl-4-CH$_3$-phenyl) |
| I-1-b-11 | —(CH$_2$)$_2$—O—(CH$_2$)$_2$— | | H$_3$C—O—CH$_2$— |
| I-1-b-12 | —(CH$_2$)$_2$—O—(CH$_2$)$_2$— | | H$_3$C—O—CH$_2$— |
| I-1-b-13 | —CH$_2$—CHOC$_4$H$_9$—(CH$_2$)$_3$— | | i-C$_3$H$_7$ |
| I-1-b-14 | i-C$_3$H$_7$ | CH$_3$ | i-C$_3$H$_7$ |
| I-1-b-15 | —CH$_2$—CHOC$_4$H$_9$—(CH$_2$)$_3$— | | H$_3$C—O—CH$_2$— |
| I-1-b-16 | —(CH$_2$)$_5$— | | H$_3$C—O—CH$_2$— |
| I-1-b-17 | —(CH$_2$)$_5$— | | i-C$_3$H$_7$ |
| I-1-b-18 | CH$_3$ | CH$_3$ | i-C$_3$H$_7$ |
| I-1-b-19 | —(CH$_2$)$_5$— | | t-C$_4$H$_9$ |
| I-1-b-20 | i-C$_3$H$_7$ | CH$_3$ | H$_3$C—O—CH$_2$— |
| I-1-b-21 | CH$_3$ | CH$_3$ | H$_3$C—O—CH$_2$— |
| I-1-b-22 | i-C$_3$H$_7$ | CH$_3$ | i-C$_3$H$_7$ |

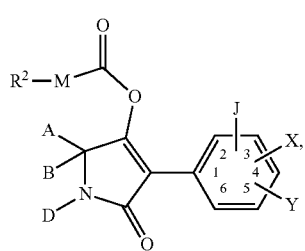

(I-1-c)

wherein

A, B, D, M R², J, X and Y have the meanings given in the table:

| Compound | J | X | Y | D | A | B |
|---|---|---|---|---|---|---|
| I-1-c-1 | 4-I | 2-CH₃ | 6-C₂H₅ | H | —(CH₂)₂—CHOCH₃—(CH₂)₂— | |
| I-1-c-2 | 2-I | 5-CH₃ | H | H | —(CH₂)₂—CHOCH₃—(CH₂)₂— | |
| I-1-c-4 | 2-I | 5-CH₃ | H | H | —(CH₂)₂—CHOCH₃—(CH₂)₂— | |
| I-1-c-5 | 2-I | 4-Cl | 6-C₂H₅ | H | —(CH₂)₂—O—(CH₂)₂— | |
| I-1-c-6 | 2-I | 4-Cl | 6-C₂H₅ | H | —(CH₂)₂—CHOCH₃—(CH₂)₂— | |
| I-1-c-7 | 3-I | 6-CH₃ | H | H | —(CH₂)₂—CHOCH₃—(CH₂)₂— | |
| I-1-c-8 | 4-I | 2-CH₃ | 6-CH₃ | H | —(CH₂)₂—CHOCH₃—(CH₂)₂— | |
| I-1-c-10 | 4-I | 2-C₂H₅ | 6-CH₃ | H | n-C₃H₇ | CH₃ |
| I-1-c-11 | 4-I | 2-C₂H₅ | 6-CH₃ | H | △ | CH₃ |
| I-1-c-12 | 4-I | 2-C₂H₅ | 6-CH₃ | H | —(CH₂)₂—O—(CH₂)₂— | |
| I-1-c-13 | 4-I | 2-C₂H₅ | 6-Cl | H | —(CH₂)₂—O—(CH₂)₂— | |
| I-1-c-14 | 4-I | 2-CH₃ | 6-CH₃ | H | —CH₂—CHOC₄H₉—(CH₂)₃— | |
| I-1-c-15 | 4-I | 2-CH₃ | 6-CH₃ | H | —CH₂—CHOC₄H₉—(CH₂)₃— | |
| I-1-c-16 | 4-I | 2-CH₃ | 6-CH₃ | H | —CH₂—CHOC₄H₉—(CH₂)₃— | |
| I-1-c-17 | 4-I | 2-C₂H₅ | 6-CH₃ | H | —(CH₂)₅— | |
| I-1-c-18 | 4-I | 2-CH₃ | 6-CH₃ | H | CH₃ | CH₃ |
| I-1-c-19 | 4-I | 2-C₂H₅ | 6-CH₃ | H | i-C₄H₉ | CH₃ |
| I-1-c-20 | 4-I | 2-CH₃ | 6-CH₃ | H | —(CH₂)₂—O—(CH₂)₂— | |

| Compound | M | R² |
|---|---|---|
| I-1-c-1 | O | C₂H₅ |
| I-1-c-2 | O | C₆H₅—CH₂— |
| I-1-c-4 | O | C₂H₅ |
| I-1-c-5 | O | C₂H₅ |
| I-1-c-6 | O | C₂H₅ |
| I-1-c-7 | O | C₂H₅ |
| I-1-c-8 | O | C₂H₅ |
| I-1-c-10 | O | C₂H₅ |
| I-1-c-11 | O | C₂H₅ |
| I-1-c-12 | O | C₂H₅ |
| I-1-c-13 | O | C₂H₅ |
| I-1-c-14 | O | C₆H₅—CH₂— |
| I-1-c-15 | O | CH₂=CH—CH₂— |
| I-1-c-16 | O | C₂H₅ |
| I-1-c-17 | O | C₂H₅ |
| I-1-c-18 | O | C₂H₅ |
| I-1-c-19 | O | C₂H₅ |
| I-1-c-20 | O | C₂H₅. |

2. The compound of claim 1, wherein the compound is I-1-a-3, I-1-a-8, I-1-a-12, I-1-a-13, I-1-a-18, I-1-a-19, I-1-a-20, I-1-b-3, I-1-b-16, I-1-c-12, or I-1-c-17.

3. A compound of the formula (I-1-c-3):

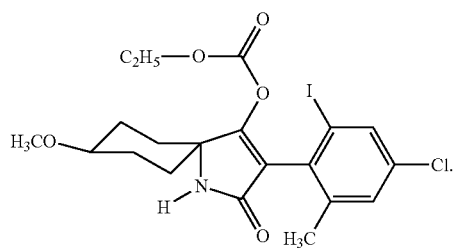 [SMILES: CCOC(=O)OC1=C(c2c(C)cc(Cl)cc2I)C(=O)NC12CCC(OC)CC2]

4. A pesticide composition and/or herbicide composition comprising
at least one compound of claim 1 and; an extender and/or a surfactant.

5. A method for controlling an animal pest and/or unwanted vegetation, comprising
contacting one or more compounds of claim 1 with the pest, the unwanted vegetation, and/or their habitats.

6. A process for preparing a pesticide composition or a herbicide composition, comprising
mixing one or more compounds of claim 1 with an extender and/or a surfactant.

7. A composition comprising,
(a') at least one compound of claim 1,
and
(b') at least one crop plant compatibility-improving compound;
wherein the crop plant compatibility-improving compound is at least one of:
4-dichloroacetyl-1-oxa-4-azaspiro[4.5]decane (AD-67, MON-4660),
1-dichloroacetylhexahydro-3,3,8a-trimethylpyrrolo[1,2-a]pyrimidin-6(2H)-one (dicyclonon, BAS-145138),
4-dichloroacetyl-3,4-dihydro-3-methyl-2H-1,4-benzoxazine (benoxacor),
1-methylhexyl 5-chloroquinoline-8-oxyacetate (cloquintocet-mexyl)
3-(2-chlorobenzyl)-1-(1-methyl-1-phenylethyl)urea (cumyluron),
α-(cyanomethoximino)phenylacetonitrile (cyometrinil),
2,4-dichlorophenoxyacetic acid (2,4-D),
4-(2,4-dichlorophenoxy)butyric acid (2,4-DB),
1-(1-methyl-1-phenylethyl)-3-(4-methylphenyl)urea (daimuron, dymron),
3,6-dichloro-2-methoxybenzoic acid (dicamba),
S-1-methyl-1-phenylethyl piperidine-1-thiocarboxylate (dimepiperate),
2,2-dichloro-N-(2-oxo-2-(2-propenylamino)ethyl)-N-(2-propenyl)acetamide (DKA-24),
2,2-dichloro-N,N-di-2-propenylacetamide (dichlormid),
4,6-dichloro-2-phenylpyrimidine (fenclorim),
ethyl 1-(2,4-dichlorophenyl)-5-trichloromethyl-1H-1,2,4-triazole-3-carboxylate (fenchlorazole-ethyl),
phenylmethyl 2-chloro-4-trifluoromethylthiazole-5-carboxylate (flurazole),
4-chloro-N-(1,3-dioxolan-2-ylmethoxy)-α-trifluoroacetophenone oxime (fluxofenim),
3-dichloroacetyl-5-(2-furanyl)-2,2-dimethyloxazolidine (furilazole, MON-13900),
ethyl 4,5-dihydro-5,5-diphenyl-3-isoxazolecarboxylate (isoxadifen-ethyl),
1-(ethoxycarbonyl)ethyl 3,6-dichloro-2-methoxybenzoate (lactidichlor),
(4-chloro-o-tolyloxy)acetic acid (MCPA),
2-(4-chloro-o-tolyloxy)propionic acid (mecoprop), diethyl 1-(2,4-dichorophenyl)-4,5-dihydro-5-methyl-1H-pyrazole-3,5-dicarboxylate (mefenpyr-diethyl)
2-dichloromethyl-2-methyl-1,3-dioxolane (MG-191),
2-propenyl-1-oxa-4-azaspiro[4.5]decane-4-carbodithioate (MG-838),
1,8-naphthalic anhydride,
α-(1,3-dioxolan-2-ylmethoximino)phenylacetonitrile (oxabetrinil),
2,2-dichloro-N-(1,3-dioxolan-2-ylmethyl)-N-(2-propenyl)acetamide (PPG-1292),
3-dichloroacetyl-2,2-dimethyloxazolidine (R-28725),
3-dichloroacetyl-2,2,5-trimethyloxazolidine (R-29148),
4-(4-chloro-o-tolyl)butyric acid,
4-(4-chlorophenoxy)butyric acid,
diphenylmethoxyacetic acid,
methyl diphenylmethoxyacetate,
ethyl diphenylmethoxyacetate,
methyl 1-(2-chlorophenyl)-5-phenyl-1H-pyrazole-3-carboxylate,
ethyl 1-(2,4-dichlorophenyl)-5-methyl-1H-pyrazole-3-carboxylate,
ethyl 1-(2,4-dichlorophenyl)-5-isopropyl-1H-pyrazole-3-carboxylate,
ethyl 1-(2,4-dichlorophenyl)-5-(1,1-dimethylethyl)-1H-pyrazole-3-carboxy late,
ethyl 1-(2,4-dichlorophenyl)-5-phenyl-1H-pyrazole-3-carboxylate,
ethyl 5-(2,4-dichlorobenzyl)-2-isoxazoline-3-carboxylate,
ethyl 5-phenyl-2-isoxazoline-3-carboxylate,
ethyl 5-(4-fluorophenyl)-5-phenyl-2-isoxazoline-3-carboxylate,
1,3-dimethylbut-1-yl 5-chloroquinoline-8-oxyacetate,
4-allyloxybutyl 5-chloroquinoline-8-oxyacetate,
1-allyloxyprop-2-yl5-chloroquinoline-8-oxyacetate,
methyl 5-chloroquinoxaline-8-oxyacetate,
ethyl 5-chloroquinoline-8-oxyacetate,
allyl 5-chloroquinoxaline-8-oxyacetate,
2-oxoprop-1-yl5-chloroquinoline-8-oxyacetate,
diethyl 5-chloroquinoline-8-oxymalonate,
diallyl 5-chloroquinoxaline-8-oxymalonate,
diethyl 5-chloroquinoline-8-oxymalonate,
4-carboxychroman-4-ylacetic acid (AC-304415),
4-chlorophenoxyacetic acid,
3,3'-dimethyl-4-methoxybenzophenone,
1-bromo-4-chloromethylsulfonylbenzene,
1-[4-(N-2-methoxybenzoylsulfamoyl)phenyl]-3-methylurea (also known as N-(2-methoxybenzoyl)-4-[(methylaminocarbonyl)amino]benzenesulfonamide),
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthylsulfamoyl)phenyl]-3,3-dimethylurea,
N-(2-methoxy-5-methylbenzoyl)-4-(cyclopropylaminocarbonyl)benzenesulfonamide,
and/or one of the following compounds
of the general formula (IIa)

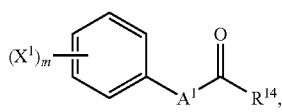

(IIa)

the general formula (IIb)

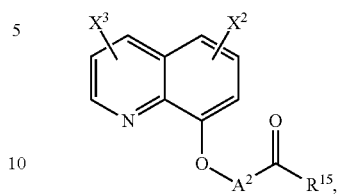

(IIb)

and/or of the general formula (IIc)

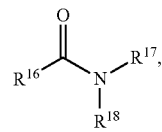

(IIc)

wherein
m is 0, 1, 2, 3, 4 or 5,
$A^1$ represents one of the divalent heterocyclic groupings shown below:

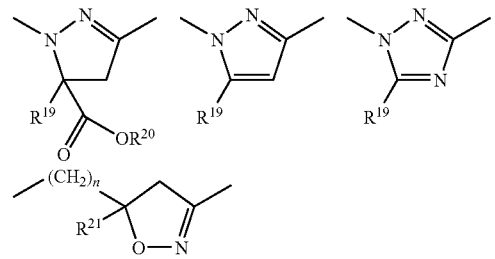

n is 0, 1, 2, 3, 4 or 5,
$A^2$ represents optionally $C_1$-$C_4$-alkyl- and/or $C_1$-$C_4$-alkoxy-carbonyl- and/or $C_1$-$C_4$-alkenyloxy-carbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)-amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino,
$R^{16}$ represents in each case an optionally fluoro, chloro or bromo-substituted $C_1$-$C_4$-alkyl,
$R^{17}$ represents hydrogen, in each case an optionally fluoro, chloro or bromo-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or an optionally fluoro, chloro or bromo- or $C_1$-$C_4$-alkyl-substituted phenyl,
$R^{18}$ represents hydrogen, in each case an fluoro, chloro or bromo-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or an optionally fluoro, chloro or bromo- or $C_1$-$C_4$-alkyl-substituted phenyl,
$R^{17}$ and $R^{18}$ also together represent $C_3$-$C_6$-alkanediyl or $C_2$-$C_5$-oxaalkanediyl, each of which may be optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case an optionally fluoro, chloro or bromo-substituted $C_1$-$C_4$-alkyl, $C_3$-$C_6$-cycloalkyl or phenyl, $R^{20}$ represents hydrogen, in each case an optionally hydroxyl-, cyano-, halogen- or $C_1$-$C_4$-alkoxy-substituted $C_3$-$C_6$-cycloalkyl or tri-($C_1$-$C_4$-alkyl)-silyl, $R^{21}$ represents hydrogen, cyano, halogen, or represents in each case an optionally fluoro, chloro or bromo-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds
of the general formula (IId)

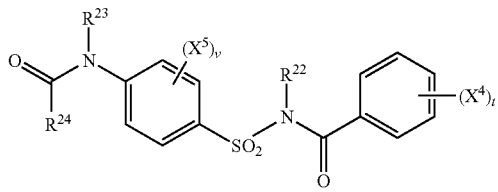
(IId)

or of the general formula (IIe)

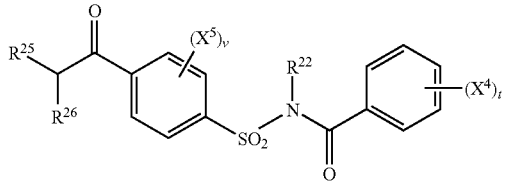
(IIe)

wherein
t is 0, 1, 2, 3, 4 or 5,
v is 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino,
$R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl,
$R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

8. The composition as claimed in claim 7, wherein the crop plant compatibility-improving compound comprises at least one of
cloquintocet-mexyl,
fenchlorazole-ethyl,
isoxadifen-ethyl,
mefenpyr-diethyl,
furilazole,
fenclorim,
cumyluron,
dymron,
compound IIe-5, or
compound IIe-11;
wherein the compounds IIe-5 or IIe-11 have the following formulae:

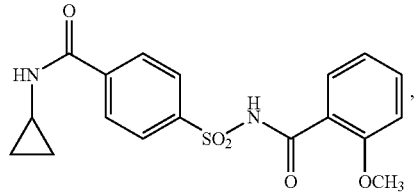
(IIe-5)

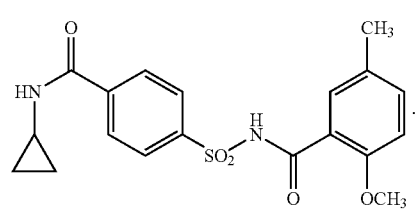
(IIe-11)

9. The composition of claim 7, wherein the crop plant compatibility-improving compound is mefenpyr-diethyl.

10. A method for controlling unwanted vegetation, comprising contacting the composition of claim 7 with the vegetation or its habitat.

11. A method for controlling unwanted vegetation, comprising contacting a compound of claim 1 and a crop plant compatibility-improving compound, separately in close temporal succession, or as a mixture, with the unwanted vegetation or its habitat;
wherein the crop plant-compatibility-improving compound is at least one of:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138),
4-dichloroacetyl-3,4-dihydro-3-methyl-2H-1,4-benzoxazine (benoxacor),
1-methylhexyl 5-chloroquinoline-8-oxyacetate (cloquintocet-mexyl),
3-(2-chlorobenzyl)-1-(1-methyl-1-phenylethyl)urea (cumyluron),
α-(cyanomethoximino)phenylacetonitrile (cyometrinil),
2,4-dichlorophenoxyacetic acid (2,4-D),
4-(2,4-dichlorophenoxy)butyric acid (2,4-DB),
1-(1-methyl-1-phenylethyl)-3-(4-methylphenyl)urea (daimuron, dymron),
3,6-dichloro-2-methoxybenzoic acid (dicamba),
S-1-methyl-1-phenylethyl piperidine-1-thiocarboxylate (dimepiperate),
2,2-dichloro-N-(2-oxo-2-(2-propenylamino)ethyl)-N-(2-propenyl)acetamide (DKA-24),
2,2-dichloro-N,N-di-2-propenylacetamide (dichlormid),
4,6-dichloro-2-phenylpyrimidine (fenclorim),
ethyl 1-(2,4-dichlorophenyl)-5-trichloromethyl-1H-1,2,4-triazole-3-carboxylate (fenchlorazole-ethyl),
phenylmethyl 2-chloro-4-trifluoromethylthiazole-5-carboxylate (flurazole),
4-chloro-N-(1,3-dioxolan-2-ylmethoxy)-α-trifluoroacetophenone oxime (fluxofenim),
3-dichloroacetyl-5-(2-furanyl)-2,2-dimethyloxazolidine (furilazole, MON-13900),
ethyl 4,5-dihydro-5,5-diphenyl-3-isoxazolecarboxy late (isoxadifen-ethyl),
1-(ethoxycarbonyl)ethyl 3,6-dichloro-2-methoxybenzoate (lactidichlor),
(4-chloro-o-tolyloxy)acetic acid (MCPA),
2-(4-chloro-o-tolyloxy)propionic acid (mecoprop),
diethyl 1-(2,4-dichorophenyl)-4,5-dihydro-5-methyl-1H-pyrazole-3,5-dicarboxylate (mefenpyr-diethyl),
2-dichloromethyl-2-methyl-1,3-dioxolane (MG-191),
2-propenyl-1-oxa-4-azaspiro[4.5]decane-4-carbodithioate (MG-838),
1,8-naphthalic anhydride,
α-(1,3-dioxolan-2-ylmethoximino)phenylacetonitrile (oxabetrinil),
2,2-dichloro-N-(1,3-dioxolan-2-ylmethyl)-N-(2-propenyl)acetamide (PPG-1292),
3-dichloroacetyl-2,2-dimethyloxazolidine (R-28725),
3-dichloroacetyl-2,2,5-trimethyloxazolidine (R-29148),
4-(4-chloro-o-tolyl)butyric acid,
4-(4-chlorophenoxy)butyric acid,
diphenylmethoxyacetic acid,
methyl diphenylmethoxyacetate,
ethyl diphenylmethoxyacetate,
methyl 1-(2-chlorophenyl)-5-phenyl-1H-pyrazole-3-carboxylate,
ethyl 1-(2,4-dichlorophenyl)-5-methyl-1H-pyrazole-3-carboxylate,
ethyl 1-(2,4-dichlorophenyl)-5-isopropyl-1H-pyrazole-3-carboxylate,
ethyl 1-(2,4-dichlorophenyl)-5-(1,1-dimethylethyl)-1H-pyrazole-3-carboxylate,
ethyl 1-(2,4-dichlorophenyl)-5-phenyl-1H-pyrazole-3-carboxylate,
ethyl 5-(2,4-dichlorobenzyl)-2-isoxazoline-3-carboxylate,
ethyl 5-phenyl-2-isoxazoline-3-carboxylate,
ethyl 5-(4-fluorophenyl)-5-phenyl-2-isoxazoline-3-carboxylate,
1,3-dimethylbut-1-yl 5-chloroquinoline-8-oxyacetate,
4-allyloxybutyl 5-chloroquinoline-8-oxyacetate,
1-allyloxyprop-2-yl5-chloroquinoline-8-oxyacetate,
methyl 5-chloroquinoxaline-8-oxyacetate,
ethyl 5-chloroquinoline-8-oxyacetate,
allyl 5-chloroquinoxaline-8-oxyacetate,
2-oxoprop-1-yl 5-chloroquinoline-8-oxyacetate,
diethyl 5-chloroquinoline-8-oxymalonate,
diallyl 5-chloroquinoxaline-8-oxymalonate,
diethyl 5-chloroquinoline-8-oxymalonate,
4-carboxychroman-4-ylacetic acid (AC-304415),
4-chlorophenoxyacetic acid,
3,3'-dimethyl-4-methoxybenzophenone,
1-bromo-4-chloromethylsulfonylbenzene,
1-[4-(N-2-methoxybenzoylsulfamoyl)phenyl]-3-methylurea (also known as N-(2-methoxybenzoyl)-4-[(methylaminocarbonyl)amino]benzenesulfonamide),
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthylsulfamoyl)phenyl]-3,3-dimethylurea,
N-(2-methoxy-5-methylbenzoyl)-4-(cyclopropylaminocarbonyl)benzenesulfonamide,
and/or one of the following compounds
of the general formula (IIa)

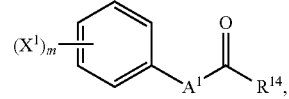

(IIa)

the general formula (IIb)

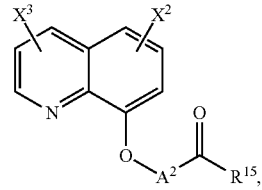

(IIb)

and/or of the general formula (IIc)

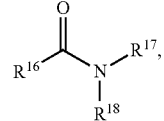

(IIc)

wherein m is 0, 1, 2, 3, 4 or 5, $A^1$ represents one of the divalent heterocyclic groupings shown below:

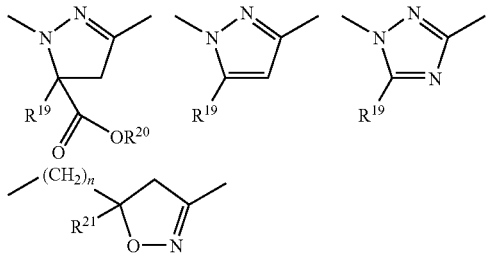

n is 0, 1, 2, 3, 4 or 5, $A^2$ represents optionally $C_1$-$C_4$-alkyl- and/or $C_1$-$C_4$-alkoxy-carbonyl- and/or $C_1$-$C_4$-alkenyloxy-carbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)-amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino, $R^{16}$ represents in each case an optionally fluoro, chloro or bromo-substituted $C_1$-$C_4$-alkyl, $R^{17}$ represents hydrogen, in each case an optionally fluoro, chloro or bromo-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or an optionally fluoro, chloro or bromo- or $C_1$-$C_4$-alkyl-substituted phenyl, $R^{18}$ represents hydrogen, in each case an optionally fluoro, chloro or bromo-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or an optionally fluoro, chloro or bromo- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which may be optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case an optionally fluoro, chloro or bromo-substituted $C_1$-$C_4$-alkyl, $C_3$-$C_6$-cycloalkyl or phenyl, $R^{20}$ represents hydrogen, in each case an optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{21}$ represents hydrogen, cyano, halogen, or represents in each case an optionally fluoro, chloro or bromo-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, C1-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, of the general formula (IId)

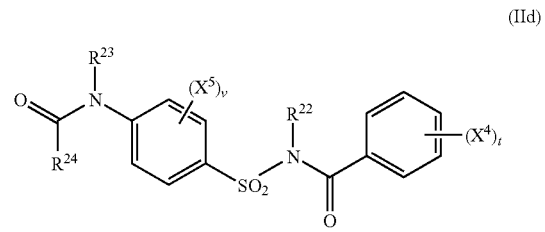

(IId)

or of the general formula (IIe)

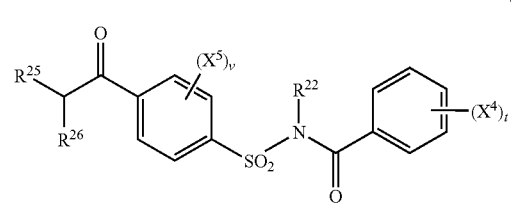

(IIe)

wherein t is 0, 1, 2, 3, 4 or 5, v is 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

* * * * *